US005856552A

United States Patent [19]
Fujiwa et al.

[11] Patent Number: 5,856,552
[45] Date of Patent: Jan. 5, 1999

[54] COMPOSITION COMPRISING A NOVEL PHOSPHATIZED ALICYCLIC COMPOUND AND PROCESS FOR THE PREPARATION THEREOF

[75] Inventors: Takaaki Fujiwa, Ohtake; Terumasa Daito, Sakai; Takashi Yamamoto; Takashi Matsufuji, both of Osaka, all of Japan

[73] Assignee: Daicel Chemical Industries, Ltd., Osaka-Fu, Japan

[21] Appl. No.: 935,652

[22] Filed: Sep. 23, 1997

Related U.S. Application Data

[60] Continuation of Ser. No. 486,503, Jun. 7, 1995, abandoned, which is a division of Ser. No. 270,284, Jul. 5, 1994, Pat. No. 5,527,941.

[30] Foreign Application Priority Data

Jul. 5, 1993 [JP] Japan .................................. 5-171747
Jul. 5, 1993 [JP] Japan .................................. 5-191745
Jul. 5, 1993 [JP] Japan .................................. 5-191746

[51] Int. Cl.$^6$ ...................................................... C07F 9/09
[52] U.S. Cl. ............................................................ 558/105
[58] Field of Search ............................................. 558/105

[56] References Cited

U.S. PATENT DOCUMENTS

2,226,534  4/1940  Lichty .
3,423,440  1/1969  Cawley et al. ...................... 558/105 X
4,356,323  10/1982  Kleeman et al. .
4,358,615  11/1982  Kleeman et al. .
4,360,697  11/1982  Kleeman et al. .
5,023,379  6/1991  Felder et al. .

FOREIGN PATENT DOCUMENTS

0075929  4/1983  European Pat. Off. .

*Primary Examiner*—Michael G. Ambrose
*Attorney, Agent, or Firm*—Sughrue, Mion, Zinn, Macpeak & Seas, PLLC

[57] ABSTRACT

Disclosed is a composition which comprises a phosphatized alicyclic compound represented by the formula (I), (II), (III), (VII) or (IX), shown in the specification.

The composition of the present invention is useful as an antigassing agent for a water-based coating composition containing metallic, for example, aluminum powder or flake pigments for coating automobile bodies, etc., a flame retardant for various resins and a water-based ink, and the like.

8 Claims, 65 Drawing Sheets

COMPOSITION COMPRISING A NOVEL PHOSPHATIZED ALICYCLIC COMPOUND AND PROCESS FOR THE PREPARATION THEREOF

This is a continuation of application Ser. No. 08/486,503 filed Jun. 7, 1995, now abandoned, which is a divisional of application Ser. No. 08/270,284, filed Jul. 5, 1994, issued as U.S. Pat. No. 5,527,941 on Jun. 18, 1996.

FIELD OF THE INVENTION

The present invention relates to a composition which comprises a novel phosphatized alicyclic compound and a process for the preparation thereof. The composition of the present invention can be preferably used as an antigassing agent for a water-based coating composition containing metallic, for example, aluminum powder or flake, pigments for coating automobile bodies, etc., a flame retardant for various resins and a water-based ink, and the like.

BACKGROUND OF THE INVENTION

It has been well known to incorporate metallic pigments in coating compositions, in particular it is an established practice to use aluminum flake pigments in compositions intended for the production of so-called "glamour" finishes on automobile bodies, whereby a differential tight reflection is effected, depending on the angle at which the coated surface is viewed. Generally speaking, such coating compositions have been solvent-based, in common with the other coating compositions employed in the automobile industry. The tend is growing, however, toward the use of water-based coating compositions due to the need to improve work environments and reduce pollution.

For example, British Patent Specification No. 2073609 teaches a coating process in which a specified type of water-based base coat composition containing pigments, especially aluminum flake pigment is applied to a base surface, after which a transparent top coat composition is applied to the base coat.

However, difficulties arise in incorporating metallic pigments, particularly aluminum or aluminum alloys, into water-borne coating compositions, because the pigment tends to react with water to produce hydrogen.

This leads to problems, especially if compositions are stored in closed containers.

Ways have been proposed to minimize or prevent this "gassing effect" most involving some form of chemical treatment of the metallic pigment to render it less reactive toward the aqueous medium of the coating composition. It is known that ortho-phosphoric acid is effective for this purpose, but its presence in coating compositions leads to unacceptable poor humidity resistance in films derived from them.

Alkyl esters of phosphoric acid can overcome the problem to a limited extent, but their use involves an unsatisfactory compromise between the inhibition of gassing and a tendency toward deteriorating mechanical properties in the derived coatings, in particular poor adhesion between the base coat containing the agent and the transparent top coat.

The same is true of nonphosphorus-containing treatment agents, such as dimer acids, proposed for this purpose in British Patent Specification 2043092.

Furthermore, U.S. Pat. No, 4,621,112 [corresponding to Japanese Patent Unexamined Publication No. 47771/1986] discloses the use of a reaction product of a Phosphoric acid and one or more compounds which contain in the molecule at least one epoxide group and which also contains in the molecule at least one aromatic or alicyclic group wherein one or both reactants contain an aliphatic group of more than six carbon atoms with the aliphatic group not exceeding 65% by weight. The reaction product provides antigassing without sacrificing the mechanical properties of the coatings.

In the instance of the additive, although mechanical properties are not affected, coating appearance, particularly "flop" is adversely affected. The "flop" means the visual change in brightness of the metallic aluminum flake with a change in viewing angle, that is, a change of from 90 to 180 degrees.

The greater the visual change from a light to dark appearance, the better the flop. Flop accentuates the lines and curves of a coated angle. Furthermore, a starting material of the antigassing agent in the USP is an aromatic glycidyl epoxy compound such as a bisphenol A glycidyl epoxy compound, prepared by the use of epichlorohydrin, resulting in that chlorine is brought in the gassing agent. Even in exceedingly minor amounts, the presence of chlorine adversely affects metallic pigments.

Still further, in the case when the starting material is an aromatic glycidyl compound, it would not be stable with light and oxygen, resulting in inferior weatherability.

In addition, European Patent Publication No. 0319971 [corresponding to Japanese Patent Unexamined Publication No. 190765/1989] discloses a water-based coating composition containing aluminum flakes and an antigassing phosphatized acrylic polymer in which an epoxy-functional acrylic polymer is allowed to react with a phosphoric aced, or forming in situ phophatized polymer after an acrylic monomer is allowed to react with a phosphoric acid.

However, it has been found that the antigassing agent described in the EP is somewhat inferior from the viewpoint of a balanced stability of the composition, the tone of color in the coated layer, anti-strippability in the coated layer and weatherability or moisture resistance in the coated layer. Furthermore, the molecular weight of phosphatized acrylic polymer is not easy to adjust.

As a result of an intensive investigation, the inventors of this invention have now found that it is possible to solve the problems as described hereinabove by the use of the phosphatized alicyclic compound of the present invention as an antigassing agent for a water-based coating composition containing aluminum powder or flake pigments.

SUMMARY OF THE INVENTION

A primary object of the present invention is to develop a novel phosphatized alicyclic compound useful as an excellent antigassing agent for a water-based coating composition containing aluminum powder or flake pigments.

A first aspect of the present invention is a composition which comprises a phosphatized alicyclic compound represented by the formula (I):

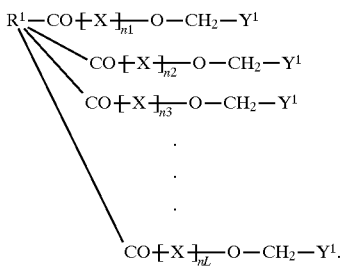
(I)

A second aspect of the present invention is a composition which comprises a phosphatized alicyclic compound represented by formula (II):

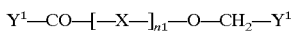
(II).

A third aspect of the present invention is a composition which comprises a phosphatized alicyclic compound represented by formula (III):

$$Y^1—CH_2OCO(CH_2)_4COO—CH_2Y^1 \qquad (III).$$

In the formulae (I), (II) and (III), $R^1$ is an alkyl group or alkenyl group having a carbon number from 1 to 30; X is $—O—CR^aR^b)_nCO—$ in which $R^a$ and $R^b$ are independently hydrogen or a methyl group; n is a number of 4 to 8; n1 to nL represent 0 or a number above 0, respectively; n1+n2+ n3+ . . . +nL is 1 or a number above 1; and $Y^1$ is a structural group represented by the formula (1):

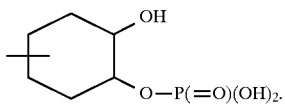
(1)

Fourth, fifth and sixth aspects of the present invention are processes for the preparation of compositions comprising phosphatized alicyclic compounds represented by,, formulae (I) (II) and (III), respectively.

A seventh aspect of the present invention is a composition which comprises a phosphatized alicyclic compound represented by the formula (VII):

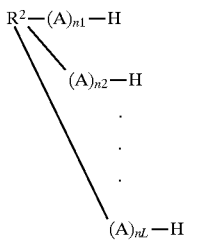
(VII)

wherein $R^2$ is a residual group of an organic compound having at least one active hydrogen atom, n1 to nL represent an integer of 0 to 30, respectively, n1+n2+n3+ . . . +nL is an integer of from 1 to 100, L is an integer of from 1 to 10 which corresponds to the number of the active hydrogen atom in the organic compound and A represents an oxycyclohexane structure represented by the formula:

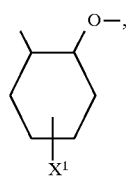

$X^1$ represents the following structural units:

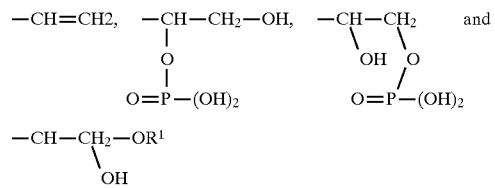

wherein $R^x$ is any of hydrogen, an alkyl group, an alkylcarbonyl group and an arylcarbonyl group.

An eighth aspect of the present invention is a process for the preparation of the composition which comprises a phosphatized alicyclic compound represented by the formula (VII).

A ninth aspect of the present invention is a composition which comprises a phosphatized alicyclic compound represented by the formula (IX):

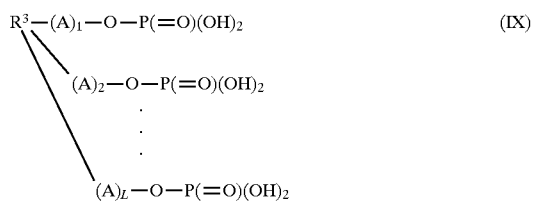
(IX)

wherein $R^3$ is an alkyl or alkenyl group having a carbon number of from 1 to 20, A is an alkyl or alkenyl group having a carbon number of from 1 to 20 and L represents an integer of from 1 to 10.

A tenth aspect of the present invention is a process for the preparation of a composition which comprises a phosphatized alicyclic compound represented by the formula (IX).

DETAILED DESCRIPTION OF THE INVENTION

Figure 1:
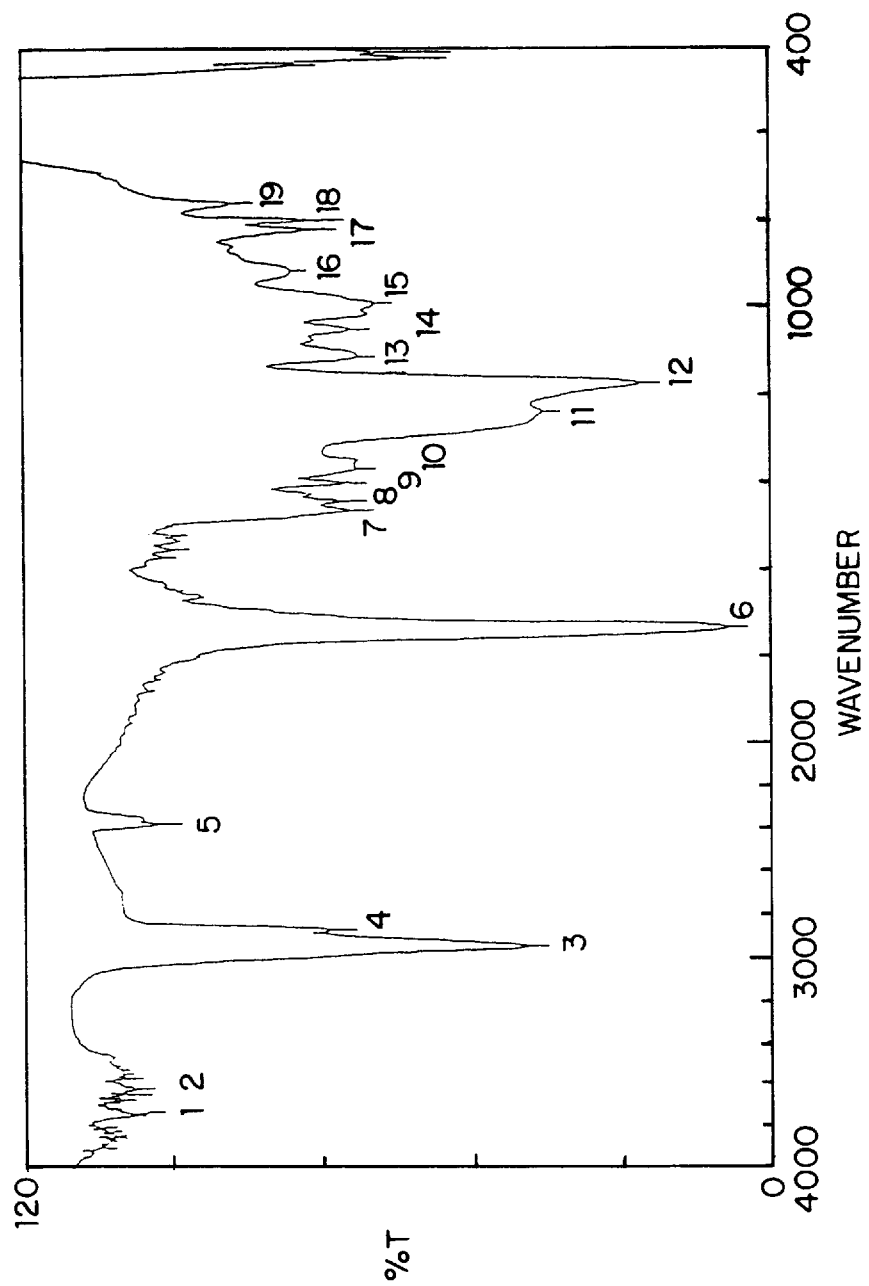
FIG. 1 is an Infra-Red(IR) spectra chart related to the starting epoxy compound used in Example 1.

The present invention is described hereinafter in more detail.

According to a first aspect of the present invention, there is provided a composition which comprises a phosphatized alicyclic compound represented by the formula (I):

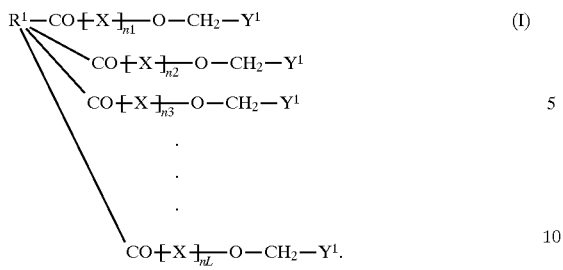  (I)

According to a second aspect of the present invention, there is provided a composition represented by the formula (II):

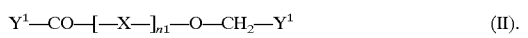  (II).

According to a third aspect of the present invention, there is provided a composition represented by the formula (III);

  (III).

In the formulae (I), (II) and (III), $R^1$ is an alkyl group or alkenyl group having a carbon number of 1 to 30; X is $-O-(CR^aR^b)_nCO-$; n is a number ranging from 4 to 8; n1 to nL represent 0 or a number above 0; n1+n2+n3+ . . . +nL is 1 or a number above 1; and $Y^1$ is a structural group represented by the formula (1):

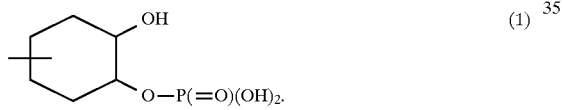  (1)

In X, $R^a$ and $R^b$ each represents hydrogen or methyl group, exchangeable with each other, depending upon starting lactone compounds. For example, in the case when epsilon-caprolactone is used as the starting material, $R^a$ and $R^b$ represent hydrogen.

Furthermore, in the case when beta-methyl-delta-valerolactone is used as the starting material, $R^a$ and $R^b$ represent a methyl group or hydrogen. Still further, in the case when 3-methyl-caprolactone is used as a starting material, $R^a$ and $R^b$ represent a methyl group and hydrogen.

n, which represents an integer of 4 to 8, is also decided based on the starting lactone compounds. n1 to nL corresponds to a mol number of the lactone compound introduced into the phosphatized compound (I), and L is an integer larger than 0.

$R^1$ is an alkyl group or alkenyl group having a carbon number of 1 to 30 which is based on a starting material.

According to fourth, fifth and sixth aspects of the present invention there are provided processes for the preparation of compositions represented by the formulae (I), (II) and (III).

Phosphatized compounds (I), (II) and (III) can be prepared by reacting an alicyclic epoxy compound represented by formulae (IV), (V) and (VI) with a compound having the $-OP(=O)(OH)_2$ group in the molecule, respectively:

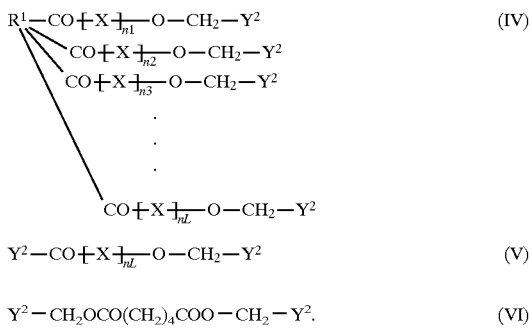  (IV)

(V)

$Y^2-CH_2OCO(CH_2)_4COO-CH_2-Y^2$.  (VI)

In formulae (IV), (V) and (VI), $R^1$ is an alkyl group or alkenyl group having a carbon number of from 1 to 30; X is $-O-(CR^aR^b)_nCO-$ in which $R^a$ and $R^b$ are independently hydrogen or a methyl group; n is a number ranging from 4 to 8; n1 to nL represent 0 or a number above 0; n1+n2+n3+ . . . +nL is 1 or a number above 1; and $Y^2$ is a structural group represented by the formula

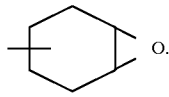

In formulae (I) and (IV), $R^1$ may include an alicyclic or linear aliphatic group and may have double bonds.

A compound from which $R^1$ is derived specifically includes:

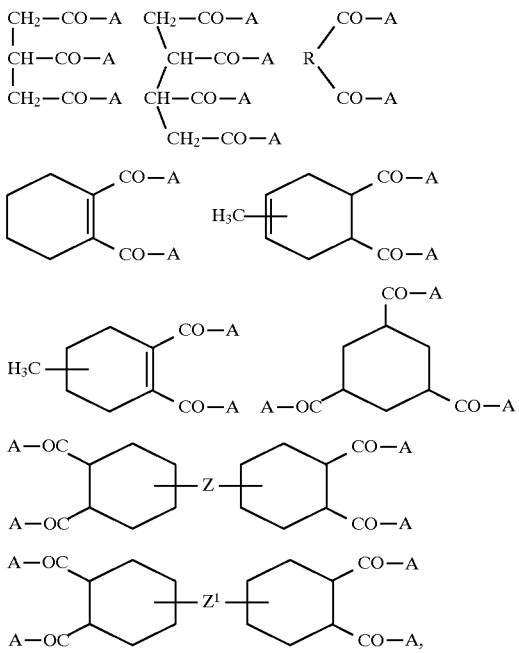

in formulae, Z is $-COOCH_2CH_2OCO-$ and $Z^1$ is

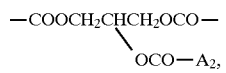

A is —O[—(CH$_2$)$_5$—CO—]$_n$OCH$_2$Y$^1$ and A$^2$ is

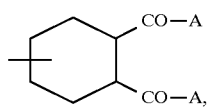

Y$^1$ is

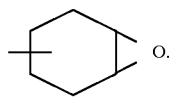

The alicyclic epoxy compound (IV) which is a starting material in the first aspect can be prepared by esterification in which the above-described carboxylic compounds or corresponding anhydride thereof are allowed to react with 3,4-epoxycyclohexenemethanol and a lactone compound such as epsilon-caprolactone.

The alicyclic epoxy compound (IV) in the first aspect and preparation process thereof are detailed in U.S. Pat. No. 5,169,965, European Patent Publication No. 91401935.1 and Japanese Unexamined Publication (Kokai) No. 69360/1992.

The alicyclic epoxy compound (V) which is a starting material in the second aspect is an adduct in which n1 mols of a lactone compound is incorporated into 3,4-epoxycyclohexylmethyl-3,4-cyclohexanecarboxylate.

The alicyclic epoxy compound (V) in the second aspect and preparation processes thereof are detailed in U.S. patent application Ser. No. 707736/A, European Patent Publication No. 91401423 and Japanese Unexamined Publication (Kokai) No. 36263/1992.

Furthermore, in the above-mentioned alicyclic epoxy compounds (IV) and (V), epoxy equivalent and molecular weight can be widely adjusted by controlling added amounts of the lactone compound, having the advantage that alicyclic epoxy compounds can be widely adjusted in ductility and compatibility with pigments in a coating composition.

The alicyclic epoxy compound (VI) in the third aspect is bis(3,4-epoxycyclohexyl)adipate [for example, trade name ERL 4229 manufactured by Union Carbide Corporation) which can be prepared by the esterification of 2 mols of 3-cyclohexenemethanol with one mol of adipic acid, followed by epoxidation. The alicyclic epoxy compound (VI) and a process for the preparation thereof is ditailed in DE3528004.

According to a seventh aspect of the present invention, there is provided a composition which comprises a phosphatized alicyclic compound represented by the formula (VII):

 (VII)

wherein R$^2$ is a residual group of an organic compound having at least one active hydrogen atom; n1 to nL represent an integer of from 0 to 30; n1+n2+n3+ . . . +nL is an integer of from 1 to 100; L is an integer of from 1 to 10 which corresponds to the number of the active hydrogen atom in the organic compound; and A represents an oxycyclohexane structure represented by the formula:

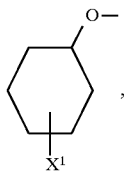

X$^1$ represents the following structural units:

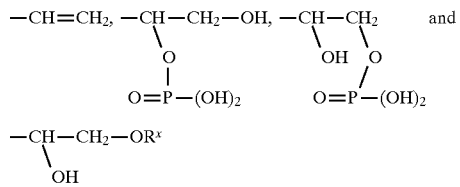

—CH—CH$_2$—OR$^x$
  \
  OH wherein R$^x$ is any of hydrogen, an alkyl group, an alkylcarbonyl group and an arylcarbonyl group.

Phosphatized compound (VII) in the seventh aspect can be prepared by phosphatization of the alicyclic epoxy compound (VIII) which is an epoxycyclohexanepolyether [trade name EHPE manufactured by Daicel Chemical Industries, Ltd.].

According to an eighth aspect of the present invention, there is provided a process for the preparation of a composition which comprises a phosphatized alicyclic compound represented by the formula (VII).

The process comprises reacting the composition which comprises an alicyclic compound represented by the formula (VIII):

$$R^2\begin{matrix}-(B)_{n1}-H\\ -(B)_{n2}-H\\ \vdots\\ -(B)_{nL}-H\end{matrix}$$ (VIII)

In formulae (VII) and (VIII), R$^2$ is a residual group of an organic compound having at least one active hydrogen atom.

The organic compound having at least one active hydrogen atom includes alcohols, phenols, carboxylic acid, amines and thiols.

As alcohols, either monohydric alcohols or polyhydric alcohols may be used. For instance, aliphatic alcohols such as methanol, ethanol, propanol, butanol, pentanol, hexanol, octanol; aromatic alcohols such as benzyl alcohol; polyhydric alcohols such as ethylene glycol, diethylene glycol, triethylene glycol, polyethylene glycol, propylene glycol, dipropylene glycol, 1,3-butanediol, 1,4-butanediol, pentanediol, 1,6-hexanediol, neopentyl glycol, neopentyl glycol oxypivalate, cyclohexanedimethanol, glycerine, diglycerine, polyglycerine, trimethylolpropane, trimethylol ethane, pentaerythritol, dipentaerythritol, a hydrogenated bisphenol A, a hydrogenated bisphenol F, a hydrogenated bisphenol S, etc., are included.

Phenols include phenol, cresol, catechol, pyrogallol, hydroquinone, hydroquinone monoethylether, bisphenol A, bisphenol F, 4,4'-dihydroxybenzophenone, ,bisphenol S, phenol resins, cresol novolak resins, etc.

Carboxylic acids include formic acid, acetic acid, propionic acid, butyric acid, fatty acids of animal and vegetable oil and fats, fumaric acid, maleic acid, adipic acid, dodecanedioic acid, trimellitic acid, pyromellitic acid, polyacrylic acid, phthalic acid, isophthalic acid, terephthalic acid, etc.

In addition, compounds having a hydroxyl group together with a carboxylic acid group such as lactic acid, citric acid, oxycaproic acid, etc., are included.

Amines include monomethylamine, dimethylamine, monoethylamine, diethylamine, propylamine, monobutylamine, dibutylamine, pentylamine, hexylamine, cyclohexylamine, octylamine, dodecylamine, 4,4'-diaminodiphenylmethane, isophorondiamine, toluenediamine, hexamethylene diamine, xylene diamine, diethylene triamine, triethylene tetramine, ethanolamine, etc.

Thiols include mercaptans such as methyl mercaptan, ethyl mercaptan, propyl morcaptan, phenylmercaptan, etc., mercaptopropioic acid or polyhydric alcohol esters of mercaptopropioic acid, such as ethylene glycol bismercapto propionate, trimethylolpropane trimercapto propionate, pentaerythritol pentamercaptopropioic acid, etc.

Furthermore, other compounds having active hydrogen atoms include polyvinyl alcohol, partially hydrolyzed products of polyvinyl acetate, starch, cellulose, cellulose acetate, cellulose acetate butylate, hydroxyethyl cellulose, acrylic polyol resins, styrene-allyl alcohol copolymer resins, styrene-maleic acid copolymer resins, alkyd resins, polyester polyol resins, polyester carboxylic acid resins, polycaprolactone polyol resins, polypropylene polyol, polytetramethylene glycol, polycarbonatepolyols, and a polybutadiene having hydroxyl groups, cellulose polymers such as hydroxylethylcelluloses, cellulose acetates, etc.

Still further, the compounds having at least one active hydrogen atom may have an unsaturated double bond in their structure, examples of which include allyl alcohol, acrylic acid, methacrylic acid, 3-cyclohexenemethanol, tetrahydrophthalic acid, etc.

One or more of such compounds having active hydrogen atoms can be used. It is noted that water or small amounts of water contained in starting materials can also be used as an initiator without using the above-described compounds having active hydrogen atoms to prepare the compound represented by general formulae (VII) and (VIII).

n1 to nL represent an integer of 0 to 30; n1+n2+n3+ . . . +nL is an integer of 1 to 100; L is an integer of 1 to 10 which corresponds to the number of the active hydrogen atom in the organic compound; A represents an oxycyclohexane structure represented by the formula:

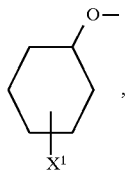

$X^1$ represents the following structural units:

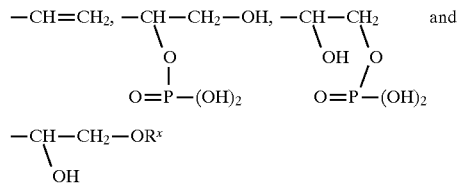

and B represents an oxycyclohexane structure represented by the formula:

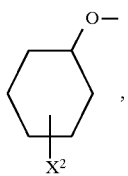

$X^2$ represents the following structural units:

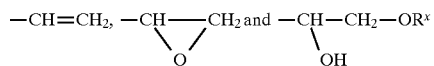

wherein $R^x$ is any of hydrogen, an alkyl group, an alkylcarbonyl group and an arylcarbonyl group, with a compound having the —OP(=O)(OH)$_2$ group in the molecule.

The alicyclic epoxy compound (VIII) and the preparation process thereof are detailed in U.S. Pat. No. 4,565,859, European Patent Publication No. 85100950 or Japanese Examined Publication (Kokoku) No. 10471/1992.

According to a ninth aspect of the present invention, there is provided a composition which comprises a phosphatized alicyclic compound represented by formula (IX):

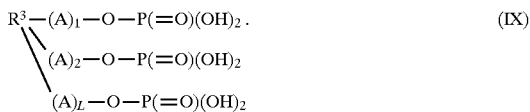

In formula (IX), $R^3$ is an alkyl or alkenyl group having a carbon number of 1 to 20. A is an alkyl or alkenyl group having a carbon number of 1 to 20 and L represents an integer of 1 to 10.

Specifically, $R^3$ and A are a residual group derived from propyleneglycol diglycidylether, diethyleneglycol diglycidylether, trimethylolpropane triglycidylether or pentaerythritol tetraglycidylether.

That is, the compound represented by formula (IX) is a phosphoric acid adduct of propyleneglycol diglycidylether, a phosphoric acid adduct of diethyleneglycol diglycidylether, a phosphoric acid adduct of trimethylolpropane triglycidylether and a phosphoric acid adduct of pentaerythritol tetraglycidylether.

According to a tenth aspect of the present invention, there is provided a process for the preparation of the composition which comprises a phosphatized alicyclic compound represented by formula (IX).

The process comprises phosphatization o: the glycidyl compounds with a phosphoric acid which is a compound having the —OP(=O)(OH)$_2$ group in the molecule.

Above-mentioned alicyclic epoxy compounds (IV), (V), (VI), (VIII) and glycidyl compounds are prepared by an epoxidation of corresponding starting materials with a peracid such as peracetic acid, resulting in epoxy compounds having an advantage of not containing chlorine, aromatic group and ethylenically unsaturated double bonds, and resulting in excellent weather-ability and stability in a coating composition.

Epoxidation can be carried out using an epoxidation agent such as a peracid or various hydroperoxides.

Peracids include performic acid, peracetic acid, perpropionic acid, perbenzoic acid and trifluoroperacetic acid, and the like.

Of these peracids, peracetic acid is the preferred epoxidation agent because it is available on an industrial basis at a moderate price and has high stability.

Hydroperoxides include hydroperoxide, tertiarybutylhydroperoxide, cumenperoxide and metachloroperbenzoic acid, and the like.

When carrying out the epoxidation reaction, a catalyst can be used as appropriate to the circumstances.

For example, in the case that peracetic acid is used as an epoxidation agent, an alkali such as sodium carbonate and an acid such as sulfuric acid, can be used as a catalyst.

Furthermore, in the case of using hydroperoxides, it is possible to obtain a catalytic effect, for example, using a mixture of tungstic acid and sodium hydroxide together with hydrogen peroxide, or hexacarbonylmolybudenum together with tertiary butyl hydroperoxide.

Epoxidation is carried out in the absence or the presence of a solvent, while controlling the reaction temperature based on the apparatus to be used and the properties of the raw materials.

The temperature region of the epoxidation reaction can be selected according to the reactivity of the epoxidation agent.

For peracetic acid, which is the preferable epoxidation agent, the preferred temperature is 0° to 70° C.

If the temperature is below 0° C., the reaction is slow, but if the temperature exceeds 70° C., peracetic acid may decompose.

For tertiary butylhydroperoxide/molybdenumdioxide diacetyl acetate, which is an example of a hydroperoxide, the preferable temperature is 20° C. to 150° C., based on the same consideration.

The use of solvents for dilution is effective for slowing the velocity of reaction of the raw materials and stabilizing the epoxidation agent.

In the case when peracetic acid is used as the epoxidation agent, preferred solvents include aromatic compounds such as benzene, toluene and xylene; a hydrocarbon such as hexane and cyclohexane; a halogenated compound such as carbontetrachloride and chloroform; and ester compounds such as ethyl acetate.

Of these solvents, ethyl acetate is especially preferred.

The molar ratio of the epoxidation agent to be used with respect to unsaturated bonds is selected based on the proportion of unsaturated bonds it is desired to retain.

When preparing epoxy compositions having many epoxy groups, an equal or higher molar ratio of epoxidation agents to unsaturated bonds is preferably used, but using amounts of epoxidation agents at a molar ratio exceeding 10/1 with respect to the unsaturated bonds is not preferable because of the cost and side reactions described hereinafter.

For peracetic acid, a preferable molar ratio is 1/1 to 5/1.

Phosphatized compounds in all aspects of the present invention can be prepared by phosphatization of the starting alicyclic epoxy compounds with a phosphoric acid which is a compound having the —OP(=O)(OH)$_2$ group in the molecule.

The phosphoric acid, useful therein, includes hydrated to pure phosphoric acid, i.e., from about 70% to about 100% phosphoric acid, and preferably about 85% phosphoric acid, which is also called orthophosphoric acid, because of its ready availability in industrial production.

In the case when the concentration of phosphoric acid is less than 70%, it is not preferred because of too much water.

Furthermore, equivalents of phosphoric acid, such as condensed forms, e.g., polymeric, partial anhydrides or esters of phosphoric acid, pyrophosphoric acid, or triphosphoric acid can be employed.

Still further, a monoester of orthophosphoric acid, specifically, monobutylphosphate, monoamylphosphate, monononylphosphate, monocetylphosphate, monophenylphosphate and monobenzylphosphate can be also employed.

In the reaction of phosphoric acid or its equivalents with alicyclic epoxy compounds, the ratio of reactants is such that all or virtually all of the epoxy moiety is allowed to react. Specifically, herein are used mol ratios generally about 0.5 to 4 and preferably about 1 to 2 of phosphoric acid to the alicyclic epoxy compound, based on mole of phosphorous per epoxy group.

In the case when mol ratios are less than 0.5, the phosphatized compound itself obtained is unstable, and in the case when the mol ratios exceed 4, the reaction is not readily controlled.

Reaction temperatures of generally about 25° C. to 150° C. and preferably about 50° C. to about 100° C. can be employed.

In the case when the temperatures are less than 25° C., the reaction is slow. In the case when the temperatures exceed 150° C., the reaction is not readily controlled.

The reaction may be neat or in the presence of solvents that are usually inert to this reaction.

Examples of preferred solvents include an aromatic solvent such as benzene, toluene, xylene and the like, a ketone solvent such as methylethylketone, cyclohexanone, methylisobutylketone, isophorone and the like; a hydrocarbon solvent such as hexane, heptane, cyclohexane and the like; an ether compound such as diethylether, tetrahydrofuran, dioxane, propyleneglycol monopropylether and the like; an ester such as ethylacetate, isopropyl acetate, butylglycol acetate and the like; and halogenated solvents which do not contain active hydrogen atoms.

Solvents are employed in amounts generally of 0.1 to 20 mols and preferably from 0.5 to 2 mols based on 1 mole of starting epoxy compounds.

In the case when amounts are less than 0.1, the concentration of the reactants is too high for the reaction to be readily controlled. In the case when the amounts exceed 20, it is not advantageous from the viewpoint of economy for a coating composition.

The phosphatized compound of the present invention is employed in amounts effective to reduce or prevent gassing without adverse effects on application or performance of the coating composition.

Specifically, the phosphatized compound is employed in amounts of about 2 to 30% and preferably about 8 to 20% based on metallic pigments.

In phosphatization, although the charging sequence is not limited, an epoxy compound is preferably charged into the phosphoric acid before the reaction temperature is raised.

The completion of the reaction can be confirmed, for example, by measuring oxirane oxygen with a titration method.

The reaction product obtained can be used as a component for a water-based coating composition as is.

Furthermore, the phosphatized compound of the present invention can be used by distilling low-boiling-point ingredients after water washing or without.

Still further, a further purified phosphatized compound of the present invention can be obtained by reprecipitation with a bad solvent.

In the following, Examples are illustrated in order to describe the present invention in more detail.

EXAMPLE 1

A mixture composed of 40.0 g of a 4-functional alicyclic epoxy resin having an epoxy equivalent of 280 (Epolead GT403 having a viscosity of 700 cp/70° C., water content of 0.05% and acid value of 0.2, manufactured by Daicel Chemical Industries, Ltd.) and 40 g of propyleneglycol monopropylether was charged by dropwise addition into a solution composed of 18.5 g of phosphoric acid(a mixture composed of 100 g of 85% phosphoric acid and 40 g of P$_2$O$_5$) and 26.0 g of propyleneglycol monopropylether over approximately 1 hour.

Reaction temperature exothermally rose to 90° C. or so.

After completion of the exothermic reaction, the temperature was maintained at 90° C. by heating for approximately 2 hours to obtain a reaction crude solution. Oxirane oxygen concentration of the crude reaction solution was measured after cooled to obtain the value of 0, whereby it was confirmed that all of epoxy groups were reacted with phosphoric acid. An acid value of the crude reaction solution was 191.

Figure 5:
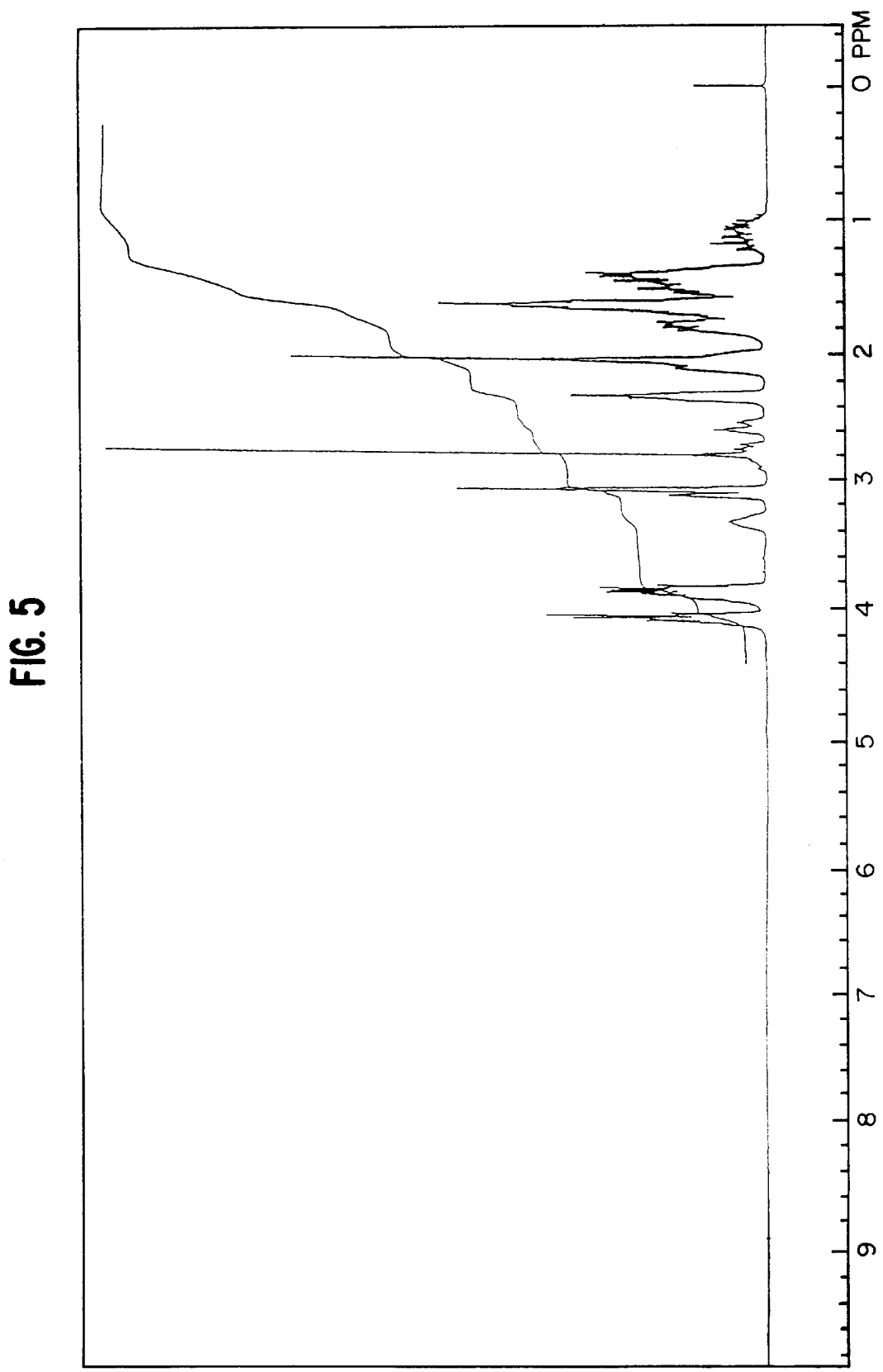
FIG. 5 is an $H^1$-NMR chart related to the starting epoxy compound Example 1.
Figure 6:
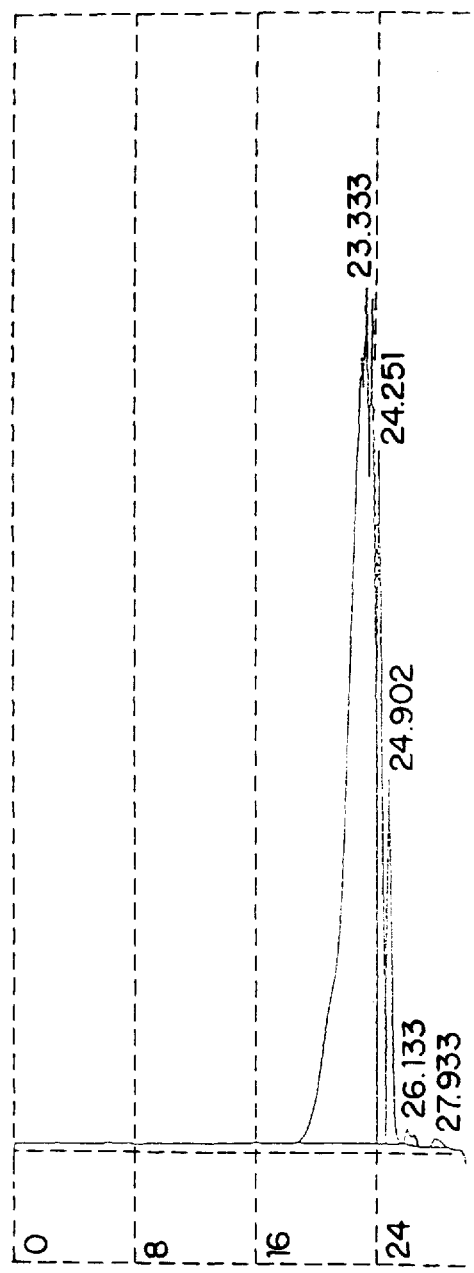
FIG. 6 is a Gel Permeation Chromatography(GPC) chart related to the starting epoxy compound in Example 1.
Figure 7:
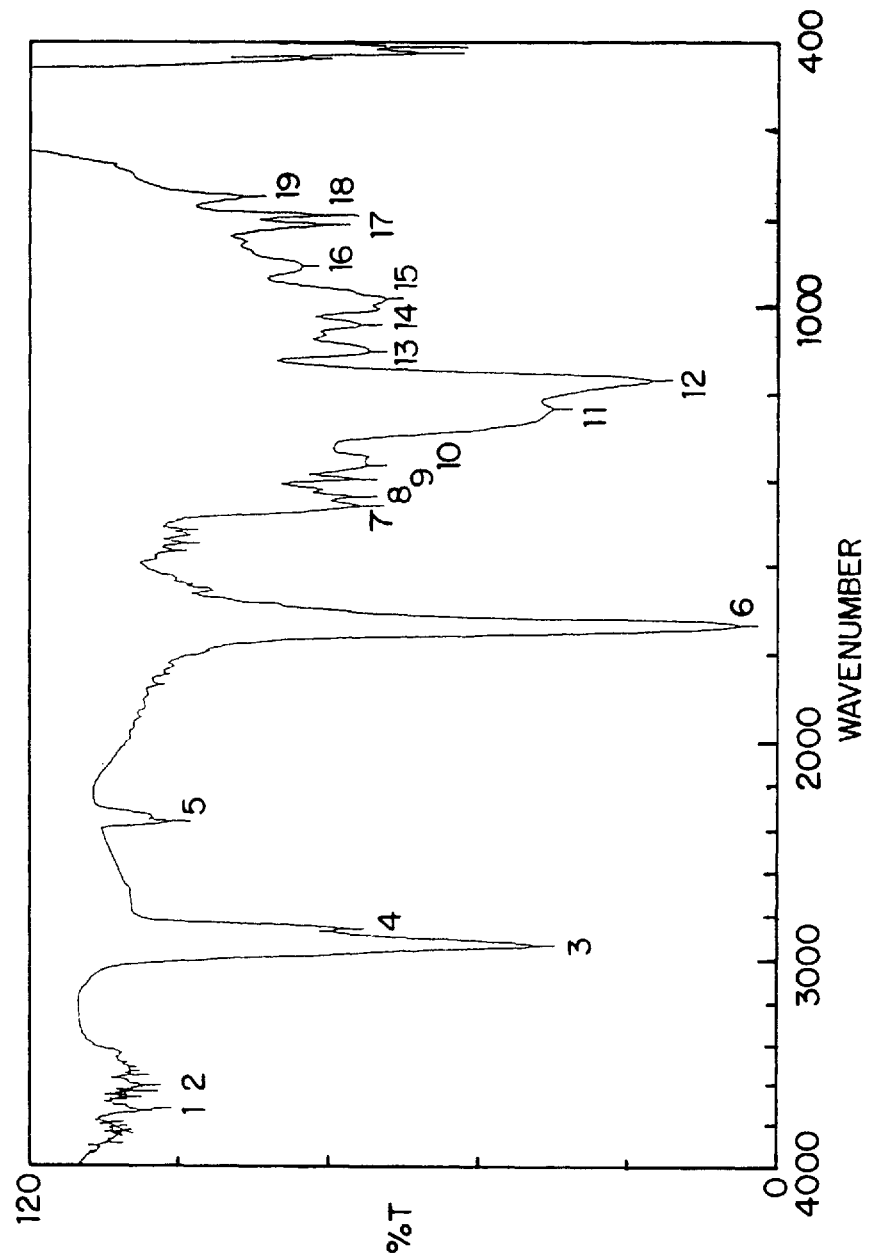
FIG. 7 is an IR spectra chart related to the starting epoxy compound in Example 1.
Figure 8:
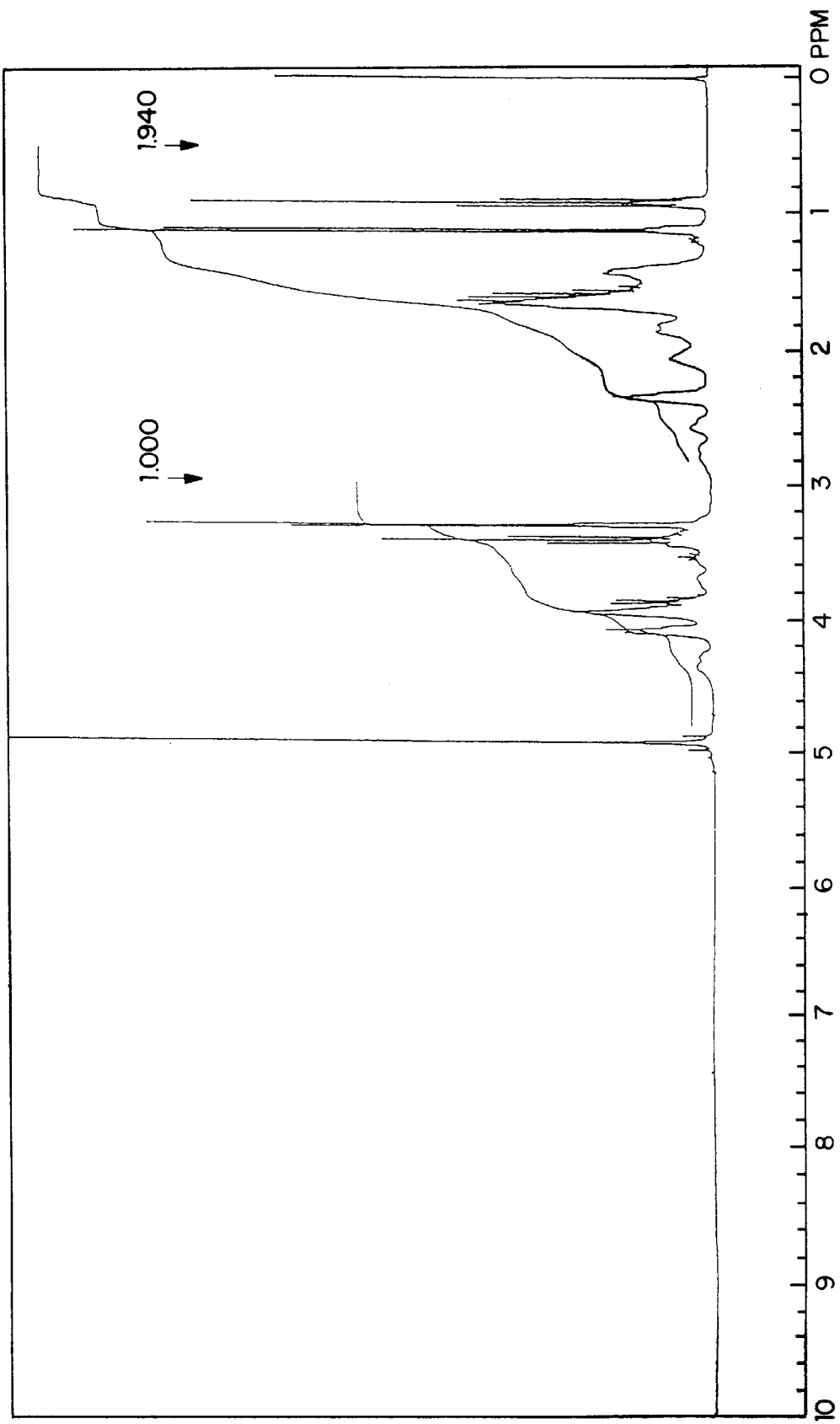
FIG. 8 is an $H^1$-NMR chart related to the phosphatized compound obtained in Example 1.
Figure 9:
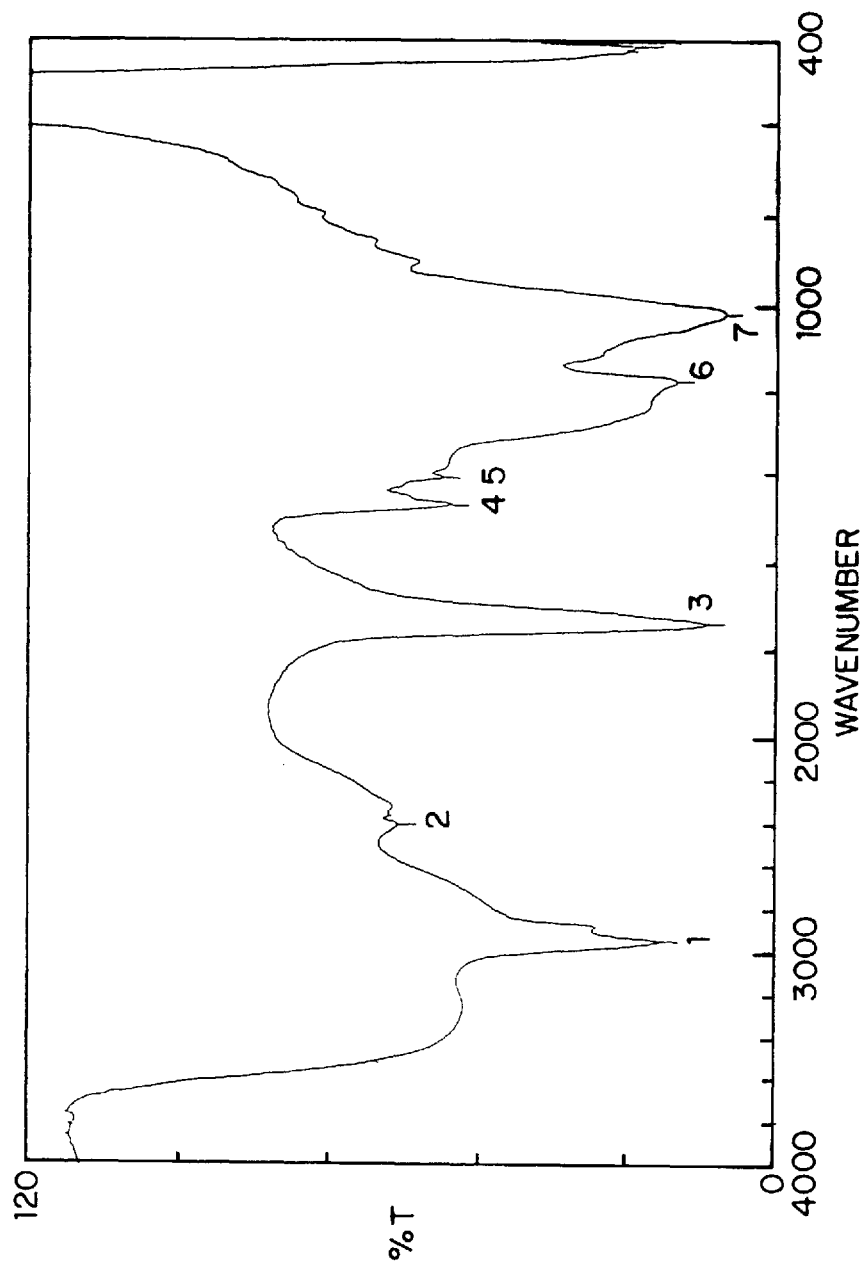
FIG. 9 is an IR spectra chart related to the phosphatized compound obtained in Example 1.
Figure 10:
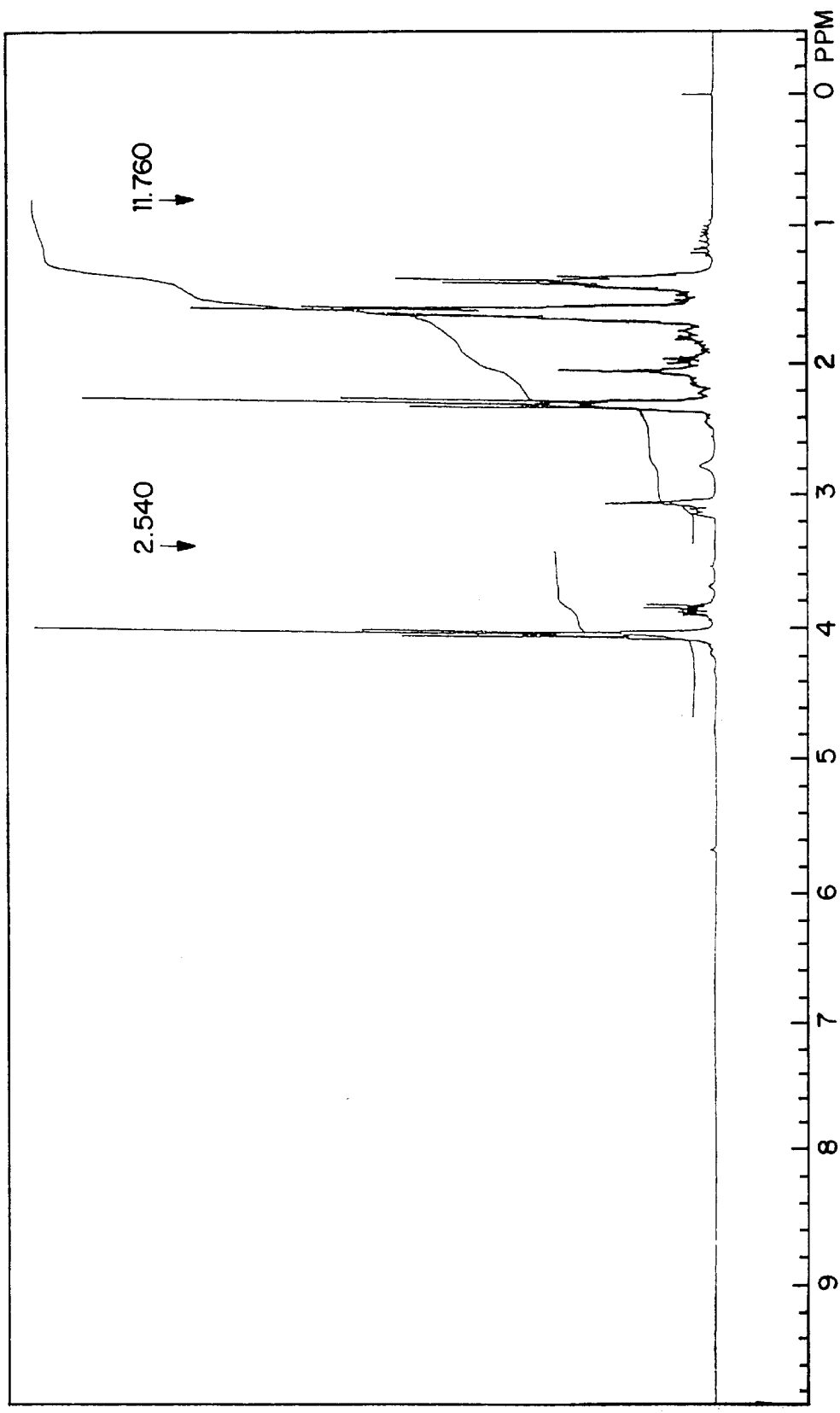
FIG. 10 is an $H^1$-NMR chart related to the starting epoxy compound in Example 4.
Figure 11:
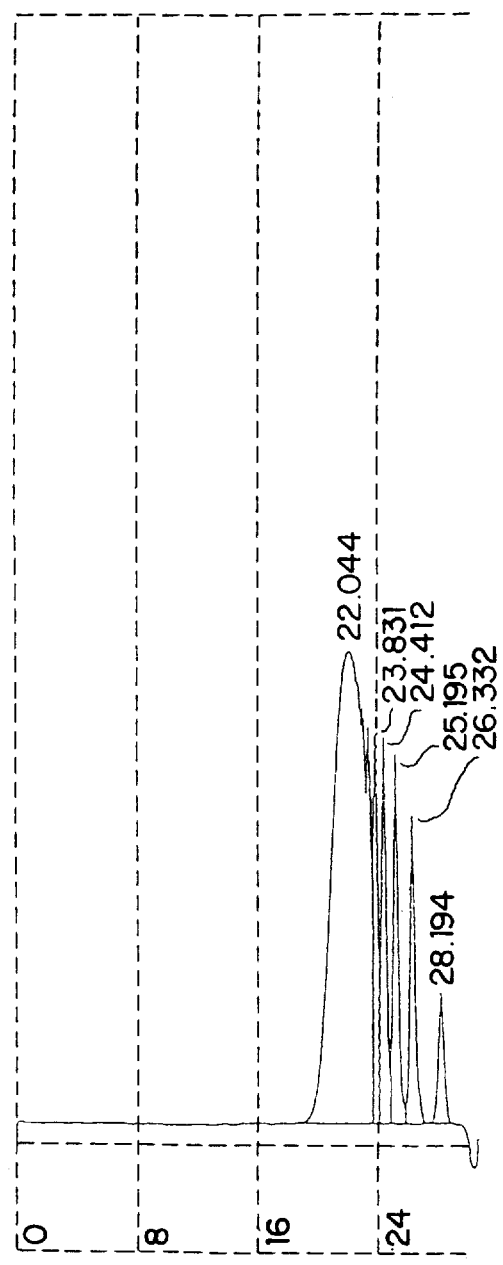
FIG. 11 is a GPC chart related to the starting epoxy compound in Example 4.
Figure 12:
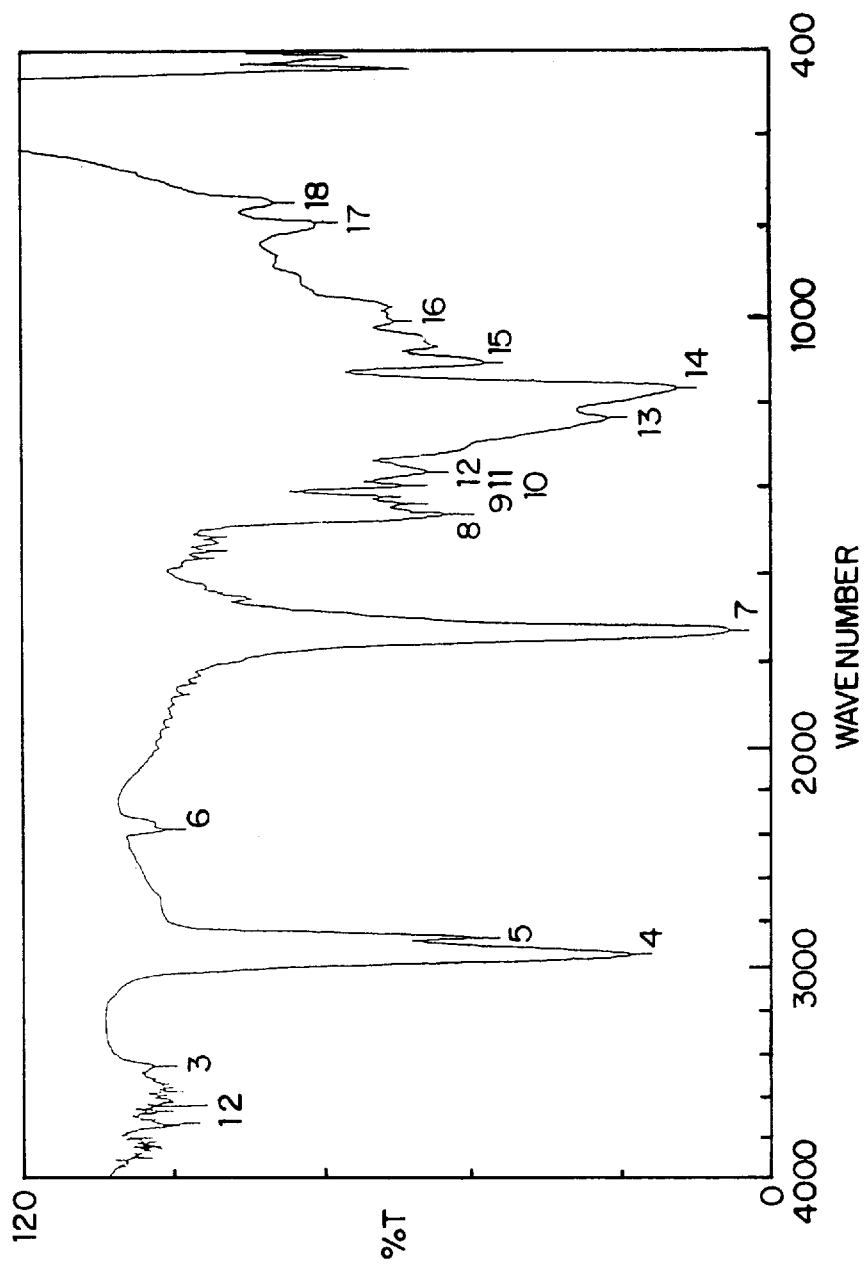
FIG. 12 is an IR spectra chart related to the starting epoxy compound in Example 4.
Figure 13:
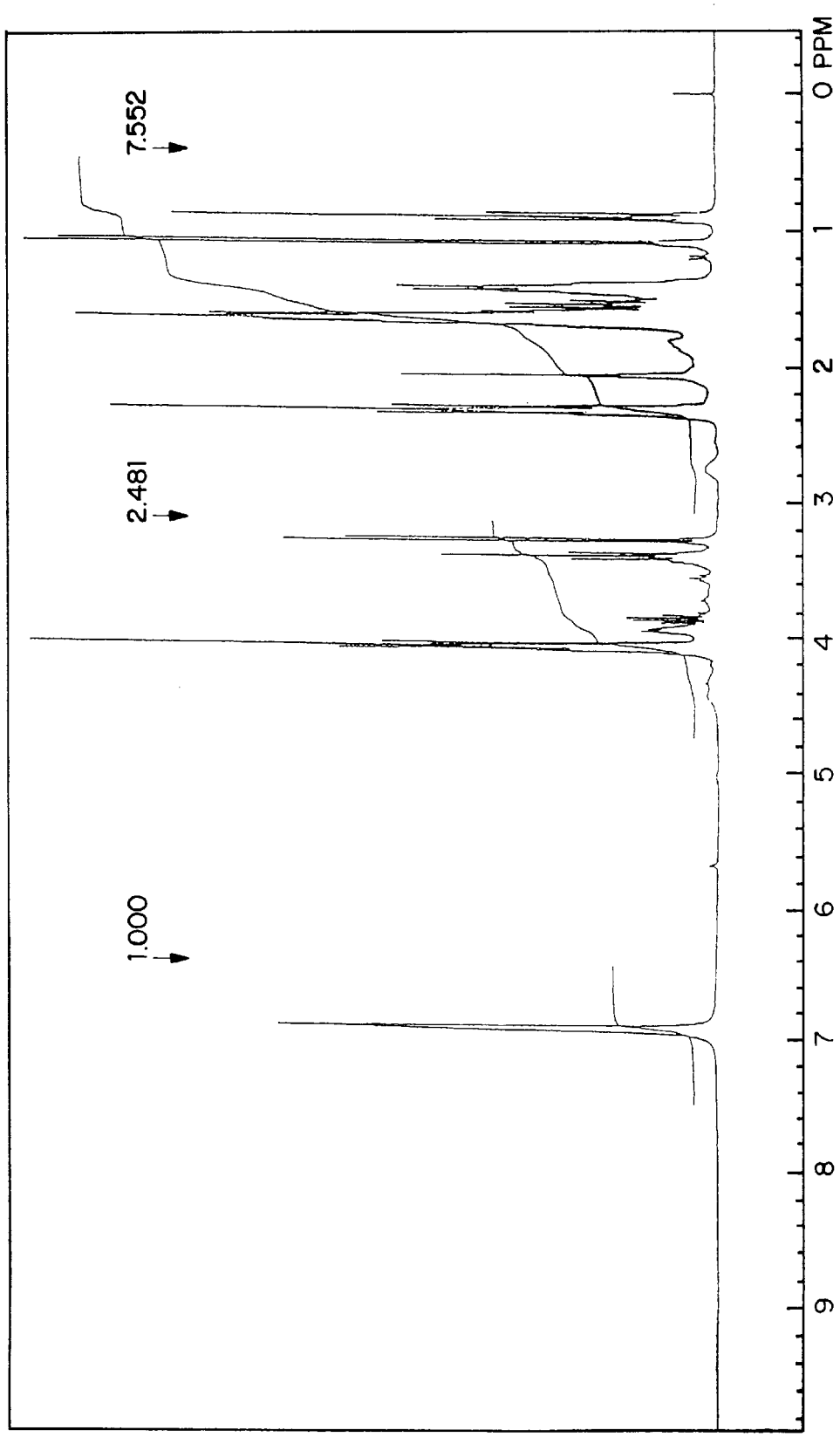
FIG. 13 is an $H^1$-NMR chart related to the phosphatized compound obtained in Example 4.
Figure 14:
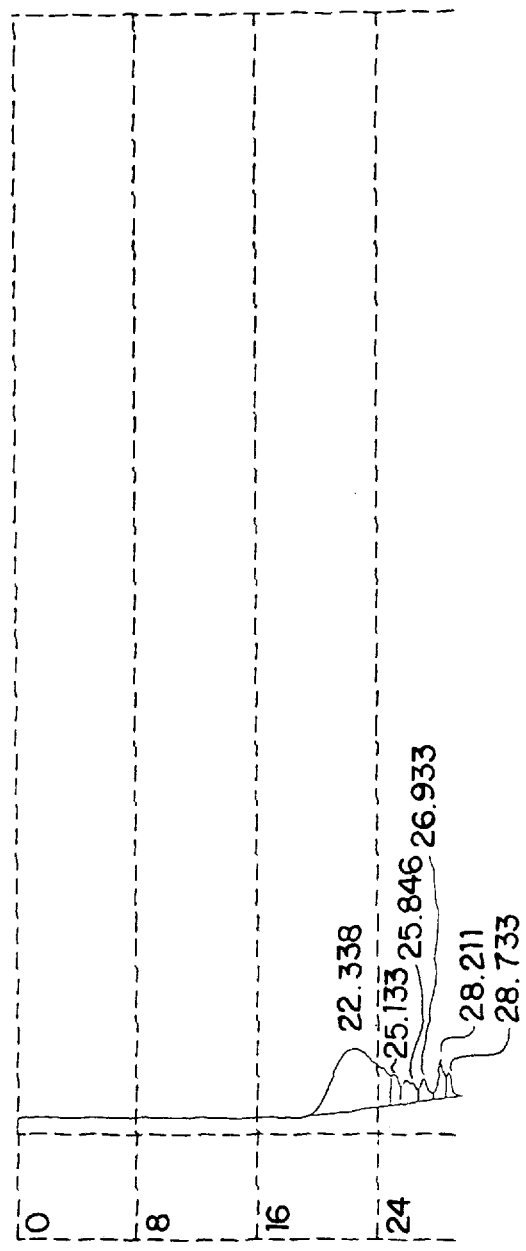
FIG. 14 is a GPC chart related to the phosphatized compound obtained in Example 4.
Figure 15:
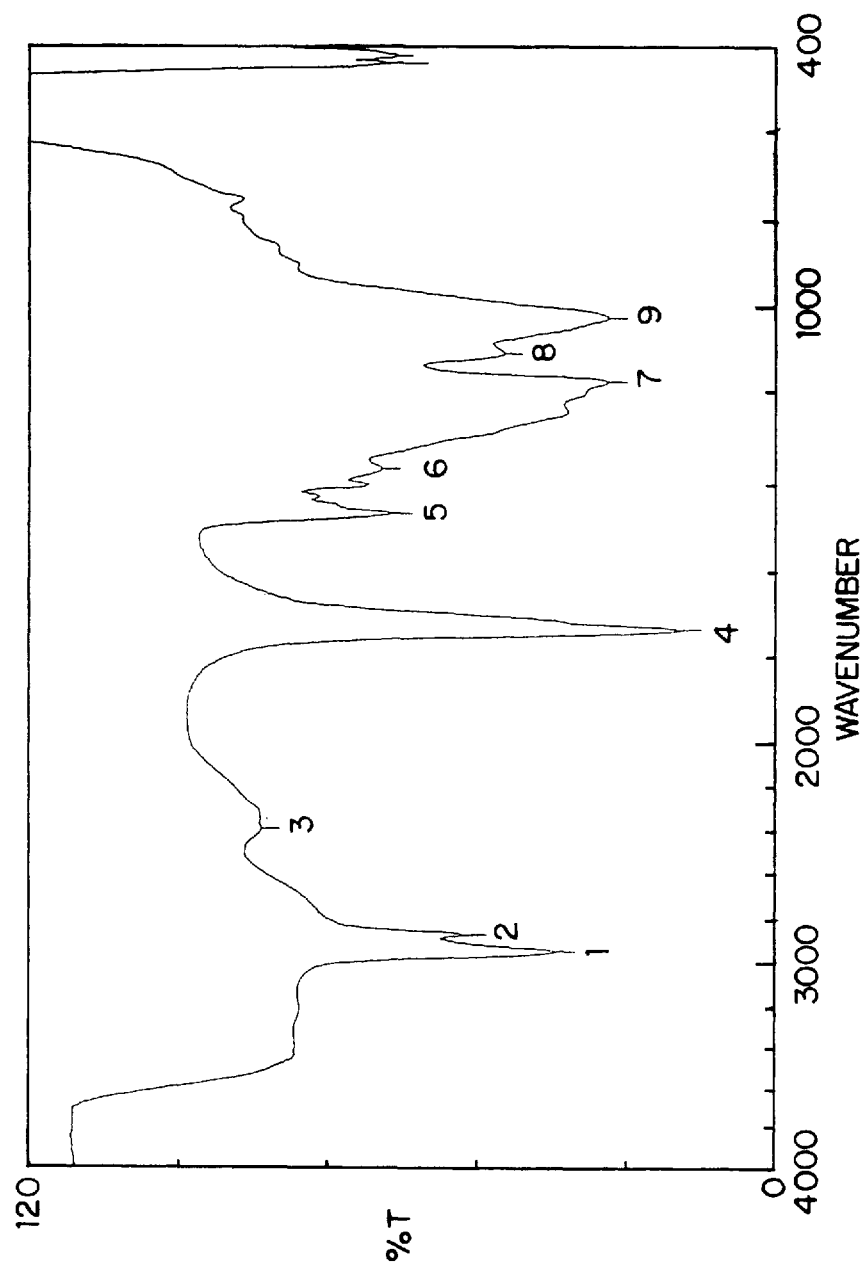
FIG. 15 is an IR spectra chart related to the phosphatized compound obtained in Example 4.
Figure 22:
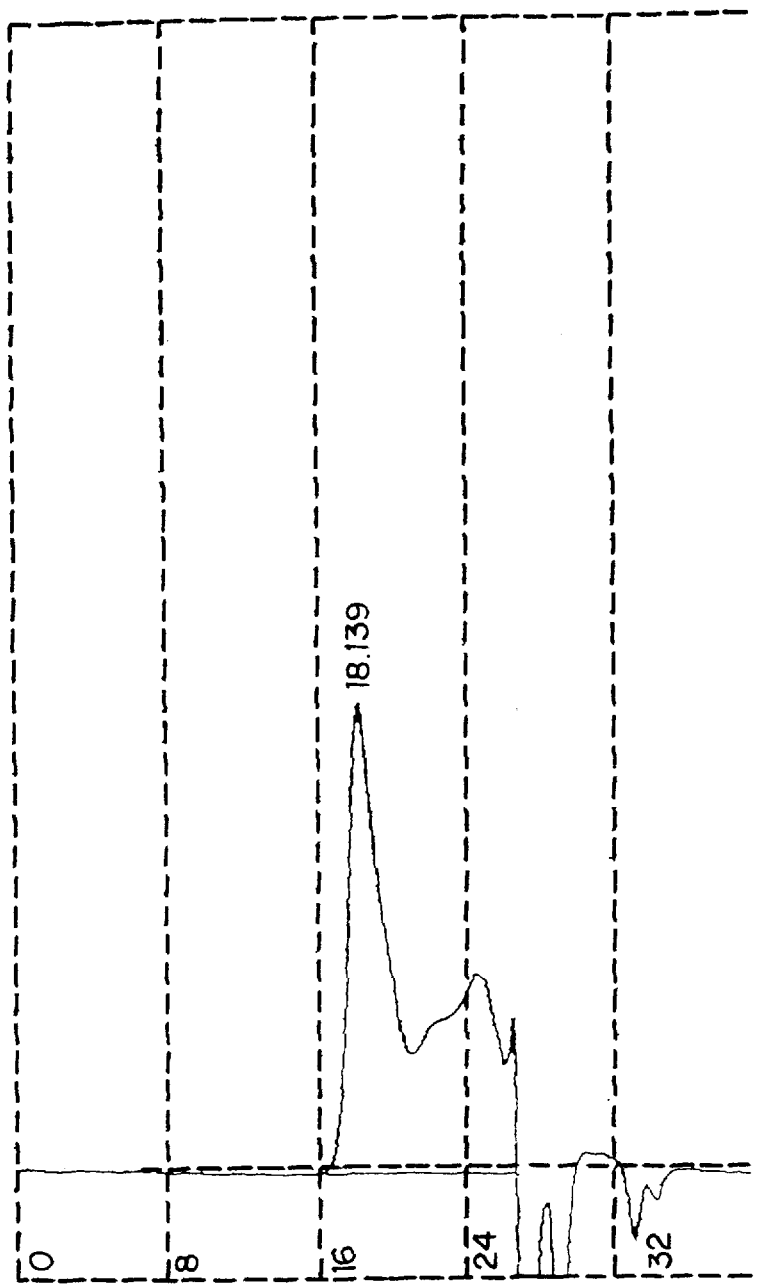
FIG. 22 is a GPC chart related to the starting epoxy compound in Example 1.

NMR, GPC and IR spectrum analyses were carried out in relation to the starting epoxy resin and the phosphatized product. FIGS. 5, 6 and 7 are an NMR chart, a GPC chart and an IR chart in relation to the starting epoxy resin, respectively. FIGS. 8, 9 and 22 are an NMR chart, an IR chart and a GPC chart in relation to the phosphatized product, respectively.

It was confirmed that a weight average molecular weight (Mw) is 21903, a number average molecular weight (Mn) is 2077 and Mw/Mn is 10.55.

EXAMPLE 2

A mixture composed of 40 g of a 2-functional alicyclic epoxy resin having an epoxy equivalent of 350(Celloxide 2083 having a viscosity of 150 cp/45° C., water content of 0.05% and the specific gravity of 1.13 (20° C./20° C.), manufactured by Daicel Chemical Industries, Ltd.) and 40 g of propyleneglycol monopropylether was charged by dropwise addition into a solution composed of 18.48 g of the phosphoric acid and 40 g of propyleneglycol monopropylether over approximately 1 hour.

Reaction temperature exothermally rose to 90° C. or so.

After completion of the exothermic reaction, the temperature was maintained at 90° C. by heating for approximately 2 hours to obtain a reaction crude solution. Oxirane oxygen concentration of the crude reaction solution was measured after cooled to obtain the value of 0, whereby it was confirmed that all of epoxy groups are reacted with the phosphoric acid. An acid value of the crude reaction solution was 183.

Figure 16:
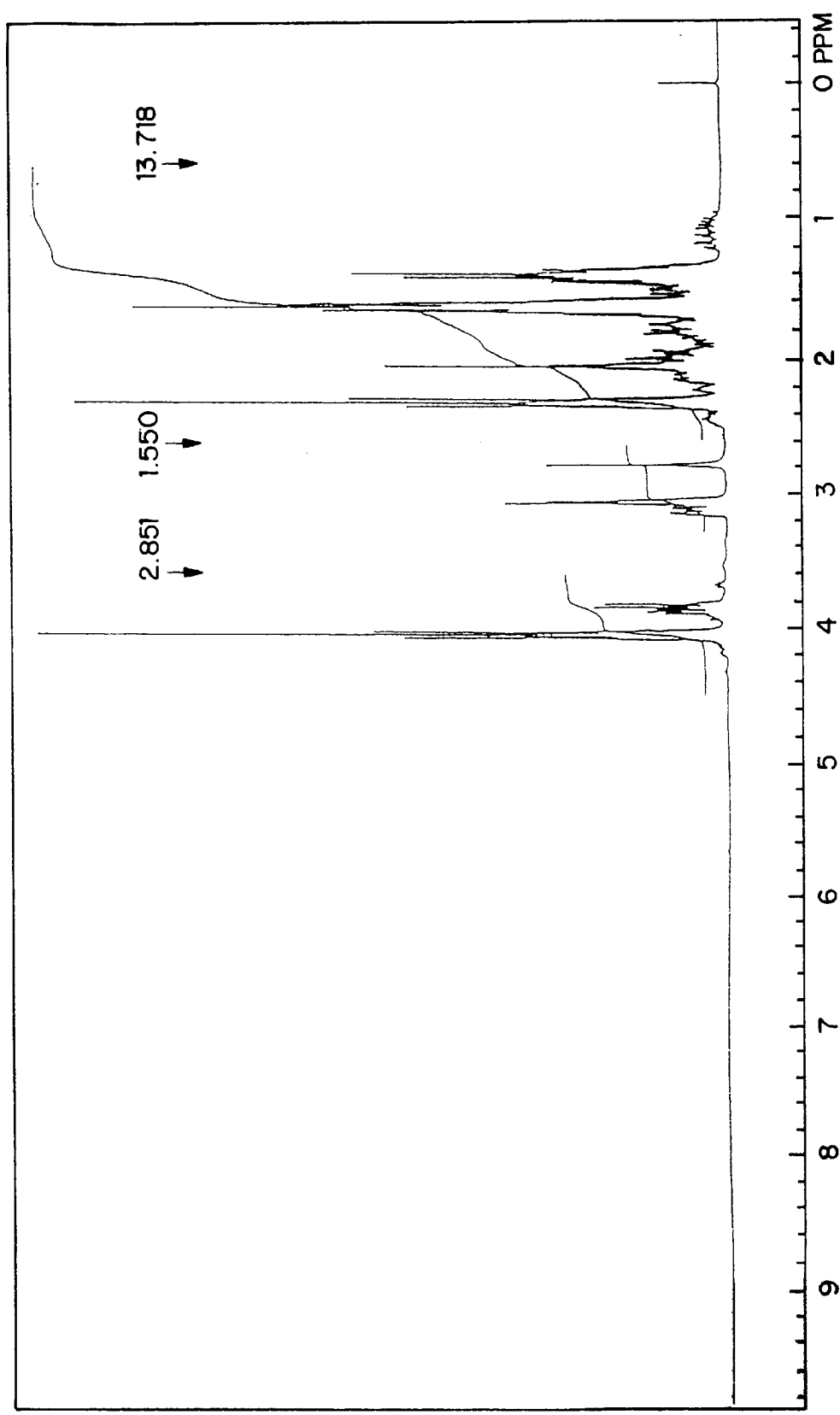
FIG. 16 is an $H^1$-NMR chart related to the starting epoxy compound in Example 2.
Figure 17:
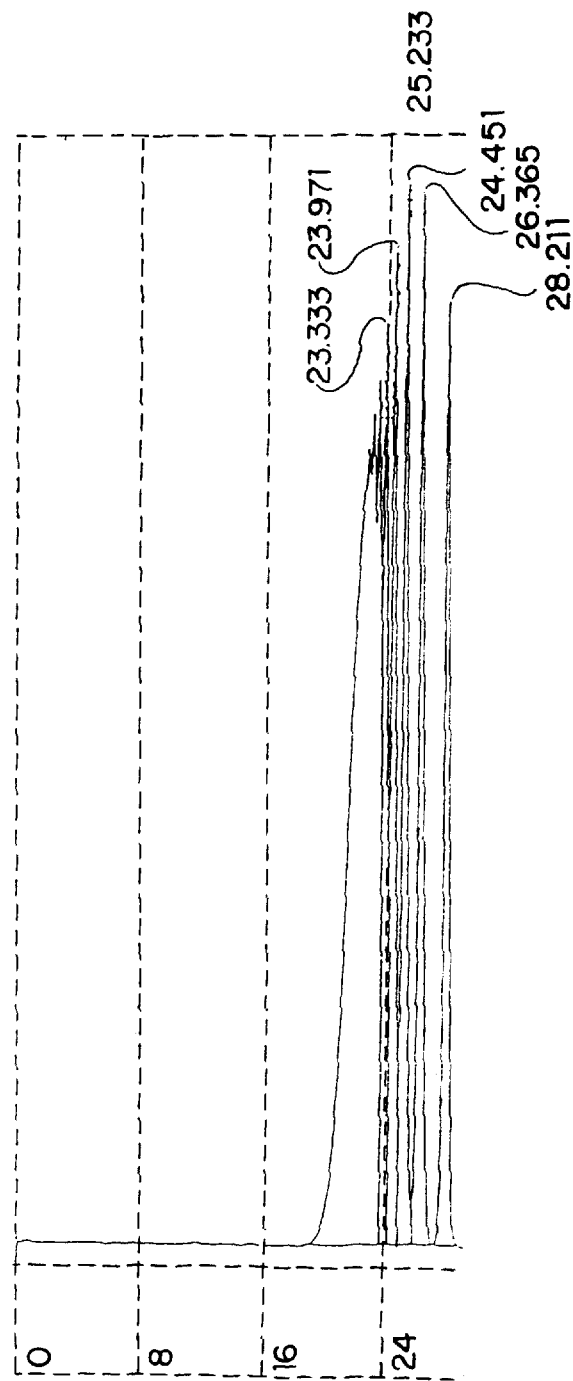
FIG. 17 is a GPC chart related to the starting epoxy compound in Example 2.
Figure 18:
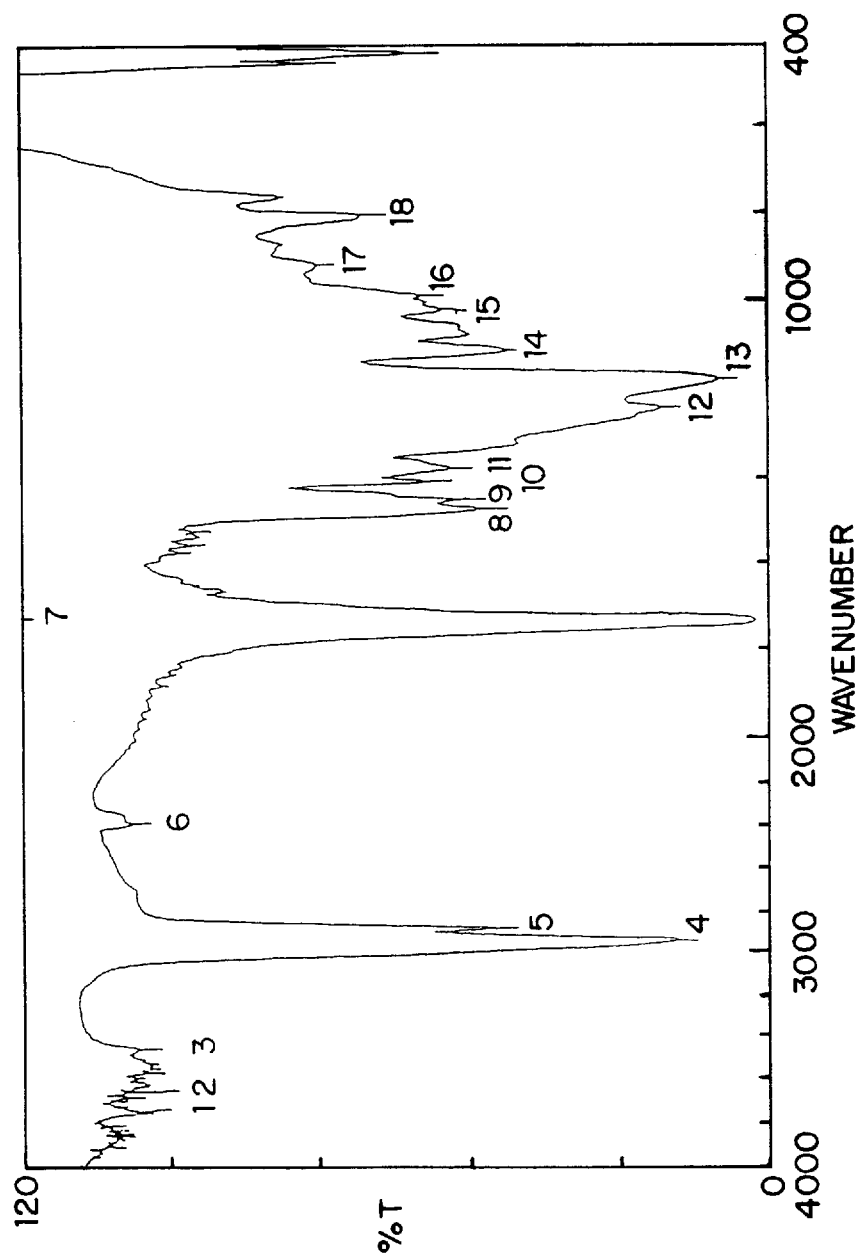
FIG. 18 is an IR spectra chart related to the starting epoxy compound in Example 2.

NMR, GPC and IR spectrum analyses were carried out in relation to the starting epoxy resin and the phosphatized product. FIGS. 16, 17 and 18 are an NMR chart, a GPC chart and an IR chart in relation to the starting epoxy resin, respectively.

Figure 19:
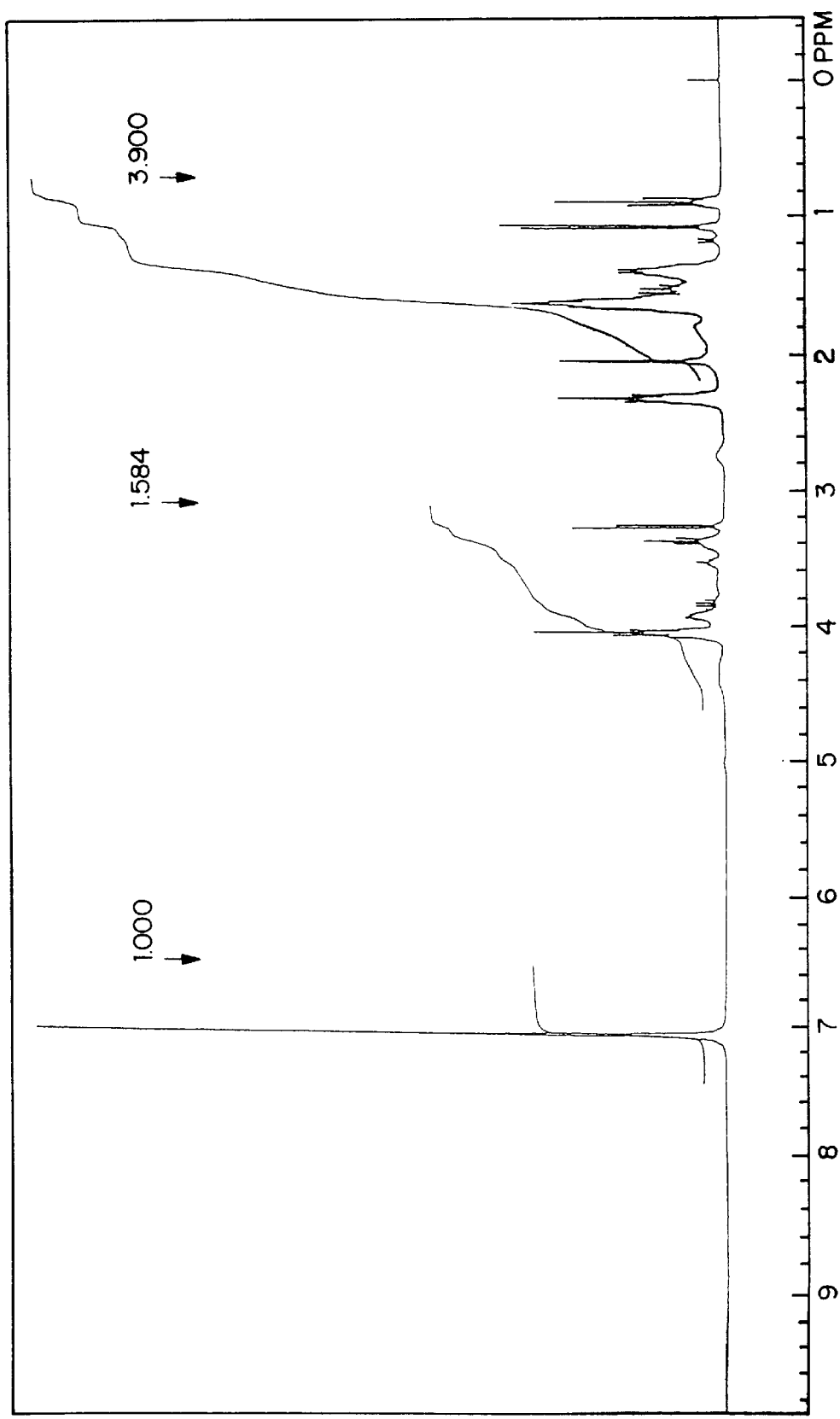
FIG. 19 is an $H^1$-NMR chart related to the phosphatized compound obtained in Example 2.
Figure 20:
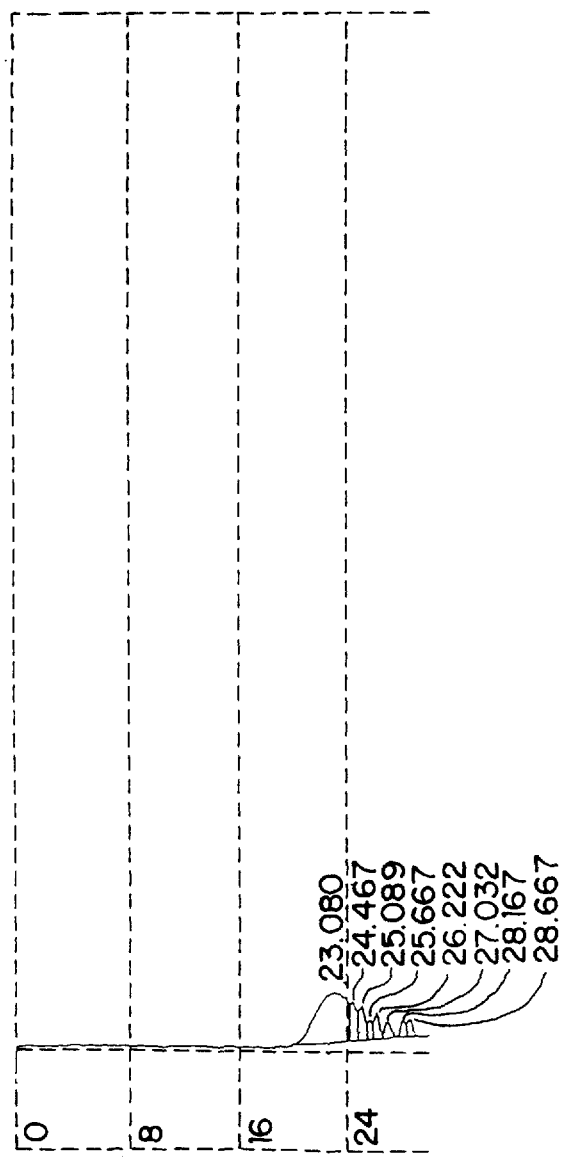
FIG. 20 is a GPC chart related to the phosphatized compound obtained in Example 2.
Figure 21:
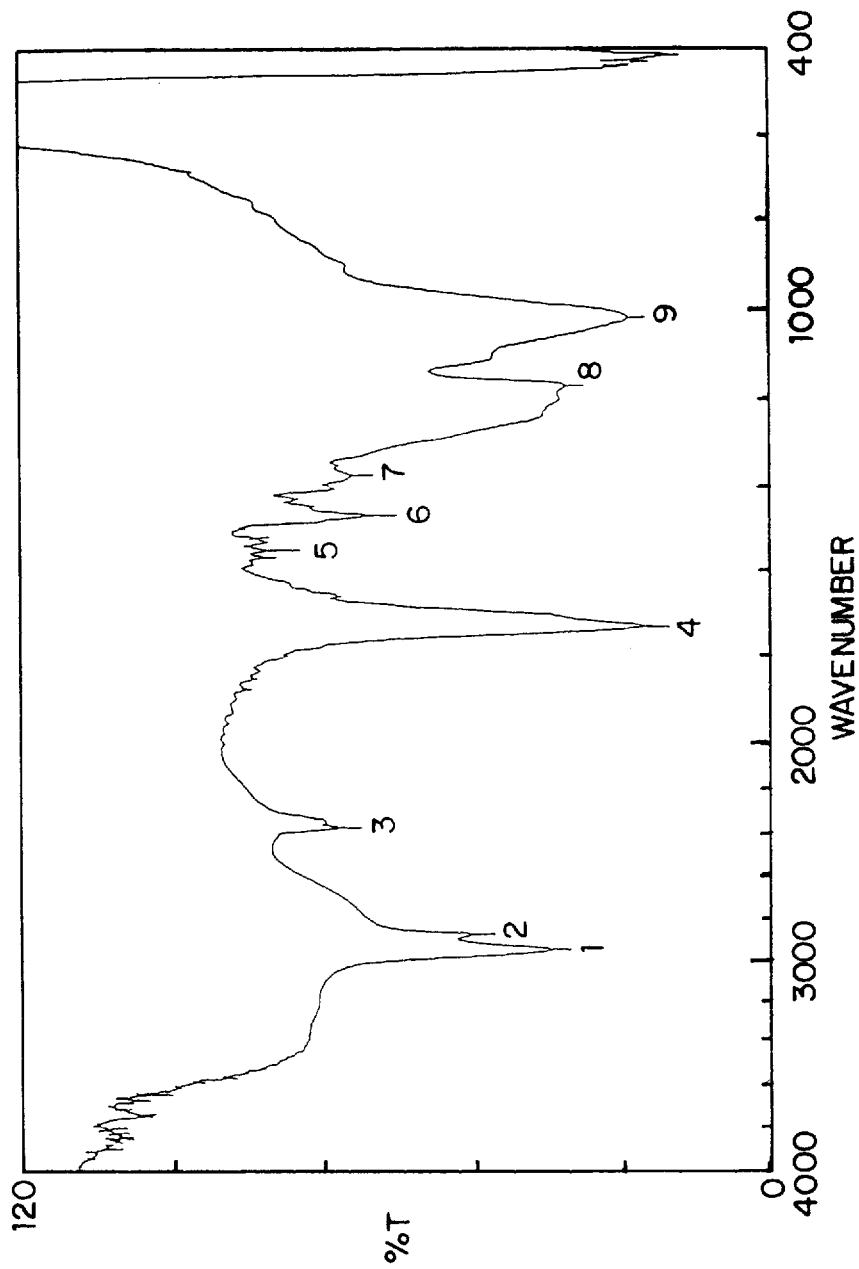
FIG. 21 is an IR spectra chart related to the phosphatized compound obtained in Example 2.

FIGS. 19, 20 and 21 are an NMR chart, a GPC chart and an IR spectra chart in relation to the phosphatized product, respectively.

EXAMPLES 3 to 8

Same procedures as described in Example 1 were repeated, except that starting epoxy resins as described in Table 1 were employed to obtain phosphatized compounds. The amount of the starting epoxy resins is 40.0 g, and 40.0 g of propyleneglycol monopropylether and 40 g of the phosphoric acid were employed as a solvent and a compound having the —OP(=O)(OH)$_2$ group in all the Examples, respectively.

Results are also shown in Table 1.

TABLE 1

| | Example | | | | | |
|---|---|---|---|---|---|---|
| | 3 | 4 | 5 | 6 | 7 | 8 |
| Epoxy resin | A | B | C | D | E | F |
| Epoxy equivalent | 210 | 490 | 150 | 240 | 190 | 220 |
| Viscosity(cp/°C.) | 110/45 | 410/45 | 200/70 | 200/70 | 10000/70 | 2000/70 |
| Acid value(mg KOH/g) | 0.5 | 0.1 | 0.2 | 0.2 | 0.3 | 0.2 |
| Amount of phosphoric acid(g) | 22.4 | 9.64 | 31.4 | 19.0 | 24.8 | 21.4 |
| Amount of the solvent for mixing phosphoric acid(g) | 20.0 | 20.0 | 30.0 | 20.0 | 20.0 | 20.0 |
| Oxirane oxygen(%) in the crude reaction solution | 0 | 0 | 0 | 0 | 0 | 0 |
| Acid value(mg KOH/g) in the crude reaction solution | 225 | 108.3 | 274.5 | 203.0 | 245.0 | 218.0 |

In the Table 1, Epoxy resins A, B, C, D, E and F are Celloxide 2081, Celloxide 2085, Epolead GT300, Epolead GT400 and Epolead GT401 which are all manufactured by Daicel Chemical Industries, Ltd., respectively.

Characterization of the phosphatized compounds obtained in Examples 2 to 8 was carried out with NMR charts, IR charts and GPC charts.

Results are also shown in Table 2.

TABLE 2

| | NMR | IR | GPC |
|---|---|---|---|
| Example 2 | 3.0–3.2 3.2–3.6 | 1016 cm$^{-1}$ (P-OH) | Mw = 1180, Mn = 539 Mw/Mn = 2.188 |
| Example 3 | 3.0–3.2 3.2–3.6 | 1015 cm$^{-1}$ (P-OH) | Mw = 990, Mn = 501 |
| Example 4 | 3.3–3.5 3.2–3.6 | 1018 cm$^{-1}$ (P-OH) | Mw = 1552, Mn = 523 Mw/Mn = 2.969 |
| Example 5 | 3.1–3.2 3.2–3.5 | 1017 cm$^{-1}$ | |
| Example 6 | 3.1–3.2 3.2–3.5 | 1018 cm$^{-1}$ | |
| Example 7 | 3.0–3.2 3.2–3.5 | 1015 cm$^{-1}$ | |
| Example 7 | 3.0–3.2 3.2–3.5 | 1017 cm$^{-1}$ | |

In the Table 2, arrow marks show a shift of an absorption peak.

EXAMPLE 9

Low-boiling-point ingredients were removed from the crude reaction solution obtained in Example 1 at 80°–100° C. and 2–5 mmHg for 2 hours with a rotary evaporator. IR spectra in relation to the starting epoxy compound changed from the FIG. 1 to FIG. 2.

Figure 2:
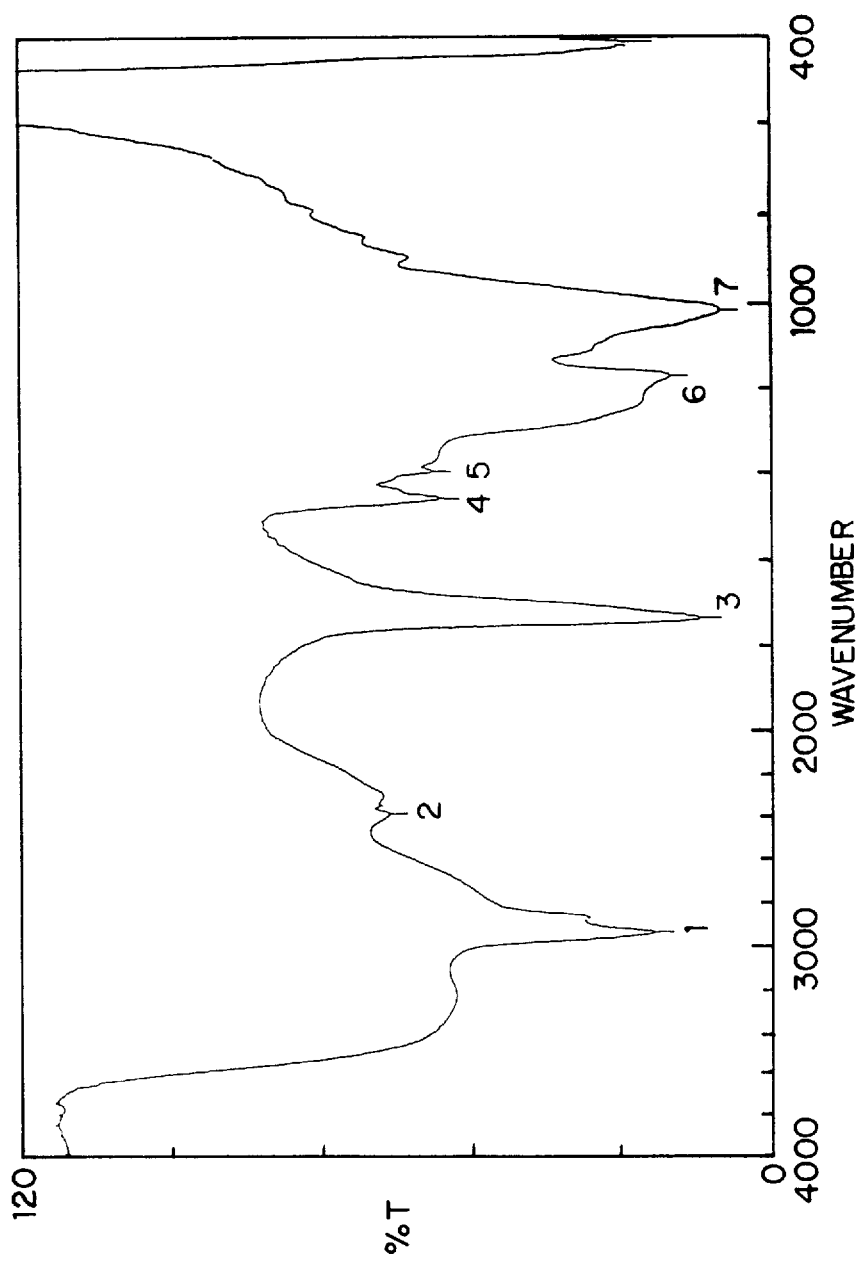
FIG. 2 is an IR spectra chart related to the phosphatized compound obtained in Example 1.

FIG. 2 shows that there appear absorption peaks by P-O observed at 1010 cm$^{-1}$ and 1014 cm$^{-1}$, and there disappear absorption peaks by epoxy groups observed at 780–820 cm$^{-1}$ and 800–940 cm$^{-1}$.

Figure 3:
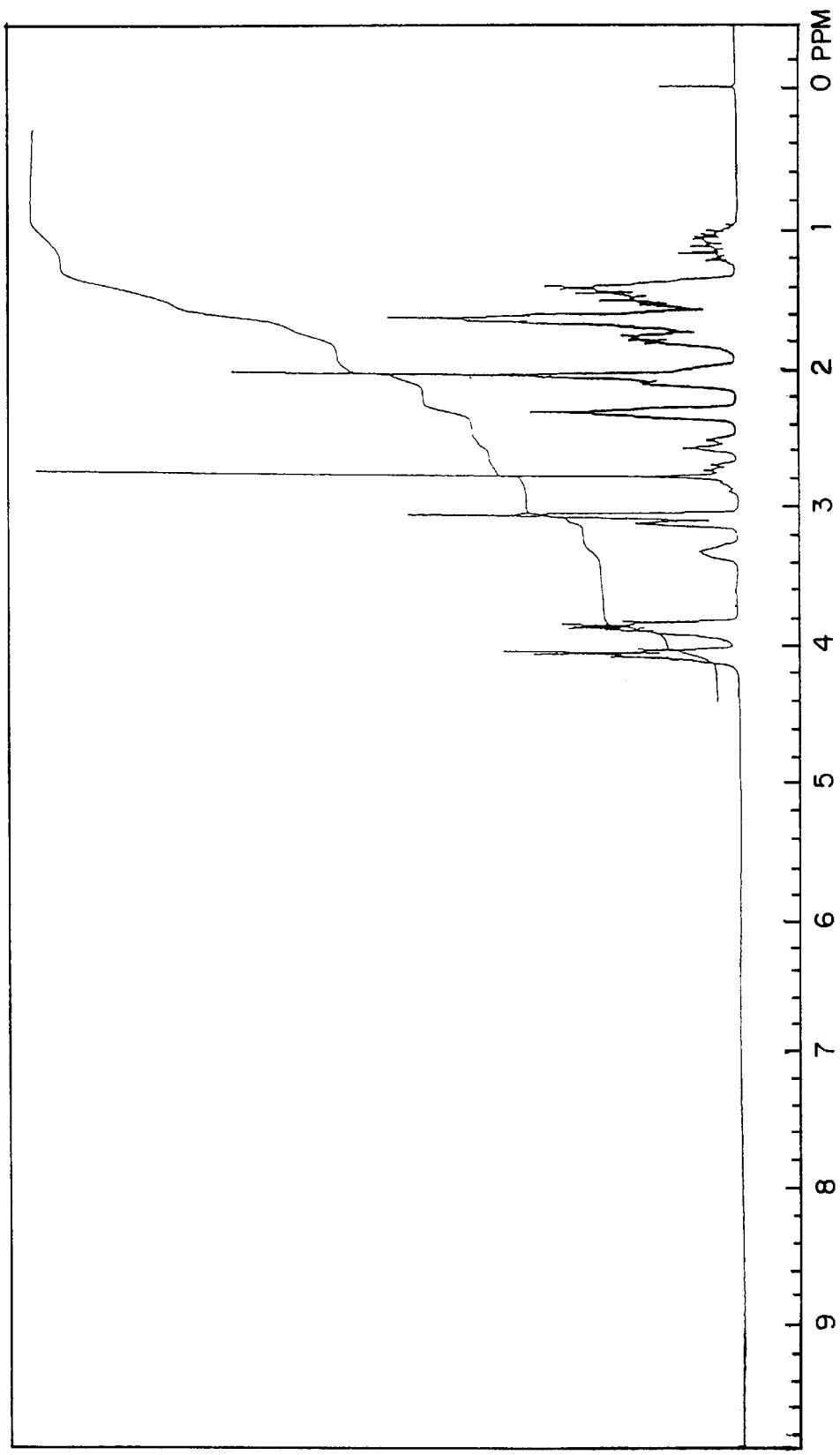
FIG. 3 is a Nuclear Magnetic Resonance($H^1$-NMR) chart related to the starting epoxy compound in Example 1.
Figure 4:
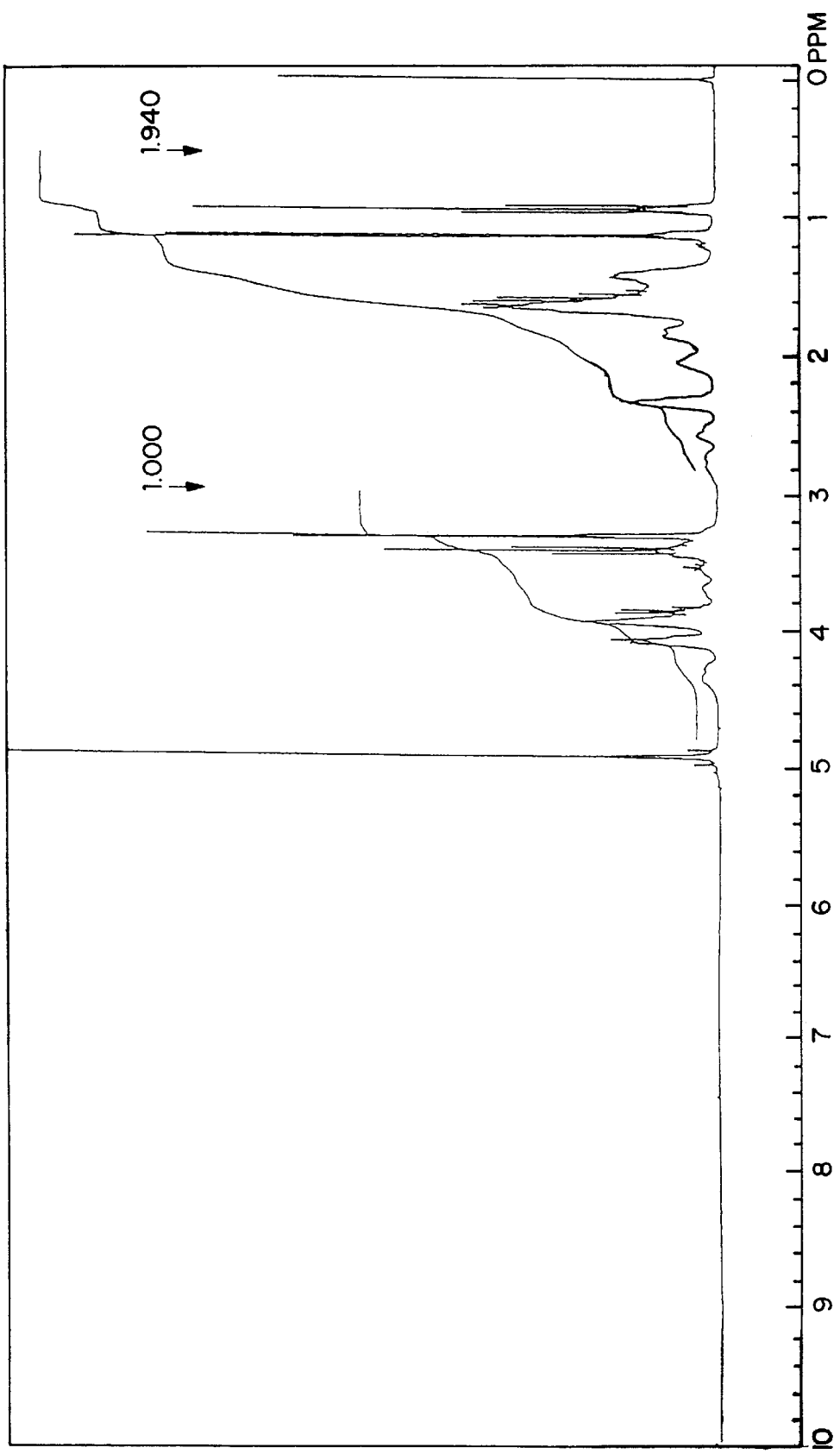
FIG. 4 is an $H^1$-NMR chart related to the Phosphatized compound obtained in Example 1.

By the H-NMR charts, it was confirmed that a peak at 3.0–3.4 ppm(shown in FIG. 3) by a proton adjacent to an epoxy group shifted to a peak at 3.3–3.6 ppm(shown in FIG. 4) which is a peak in low magnetic field, resulting in showing the opening of epoxy groups.

It was confirmed by the above-mentioned analyses that the compositions obtained in Examples 1 to 8 are primarily composed of the compounds represented by the formulae as described below, respectively.

[Composition obtained in Example 1/a+b+c+d=3]

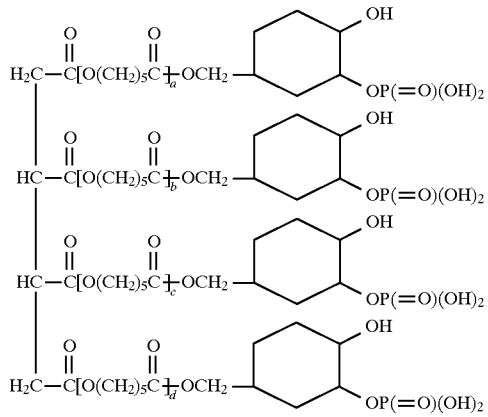

[Composition obtained in Example 2]

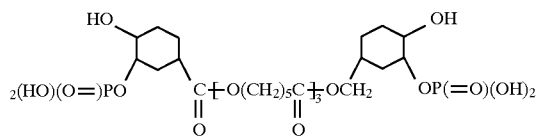

[Composition obtained in Example 3]

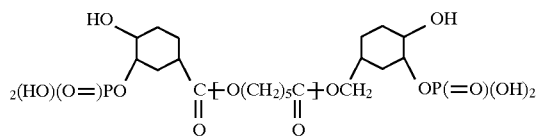

[Composition obtained in Example 4]

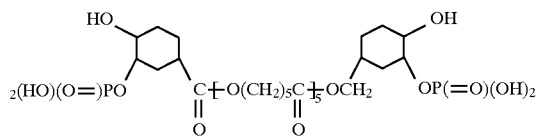

[Composition obtained in Example 5/a+b=0]

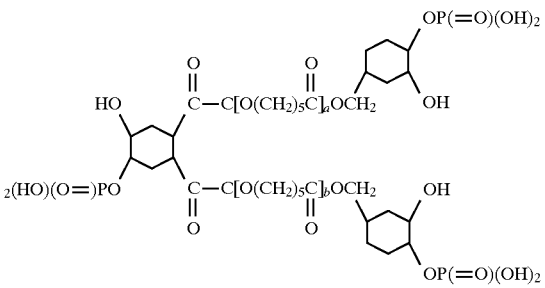

[Composition obtained in Example 6/a+b=2]

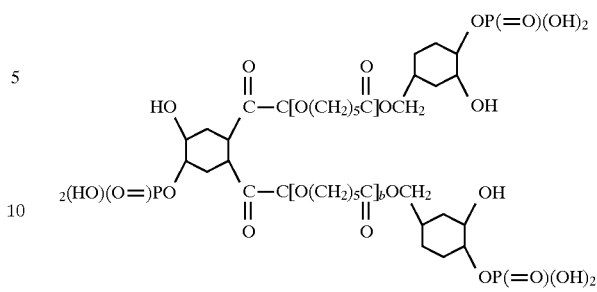

[Composition obtained in Example 7/a+b+c+d=0]

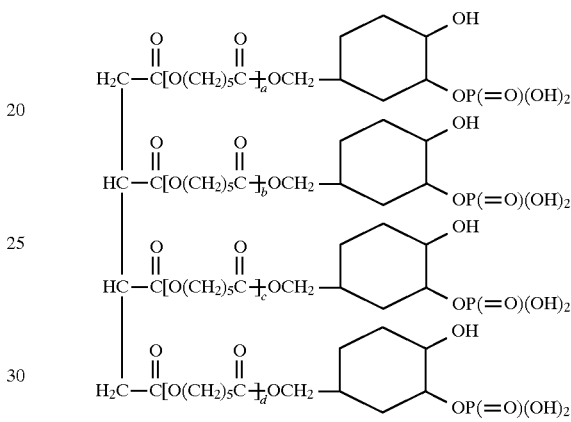

[Composition obtained in Example 8/a+b+c+d=1]

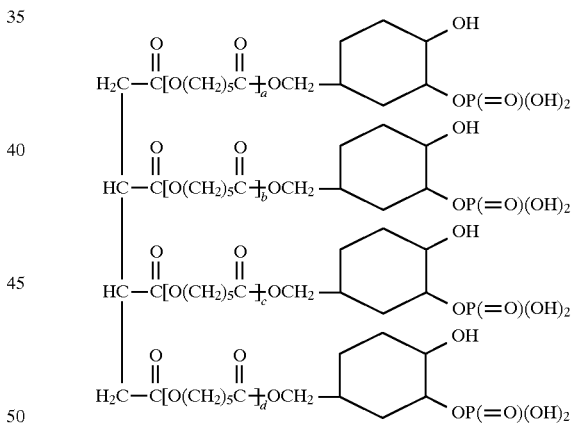

It is noted in the Examples that GXS270WB or JNM-EX270(solvent/dichloroform or dimethanol) manufactured by Nihon Denshi, Ltd. was used in NMR analyses, FT/IR-5300 manufactured by Nihon Bunko Ltd. was used in an IR analyses, and HPLC LC-6A(column/Polystyrene column, solvent/THF) manufactured by Shimadzu Seisakusyo, Ltd. was used in GPC analyses.

EXAMPLE 10

35.7 g of an alicyclic epoxy resin disclosed in U.S. Pat. No. 4,565,859 or EP Publication No. 85100950 (EHPE 3150 manufactured by Daicel Chemical Industries, Ltd.) was dissolved in 35.7 g of methylethylketone, and then 142.8 g of propyleneglycol monopropylether was charged to obtain a homogeneous solution.

24.7 g of phosphoric acid was charged into a flask having 500 ml, and then the homogeneous solution obtained hereinabove was charged into the flask by dropwise addition over 1 hour. Temperature was maintained at 90° C. over approximately 2 hours after the completion of the exothermic reaction to obtain a crude phosphatized composition.

Oxirane oxygen concentration and an acid value relating to the crude phosphatized composition were measured to obtain the value of 0 and 145 after cooled, respectively.

IR and NMR analyses were carried out relating to the starting epoxy resin and the phosphatized composition obtained.

Figure 23:
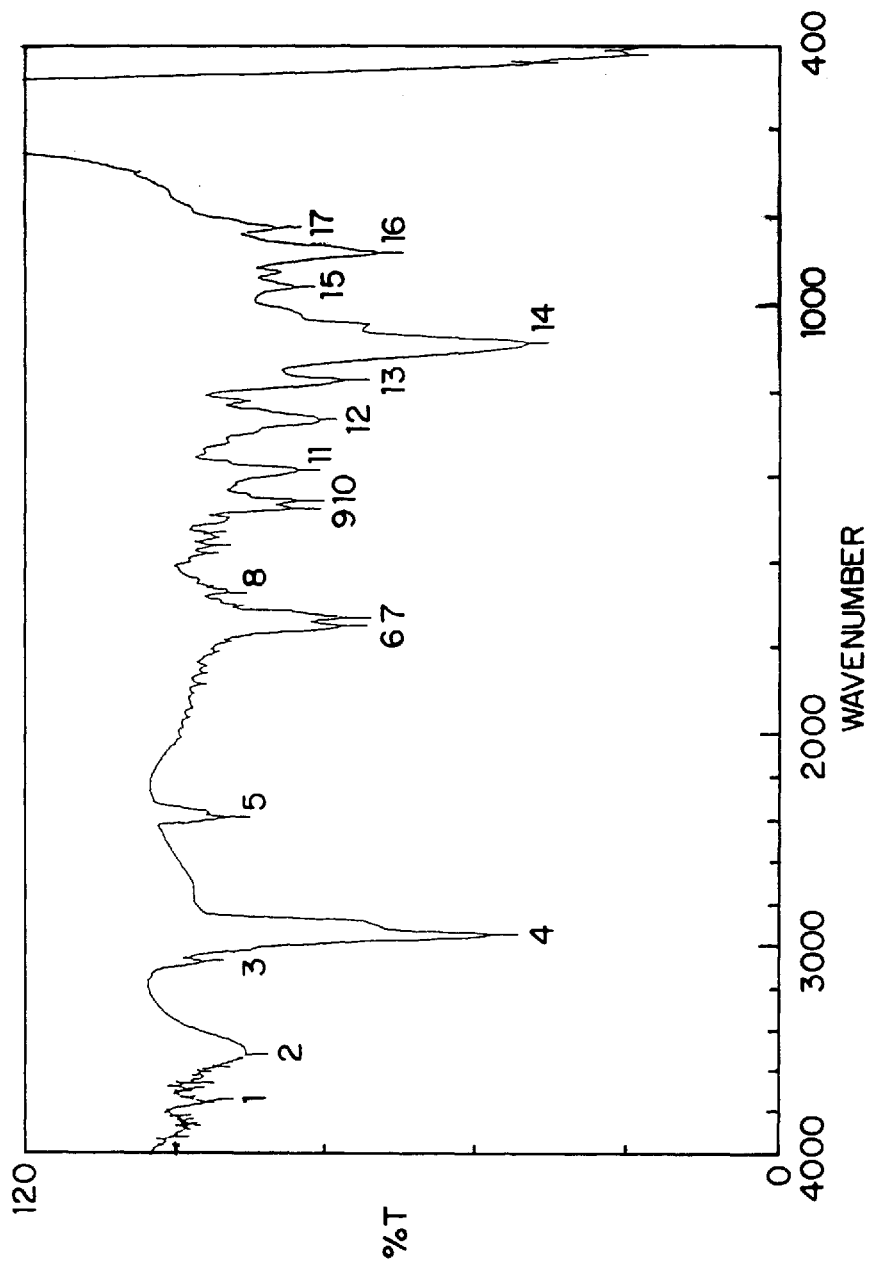
FIG. 23 is an IR spectra chart related to the starting epoxy compound [EHPE 3150] in Example 10.
Figure 24:
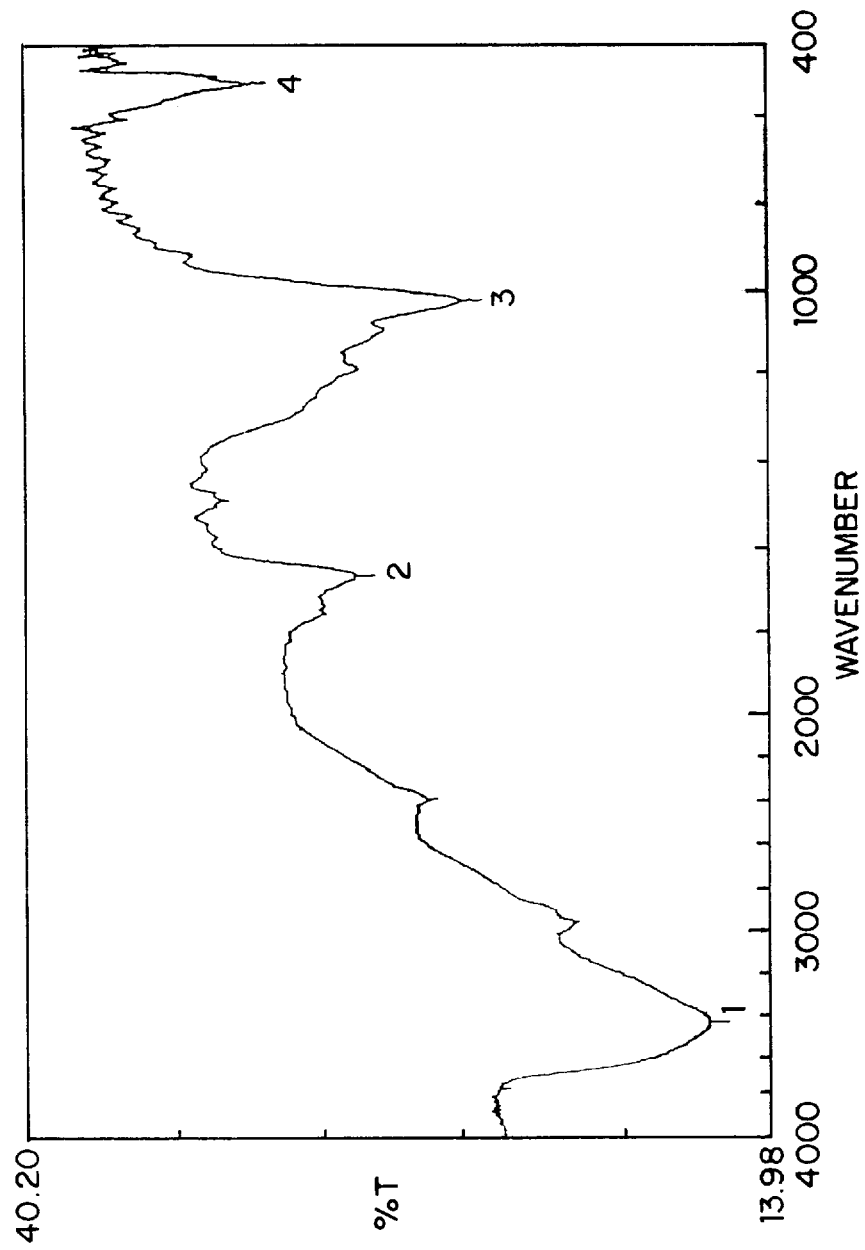
FIG. 24 is an IR spectra chart related to the phosphatized compound obtained in Example 10.

Successively, low-boiling-point ingredients were removed from the crude phosphatized composition obtained at 80°–100° C. and 2–5 mmHg for 2 hours with a rotary evaporator. IR spectra changed from the FIG. 23 in relation to the starting epoxy compound to FIG. 24 in relation to the phosphatized compound.

It is noted that JNM-GXS270 (6.34T, $^{13}$C, 67.8 MHz) manufactured by Nihon Denshi, Ltd. was used in NMR analyses (a measurement method: CP-MAS, a contact time: 1.0 micro second, pausing time of a pulse: 5 seconds, spinning; 4.75 KHz).

Furthermore, although NMR analyses were carried out, the compound did not dissolve in dichloroform, etc.

Figure 26:
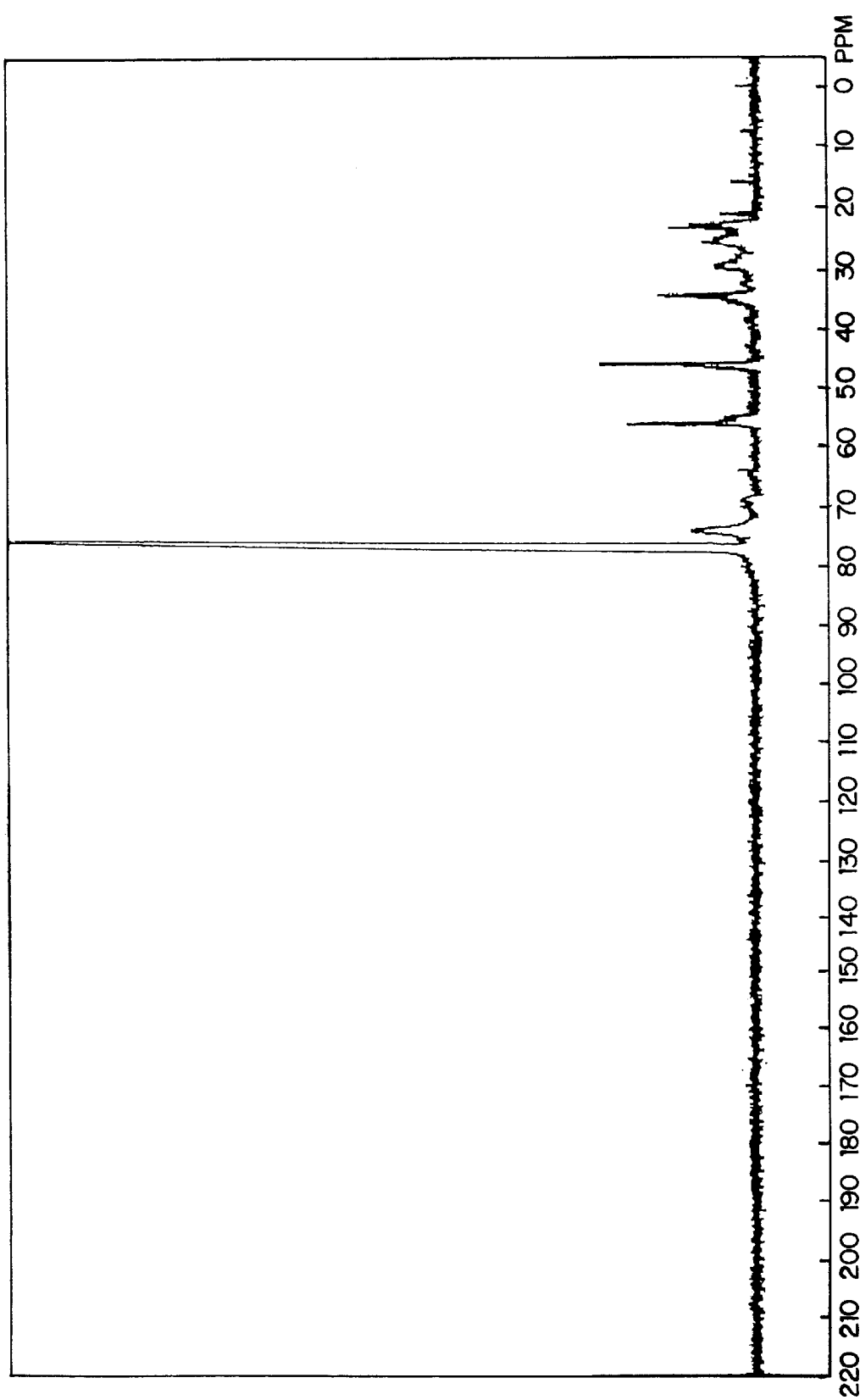
FIG. 26 is an $C^{13}$-NMR chart related to the phosphatized compound obtained in Example 10.

Accordingly, it was compared with $^{13}$C-NMR chart as shown in FIG. 26.

Figure 25:
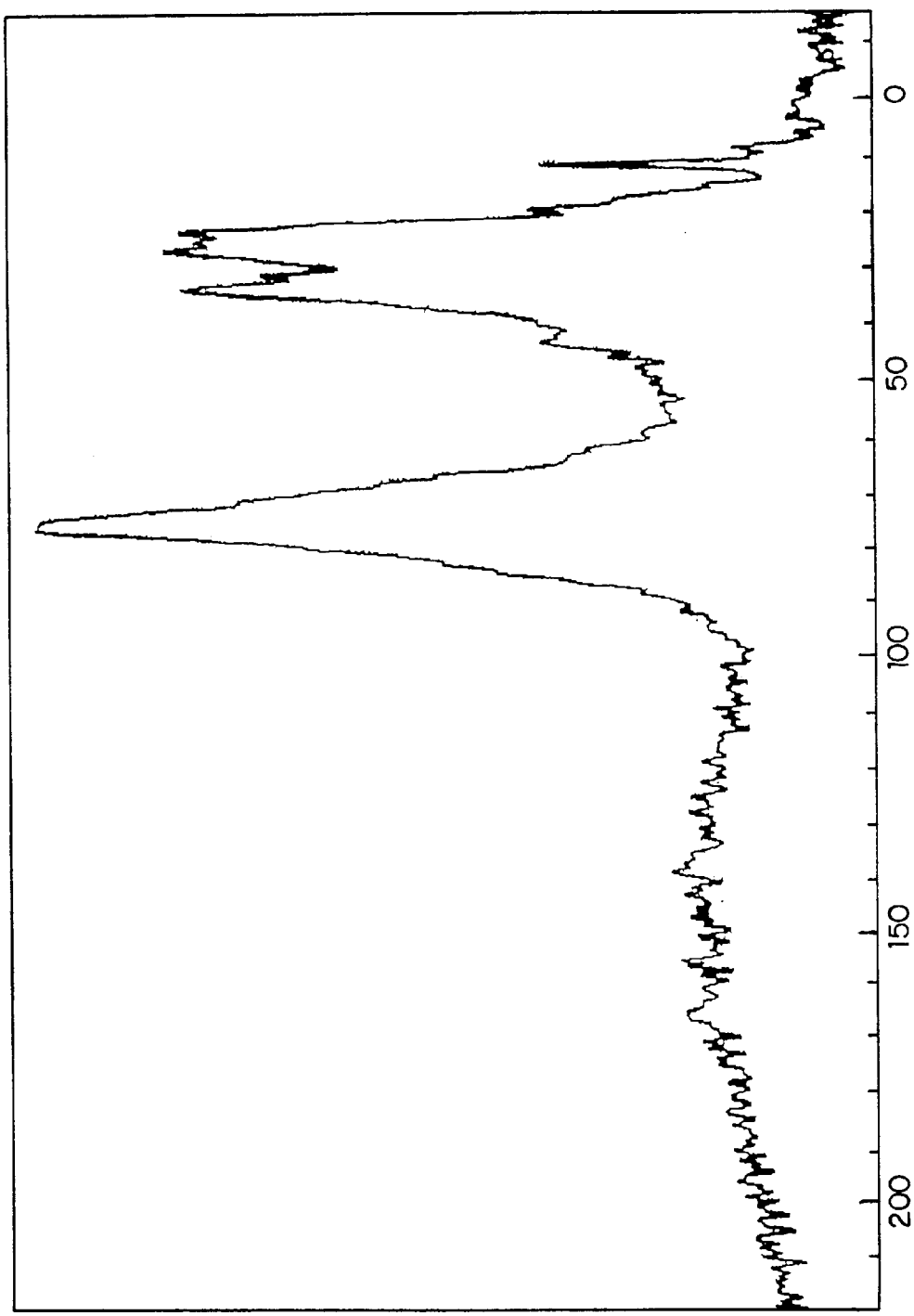
FIG. 25 is an $C^{13}$-NMR chart related to the phosphatized compound obtained in Example 10.

Peaks by carbon in the starting epoxy resin are observed in the vicinity of 46 ppm and 56 ppm. They disappear in the FIG. 25, resulting in showing disappearance of epoxy groups.

It appears that absorption peaks at 60–90 ppm depend upon carbon bonded to oxygen, and they shift.

EXAMPLE 11

A mixture composed of 40 g of diethyleneglycol diglycidylether having an epoxy equivalent of 150 (Epolead NT212 manufactured by Daicel Chemical Industries, Ltd.) and 40 g of propyleneglycol monopropylether was charged by dropwise addition into 28.8 g of phosphoric acid over approximately 1 hour. Reaction temperature exothermally rose to 90° C. or so.

After completion of the exothermic reaction, the temperature was maintained at 90° C. by heating for approximately 2 hours to obtain a reaction crude solution. Oxirane oxygen concentration of the crude reaction solution was measured after cooled to obtain the value of 3.0.

It was confirmed by the oxirane oxygen concentration value that almost all of the epoxy groups reacted with phosphoric acid.

Acid value was 316.0 mg/KOH.

EXAMPLE 12

A mixture composed of 40 g of diethyleneglycol diglycidylether having an epoxy equivalent of 215 (Epolead NT214 manufactured by Daicel Chemical Industries, Ltd.) and 40 g of propyleneglycol monopropylether was charged by dropwise addition into 20.0 g of phosphoric acid over approximately 1 hour. Reaction temperature exothermally rose to 90° C. or so.

After completion of the exothermic reaction, the temperature was maintained at 90° C. by heating for approximately 2 hours to obtain a reaction crude solution. Oxirane oxygen concentration of the reaction crude solution was measured after cooled to obtain the value of 0.

It was confirmed by the oxirane oxygen concentration value that almost all of the epoxy groups reacted with phosphoric acid.

Acid value was 239.0 mg/KOH.

EXAMPLE 13

A mixture composed of 40 g of neopentylglycol diglycidylether and 40 g of propyleneglycol monopropylether was charged by dropwise addition into 26.0 g of phosphoric acid over approximately 1 hour. Reaction temperature exothermally rose to 90° C. or so.

After completion of the exothermic reaction, the temperature was maintained at 90° C. by heating for approximately 2 hours to obtain a reaction crude solution. Oxirane oxygen concentration of the reaction crude solution was measured after cooled to obtain the value of 0.

Acid value was 280.0 mg/KOH.

Figure 32:
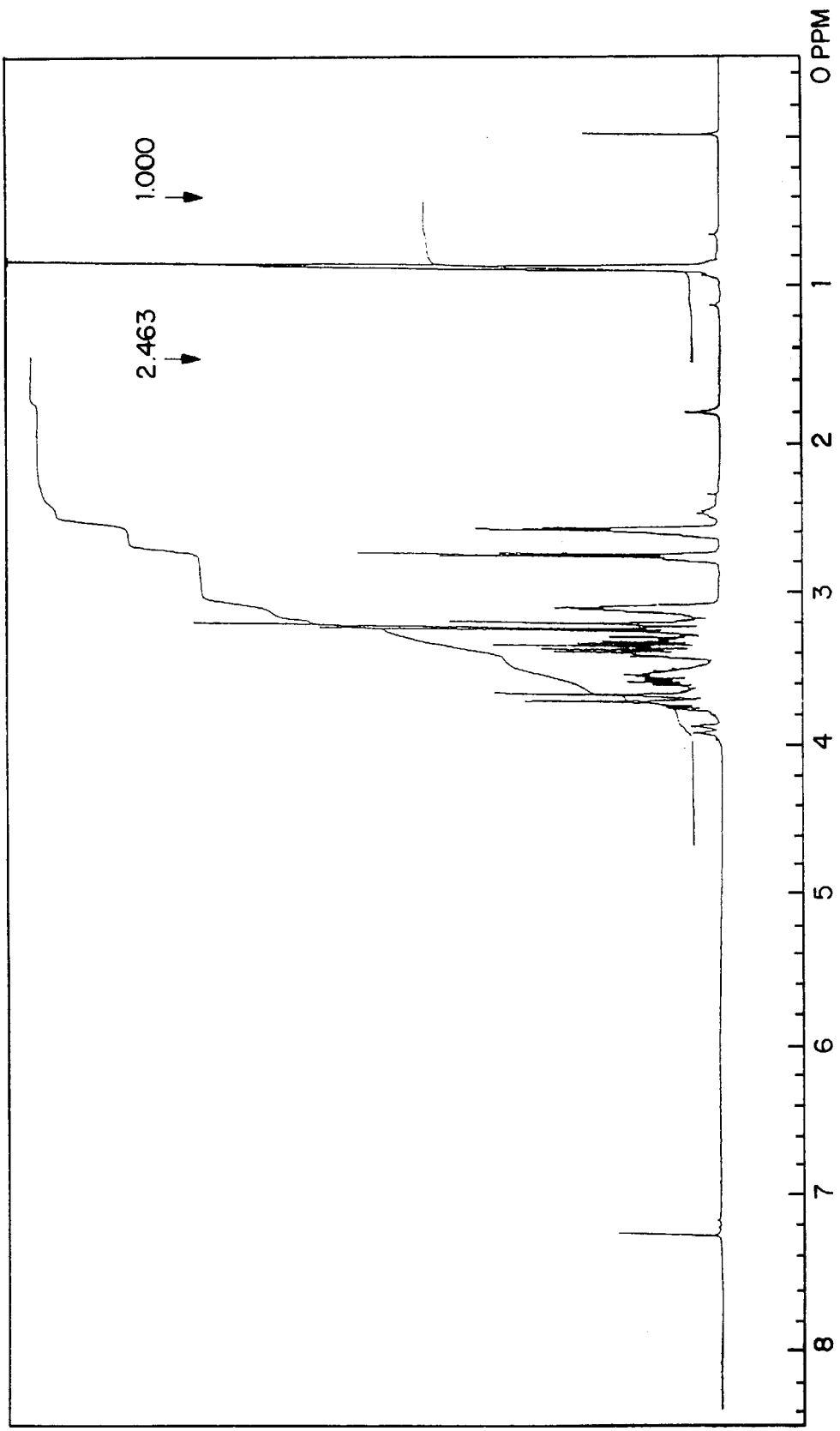
FIG. 32 is an NMR chart related to the starting epoxy compound used in Example 13.
Figure 33:
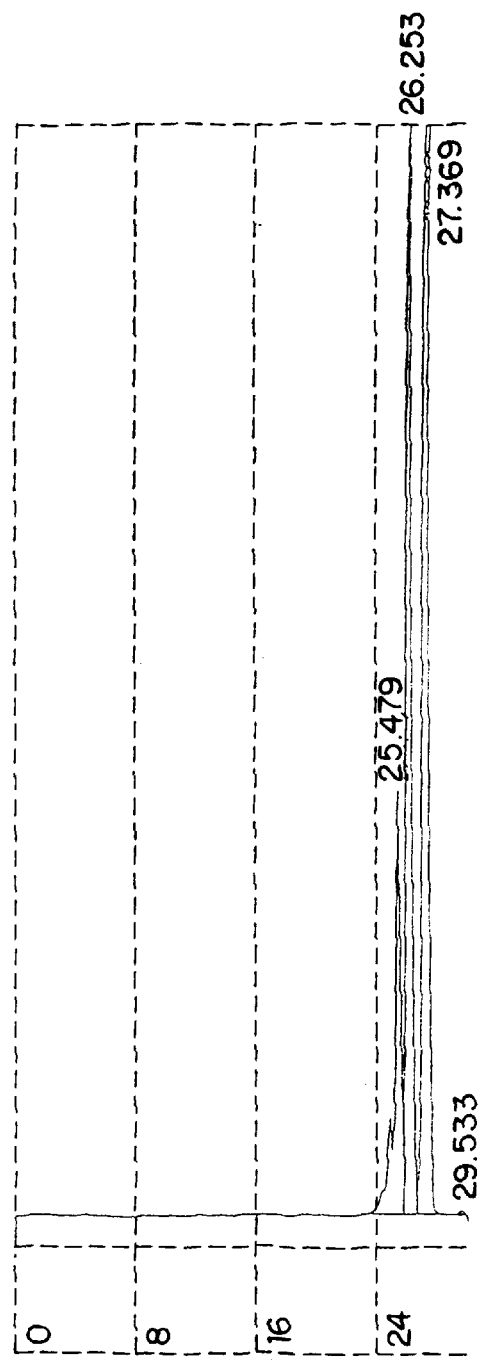
FIG. 33 is a GPC chart related to the starting epoxy compound used in Example 13.
Figure 64:
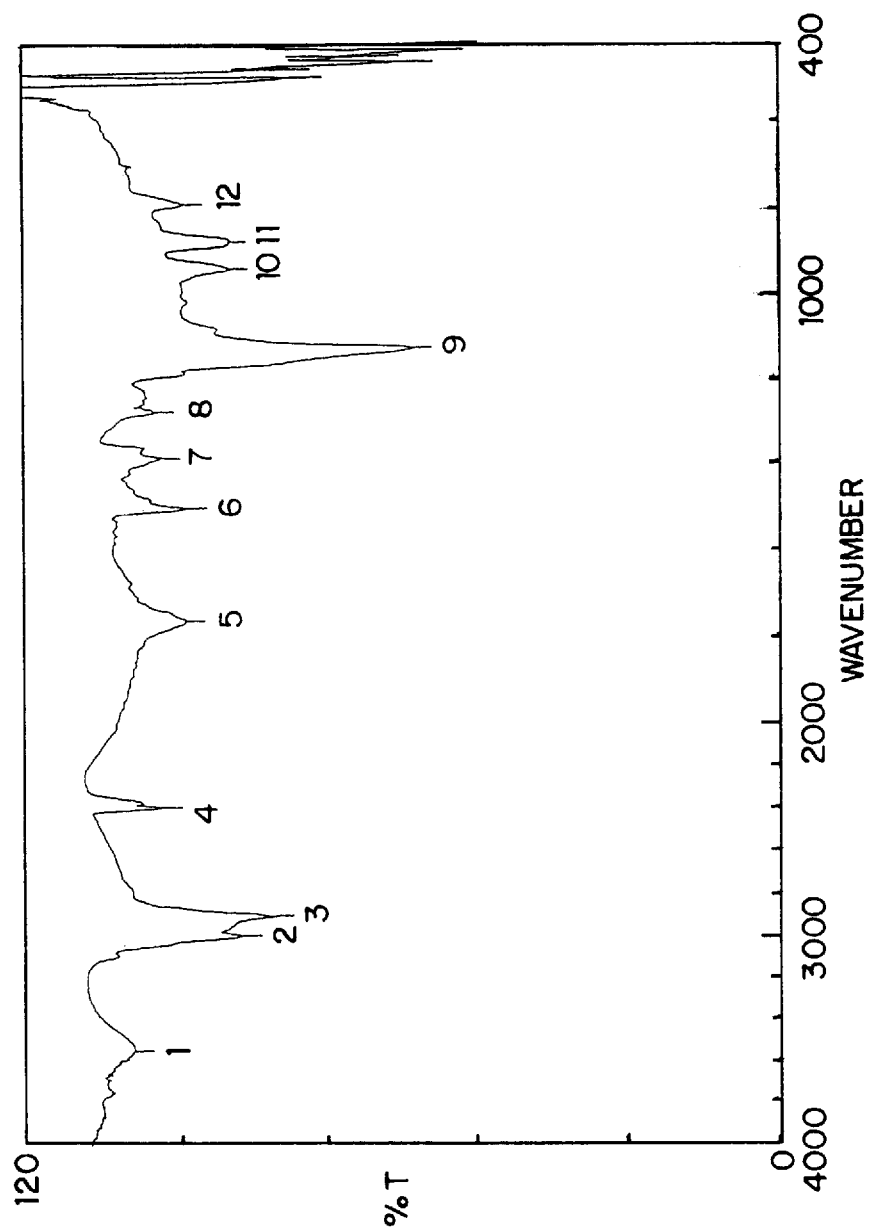
FIG. 64 is an IR spectra chart related to the starting epoxy compound in Example 13.

FIGS. 32, 33 and 64 are an NMR chart, a GPC chart and an IR spectra chart relating to the starting epoxy compound, respectively.

Figure 34:
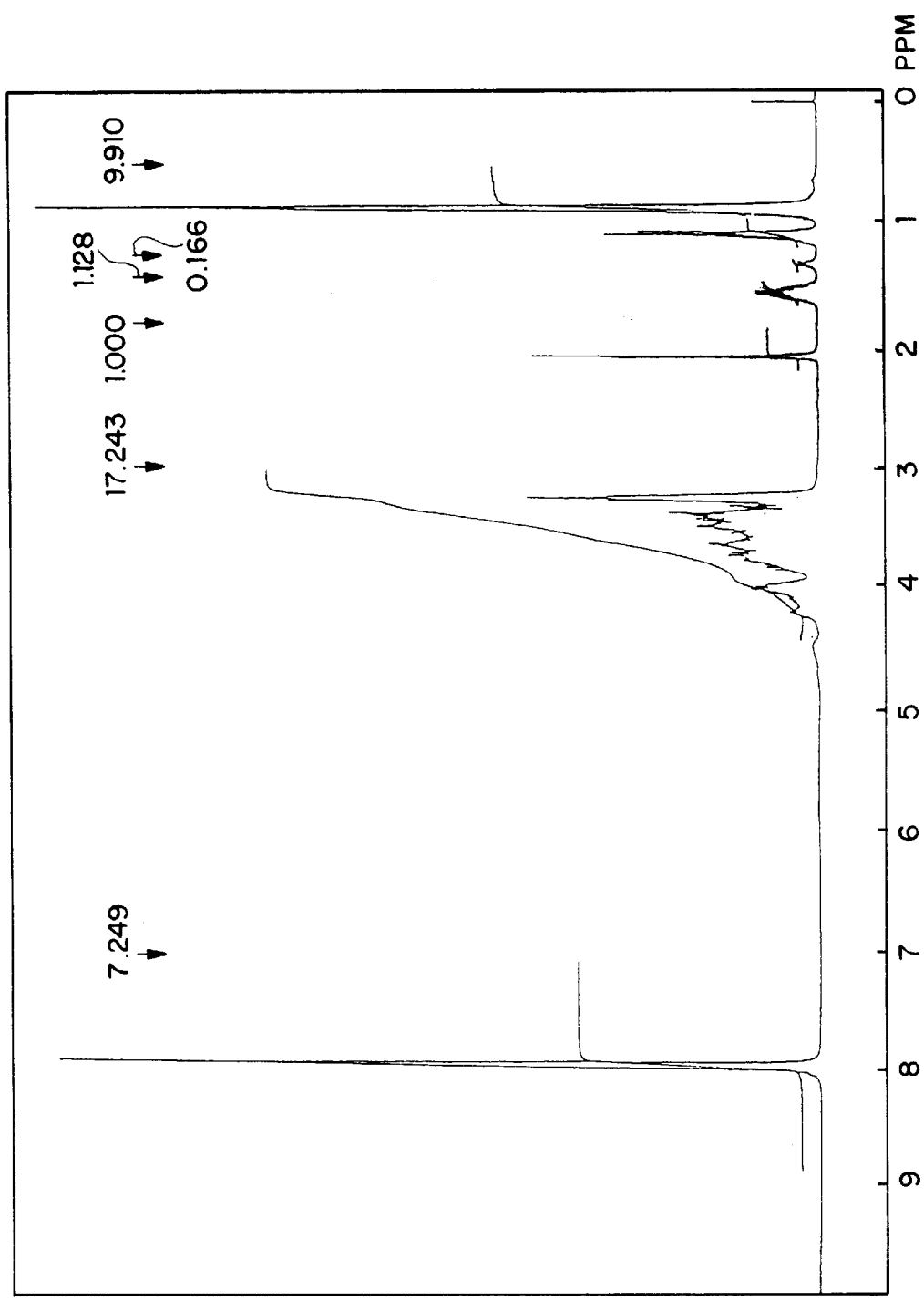
FIG. 34 is an NMR chart related to the phosphatized compound obtained in Example 13.
Figure 45:
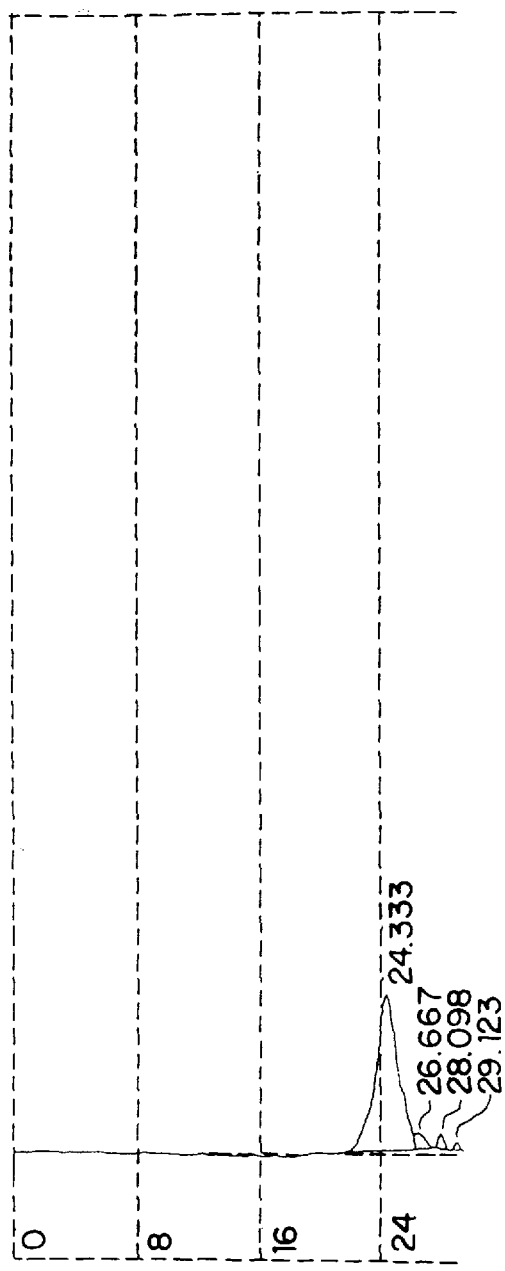
FIG. 45 is a GPC chart related to the phosphatized compound obtained in Example 15.
Figure 65:
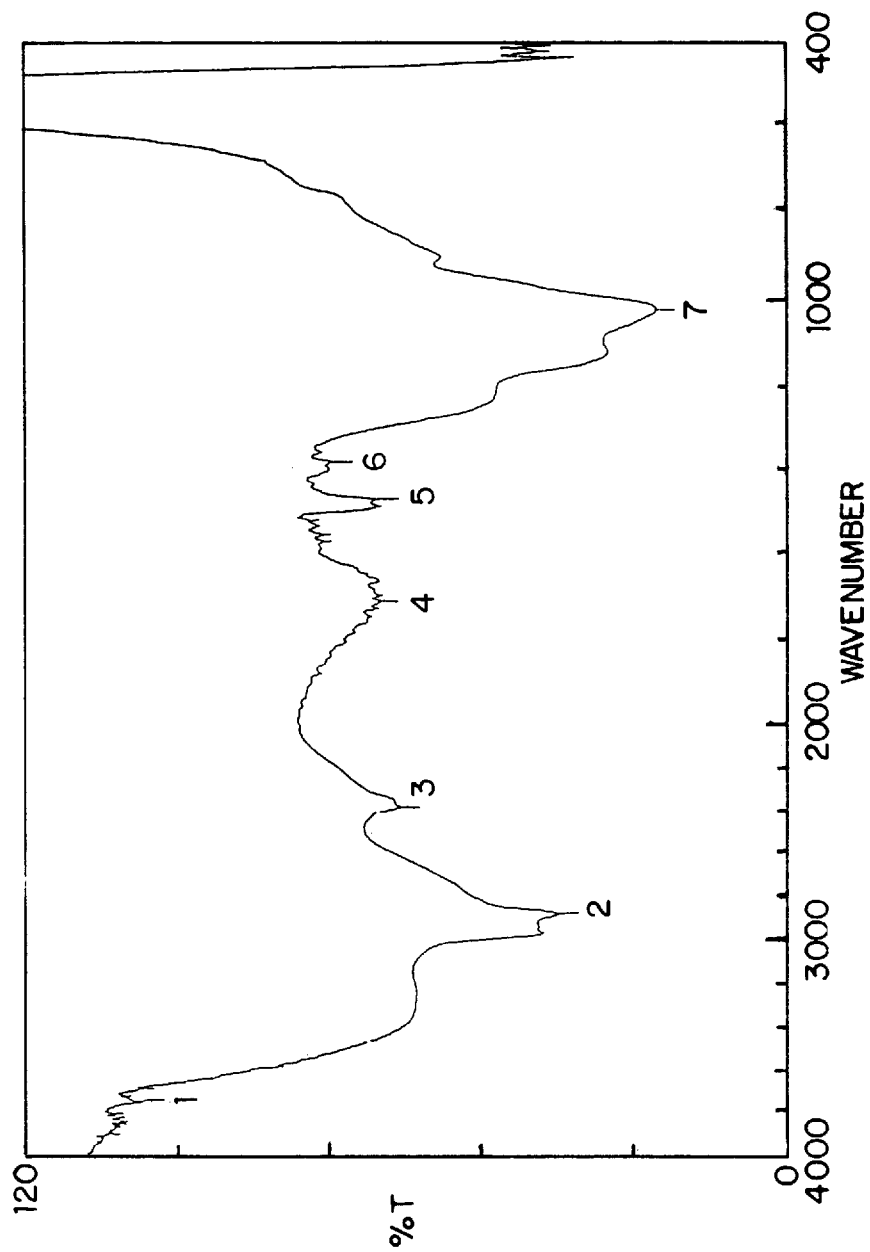
FIG. 65 is an IR spectra chart related to the phosphatized compound obtained in Example 13.

FIGS. 34, 45 and 65 are an NMR chart, a GPC chart and an IR spectra chart relating to the phosphatized compound obtained, respectively.

EXAMPLE 14

A mixture composed of 40 g of diglycerol polyglycidylether having an epoxy equivalent of 155 and 40 g of propyleneglycol monopropylether was charged by dropwise addition into 25.3 g of phosphoric acid over approximately 1 hour. Other procedures are same as in Example 11 to obtain a phosphatized compound. Oxirane oxygen concentration of the phosphatized compound was measured after cooled to obtain the value of 0.

Acid value was 275 mg/KOH.

Figure 35:
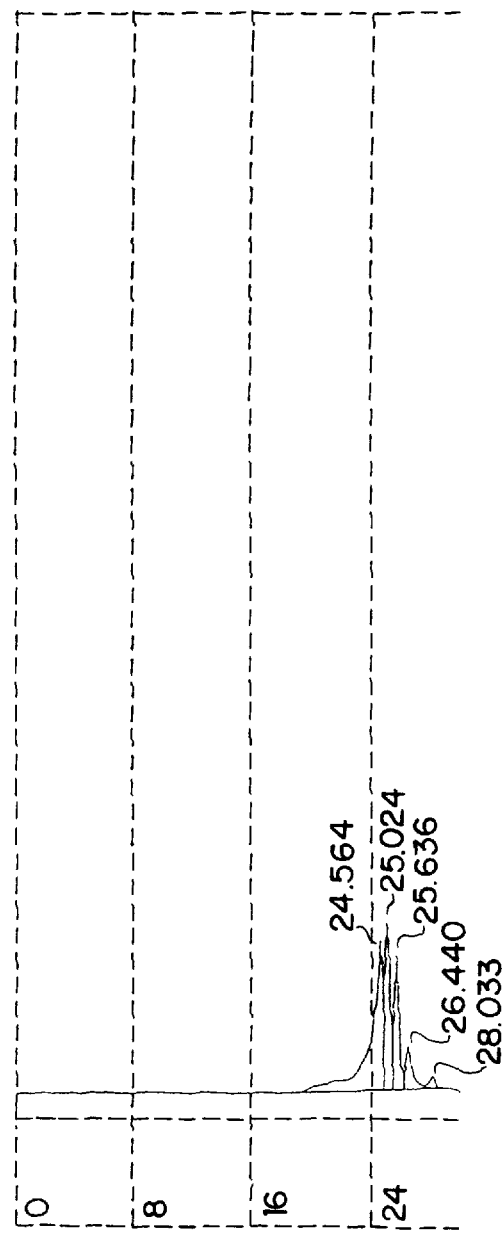
FIG. 35 is a GPC chart related to the phosphatized compound obtained in Example 13.
Figure 36:
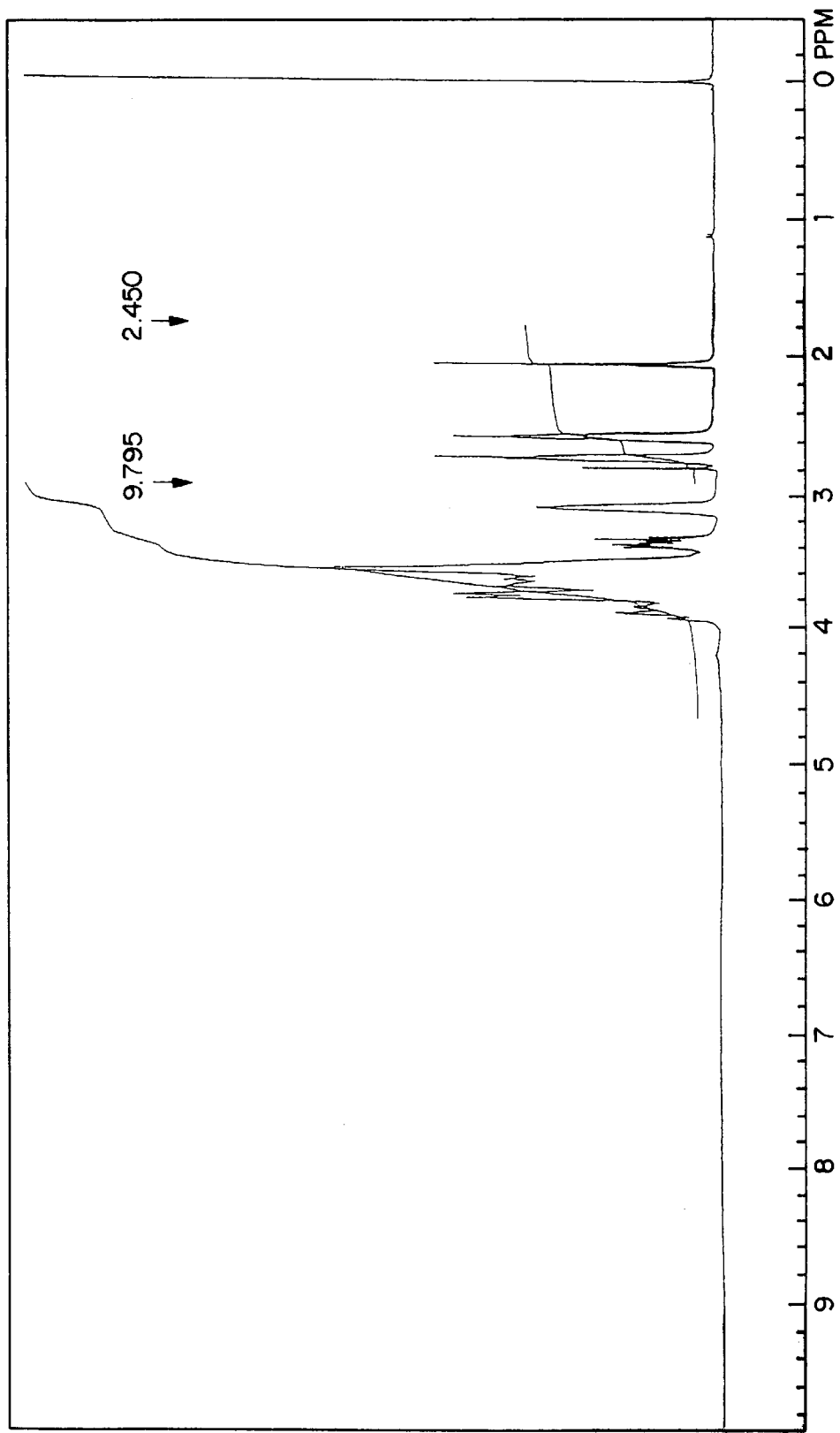
FIG. 36 is an NMR chart related to the starting epoxy compound in Example 14.
Figure 37:
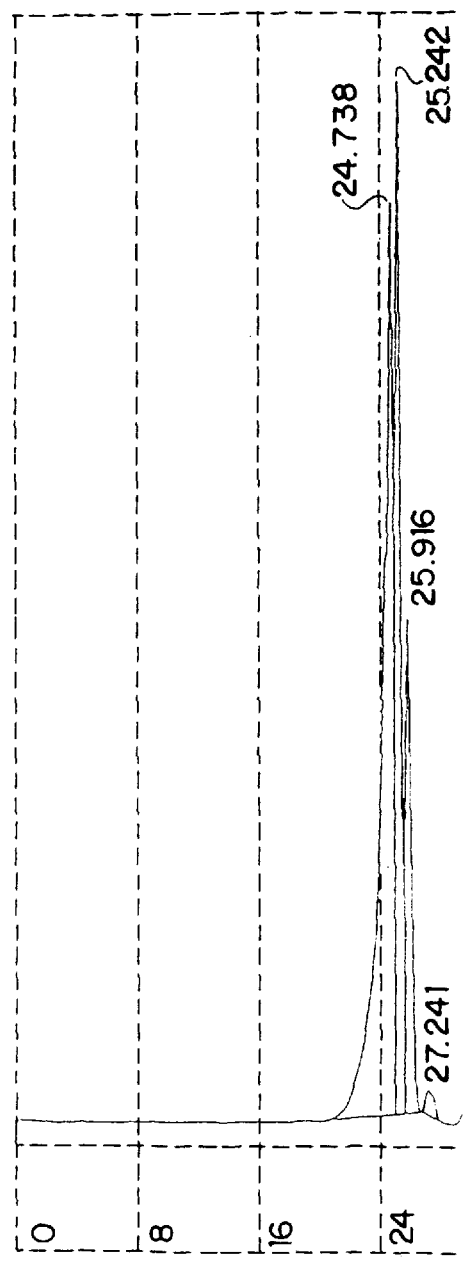
FIG. 37 is a GPC chart related to the starting epoxy compound in Example 14.
Figure 38:
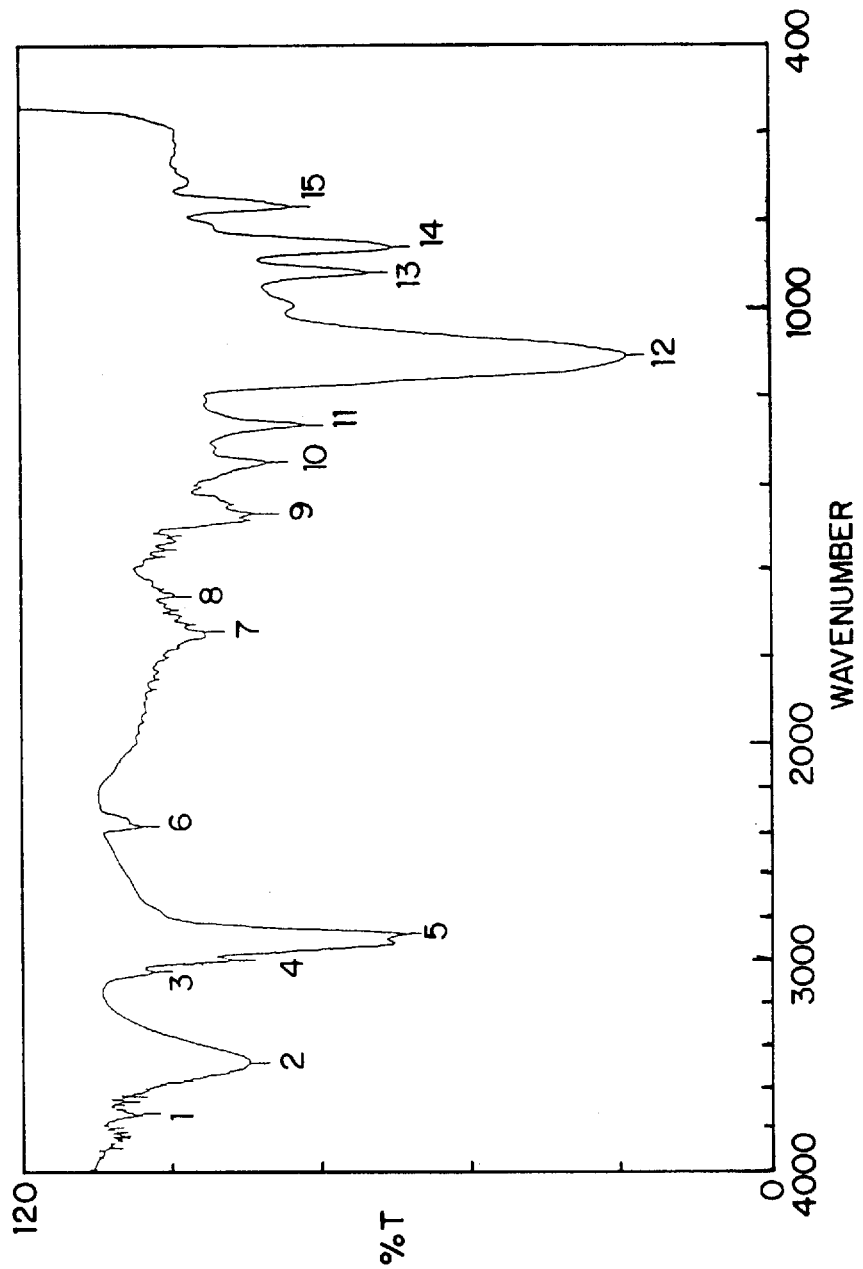
FIG. 38 is an IR spectra chart related to the starting epoxy compound in Example 14.

FIGS. 35, 37 and 38 are an NMR chart, a GPC chart and an IR spectra chart relating to the starting epoxy compound, respectively.

Figure 39:
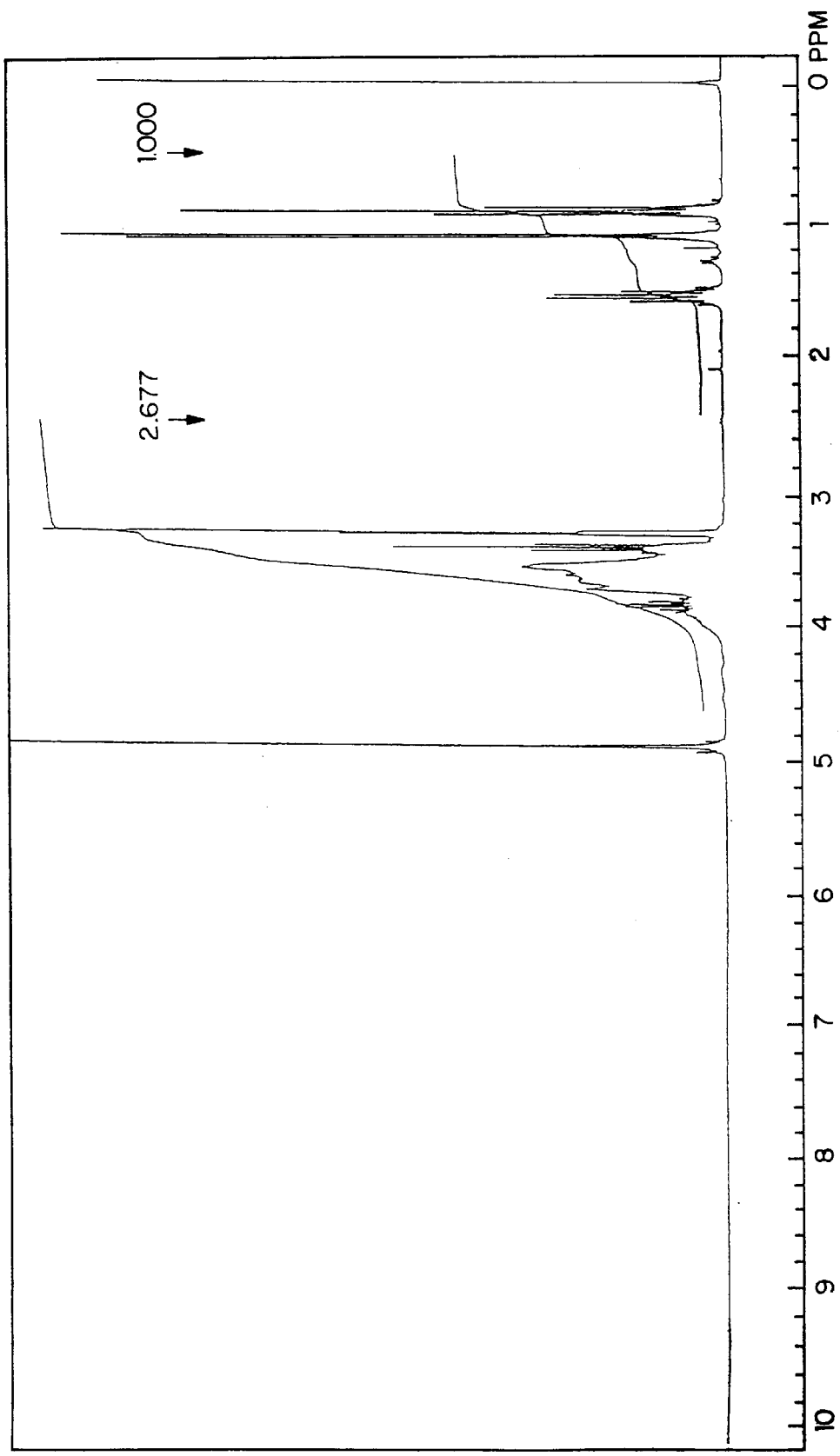
FIG. 39 is an NMR chart related to the phosphatized compound obtained in Example 14.
Figure 40:
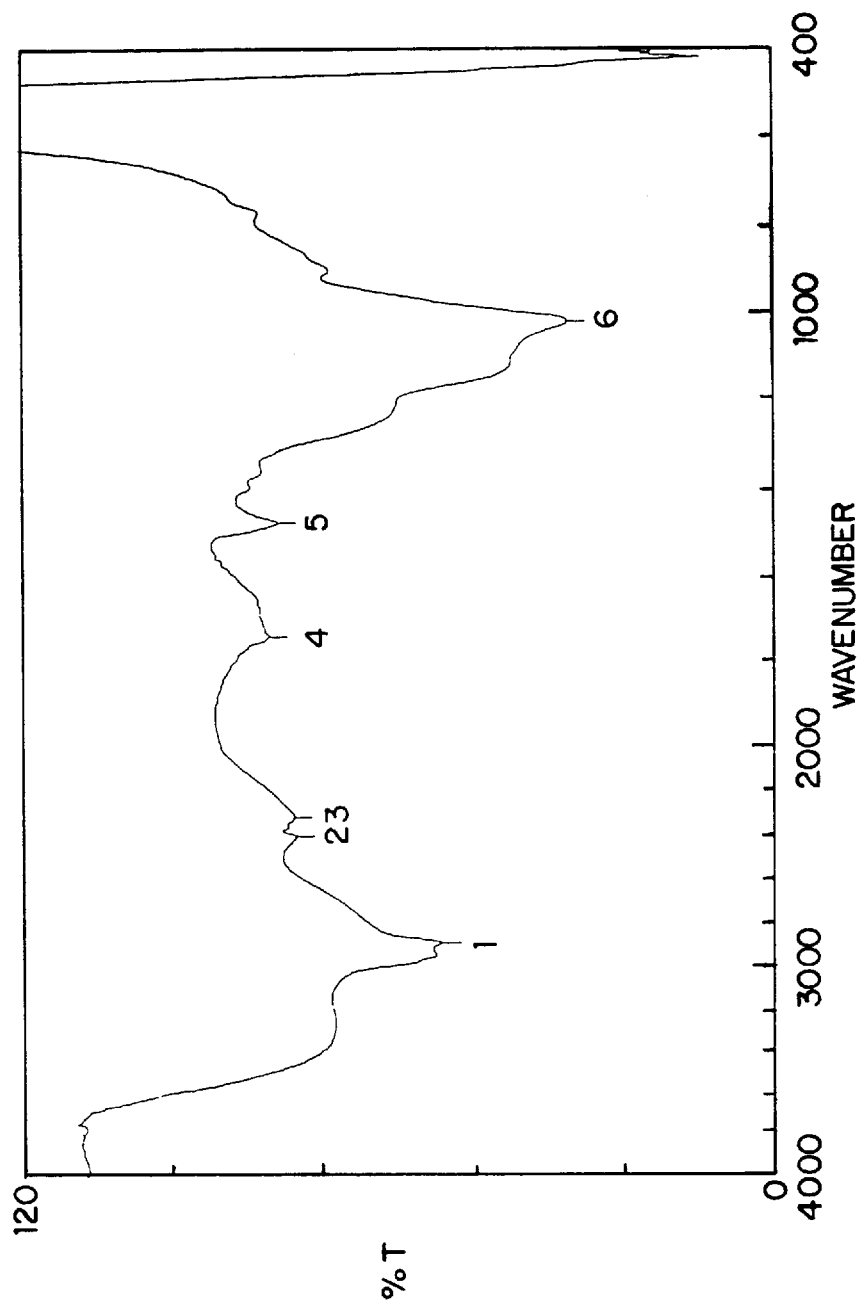
FIG. 40 is an IR spectra chart related to the phosphatized compound obtained in Example 14.

FIGS. 39 and 40 are an NMR chart and an IR spectra chart relating to the phosphatized compound obtained, respectively.

EXAMPLE 15

A mixture composed of 40 g of polyethyleneglycol diglycidylether having an epoxy equivalent of 587 and 40 g of propyleneglycol monopropylether was charged by dropwise addition into 6.8 g of phosphoric acid over approximately 1 hour. Other procedures are same as in Example 11 to obtain a phosphatized compound. Oxirane oxygen concentration of the phosphatized compound was measured after cooled to obtain the value of 0.

Acid value was 90.0 mg/KOH.

Figure 41:
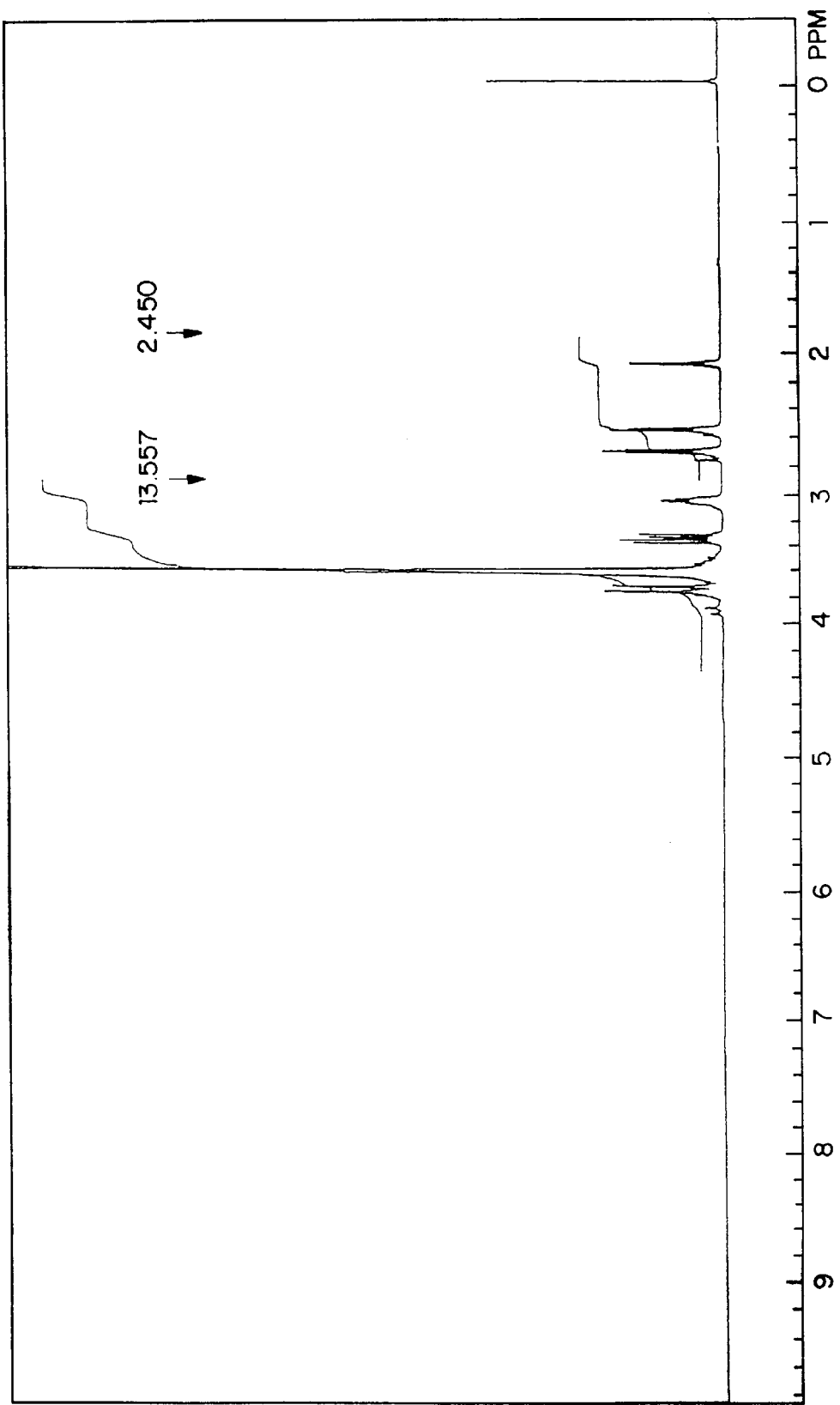
FIG. 41 is an NMR chart related to the starting epoxy compound in Example 15.
Figure 42:
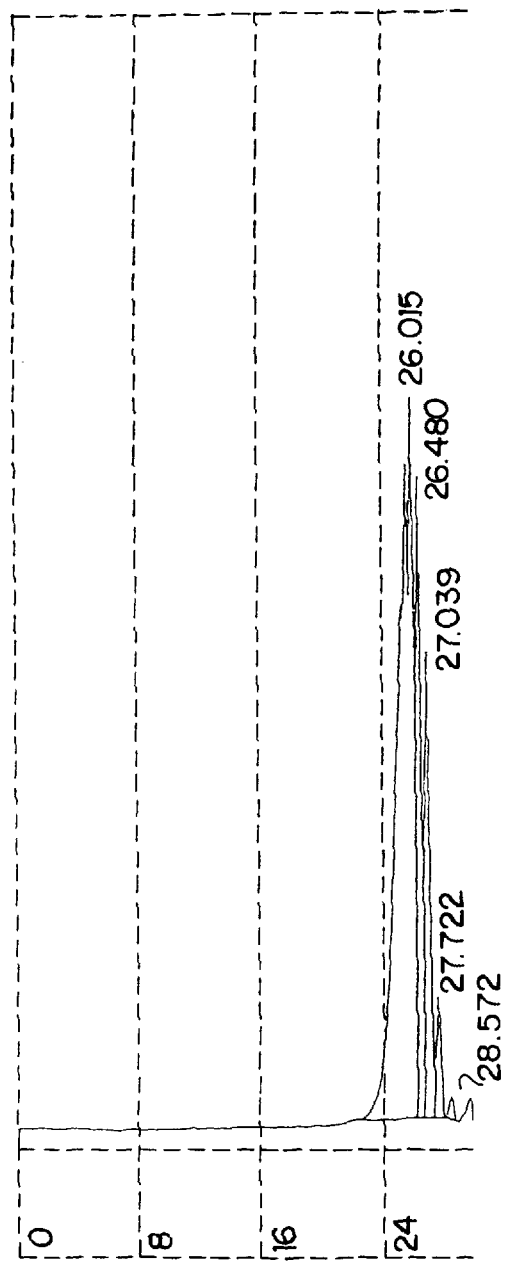
FIG. 42 is a GPC chart related to the starting epoxy compound in Example 15.
Figure 43:
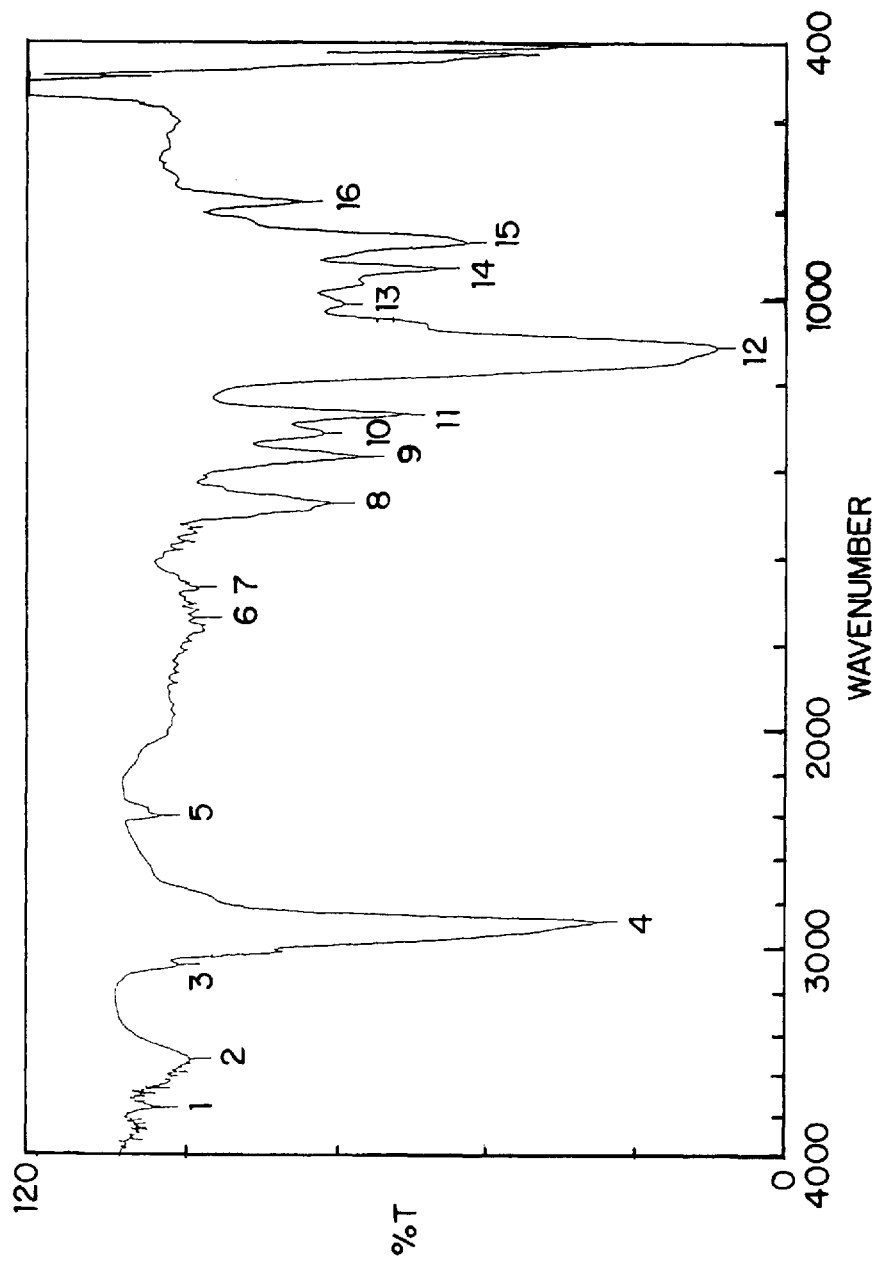
FIG. 43 is an IR spectra chart related to the starting epoxy compound in Example 15.

FIGS. 41, 42 and 43 are an NMR chart, a GPC chart and an IR spectra chart relating to the starting epoxy compound, respectively.

Figure 44:
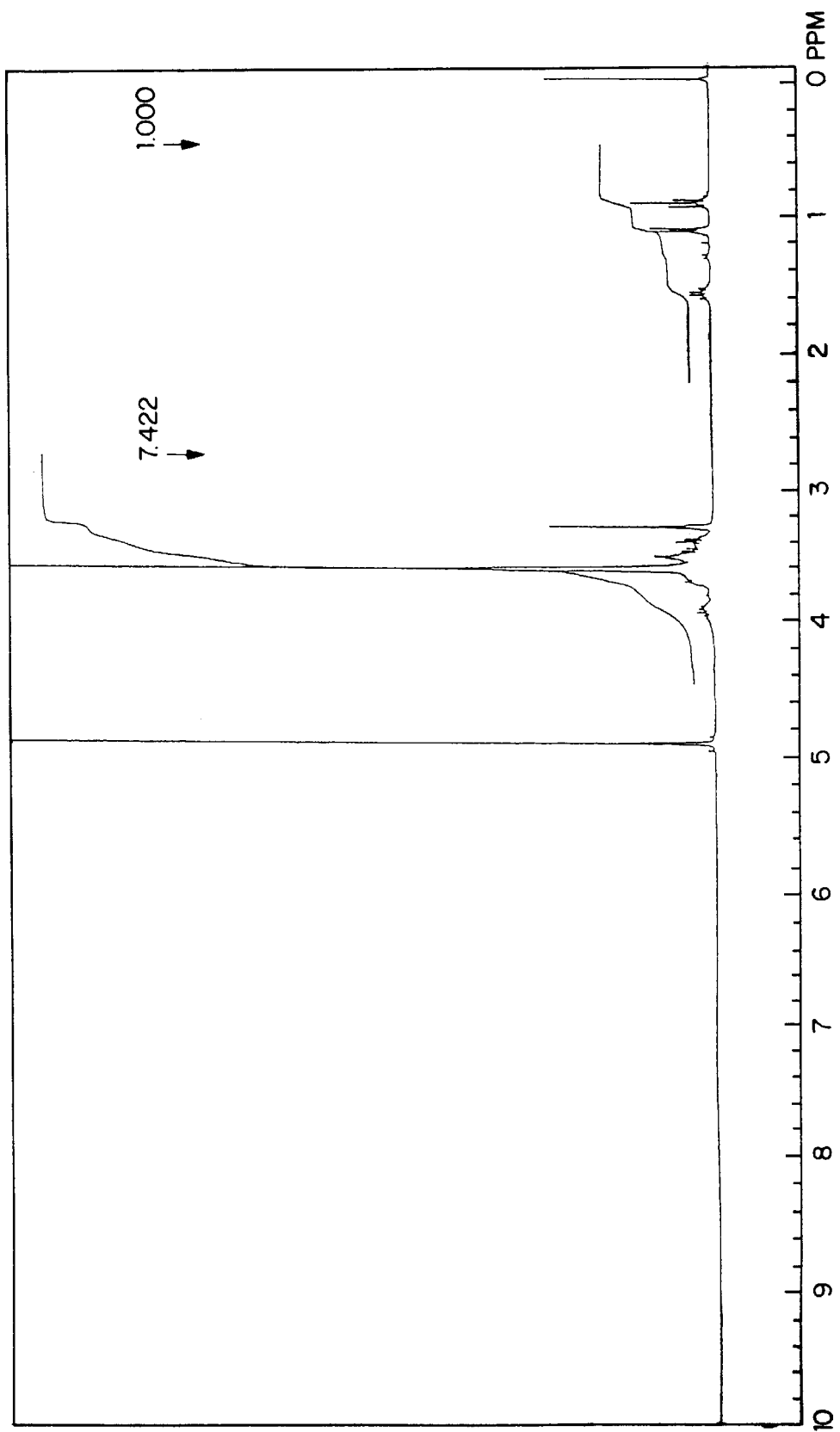
FIG. 44 is an NMR chart related to the phosphatized compound obtained in Example 15.
Figure 46:
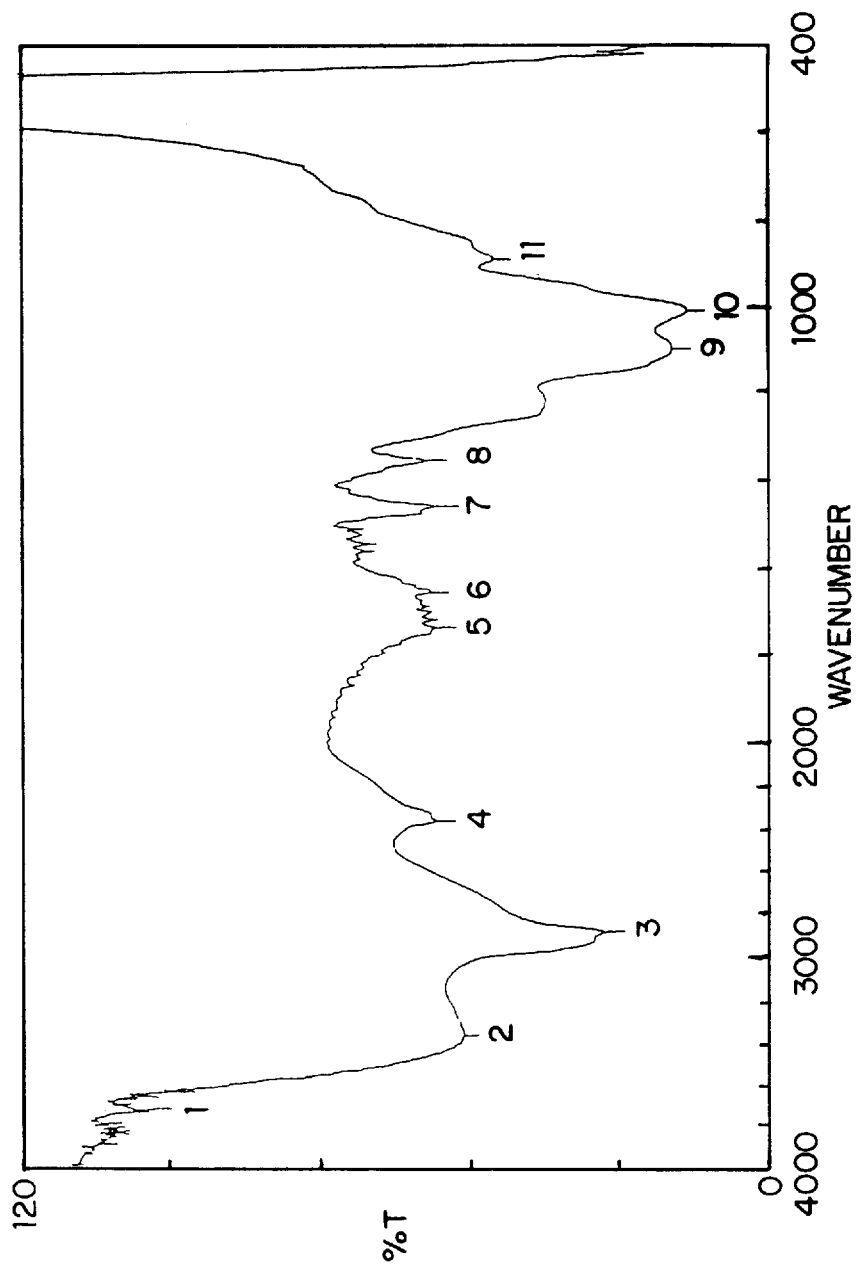
FIG. 46 is an IR spectra chart related to the phosphatized compound obtained in Example 15.

FIGS. 44, 45 and 46 are an NMR chart, a GPC chart and an IR spectra chart relating to the phosphatized compound obtained, respectively.

EXAMPLE 16

A mixture composed of 40 g of tripropyleneglycol diglycidylether having an epoxy equivalent of 198.7 and 40 g of propyleneglycol monopropylether was charged by dropwise addition into 19.8 g of phosphoric acid over approximately 1 hour. Other procedures are same as in Example 11 to obtain a phosphatized compound. Oxirane oxygen concentration of the phosphatized compound was measured after cooled to obtain the value of 0.

Acid value was 227 mg/KOH.

Figure 47:
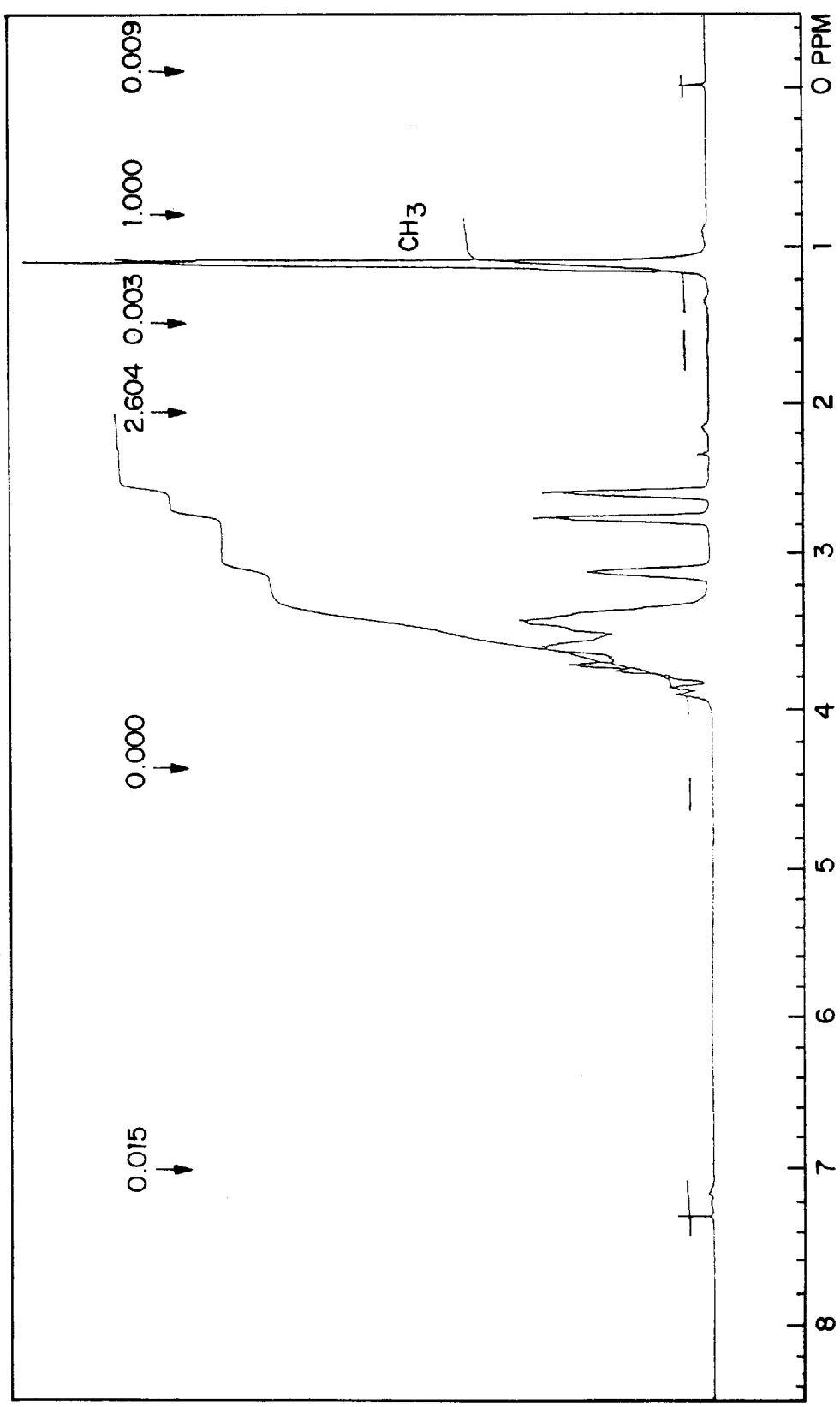
FIG. 47 is an NMR chart related to the starting epoxy compound Example 16.
Figure 48:
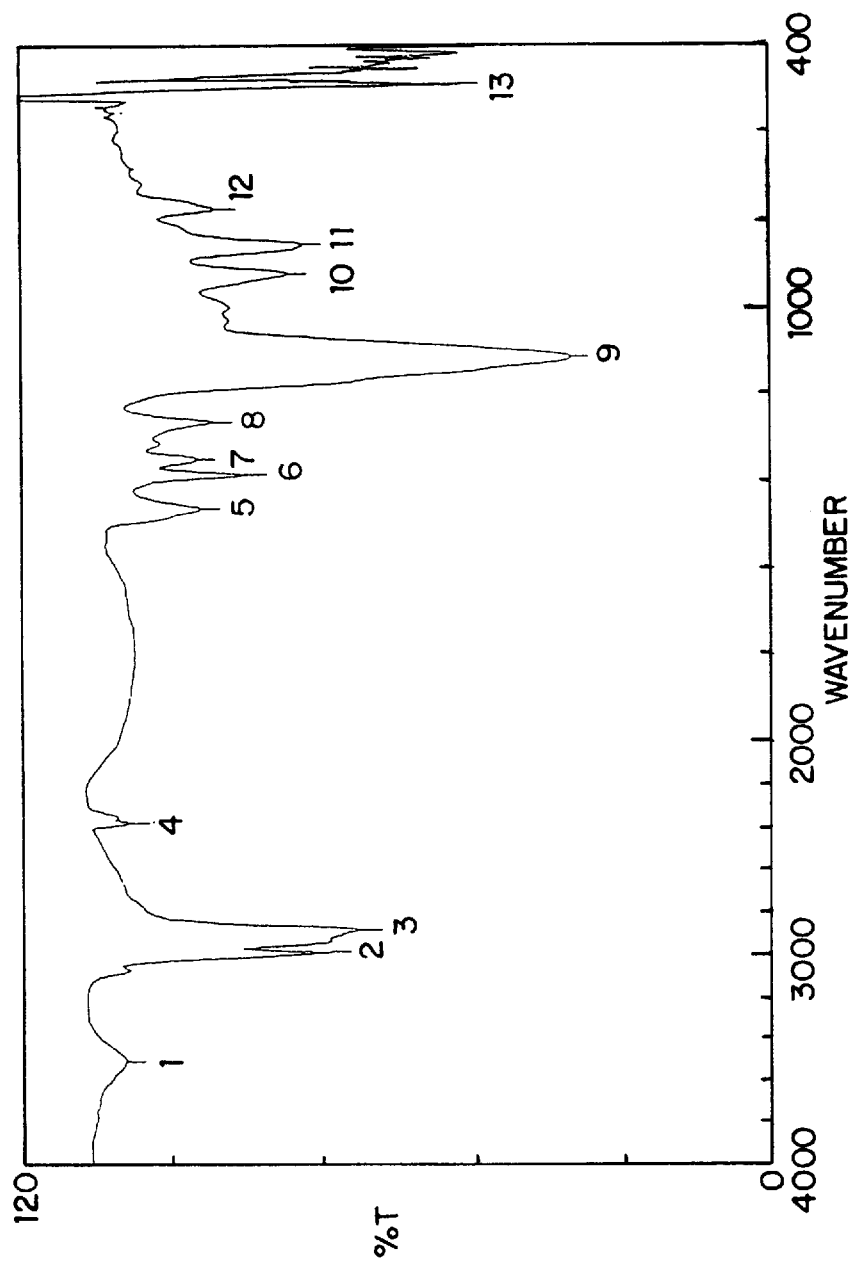
FIG. 48 is an NMR chart related to the starting epoxy compound In Example 16.
Figure 49:
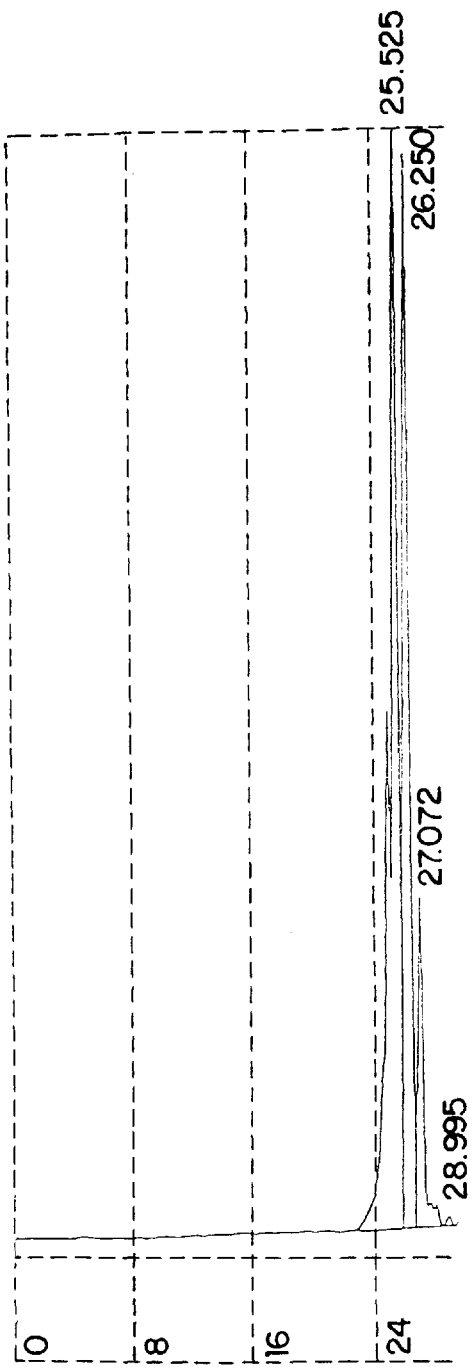
FIG. 49 is a GPC chart related to the starting epoxy compound in Example 16.

FIGS. 47, 48 and 49 are an NMR chart, an IR spectra chart and a GPC chart relating to the starting epoxy compound, respectively.

Figure 50:
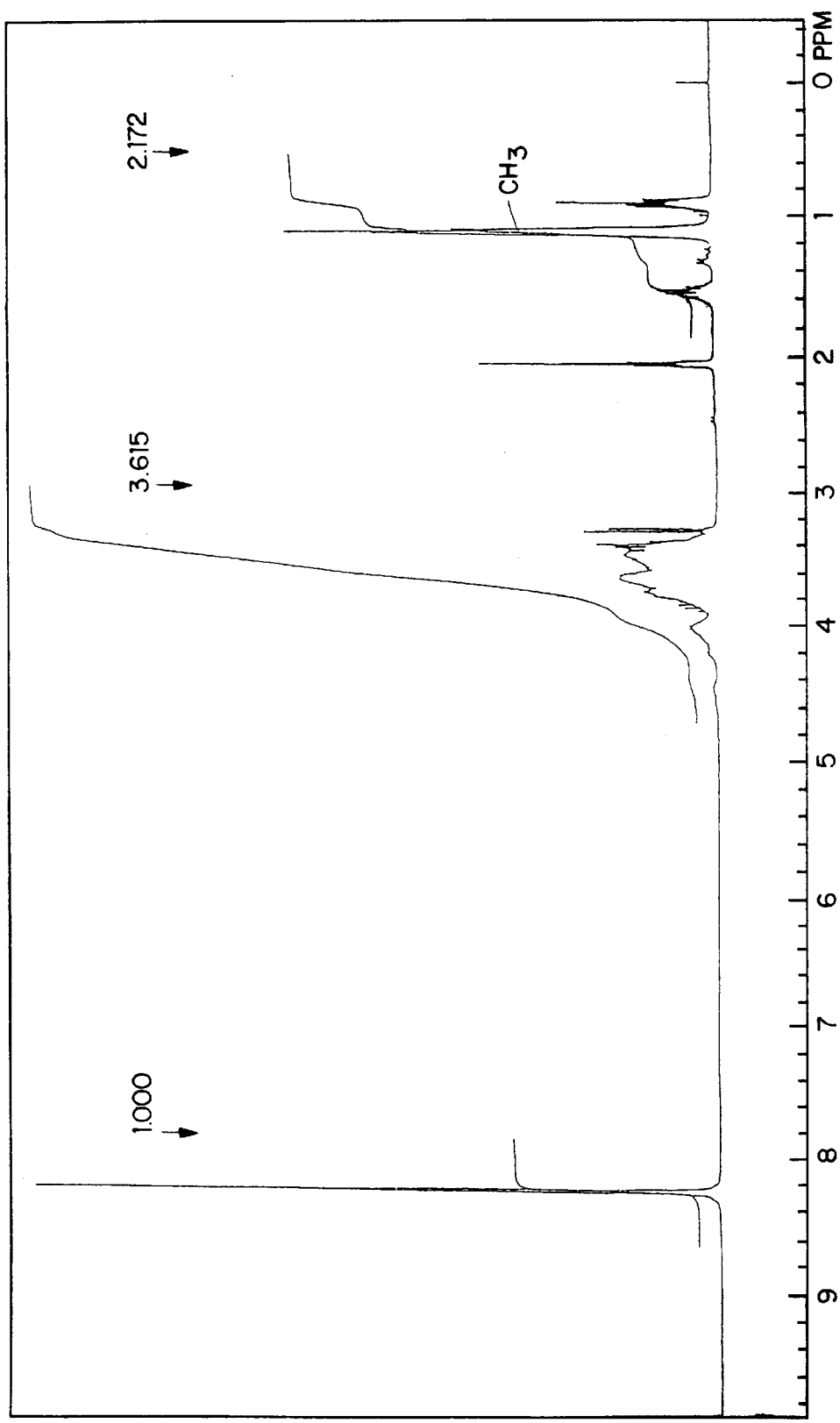
FIG. 50 is an NMR chart related to the phosphatized compound obtained in Example 16.
Figure 51:
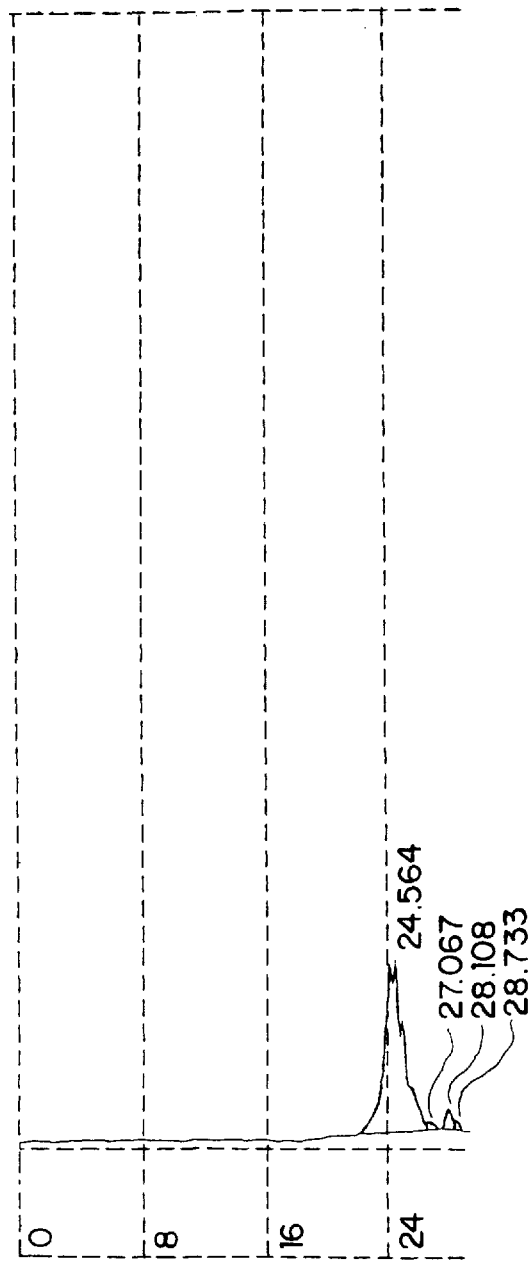
FIG. 51 is a GPC chart related to the phosphatized compound obtained in Example 16.
Figure 52:
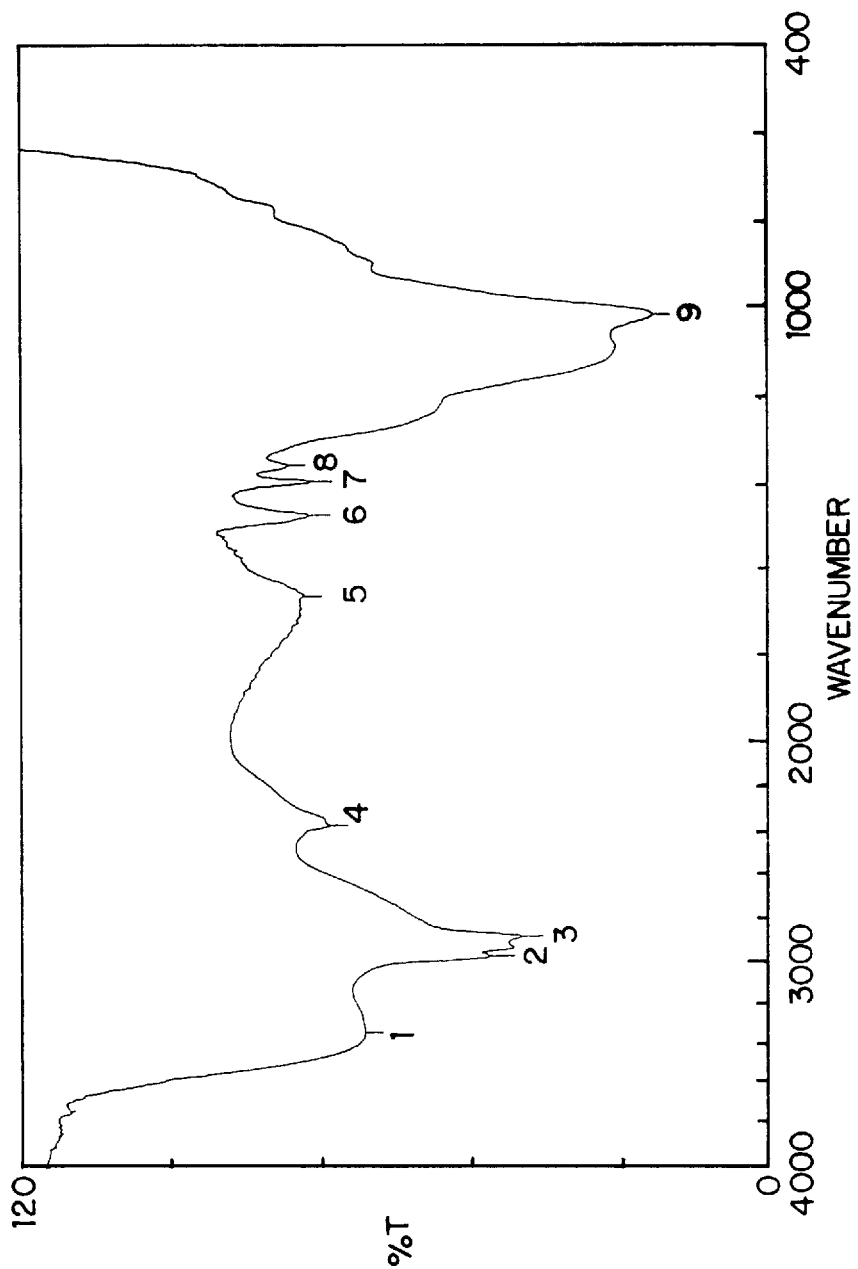
FIG. 52 is an IR spectra chart related to the phosphatized compound obtained in Example 16.
Figure 53:
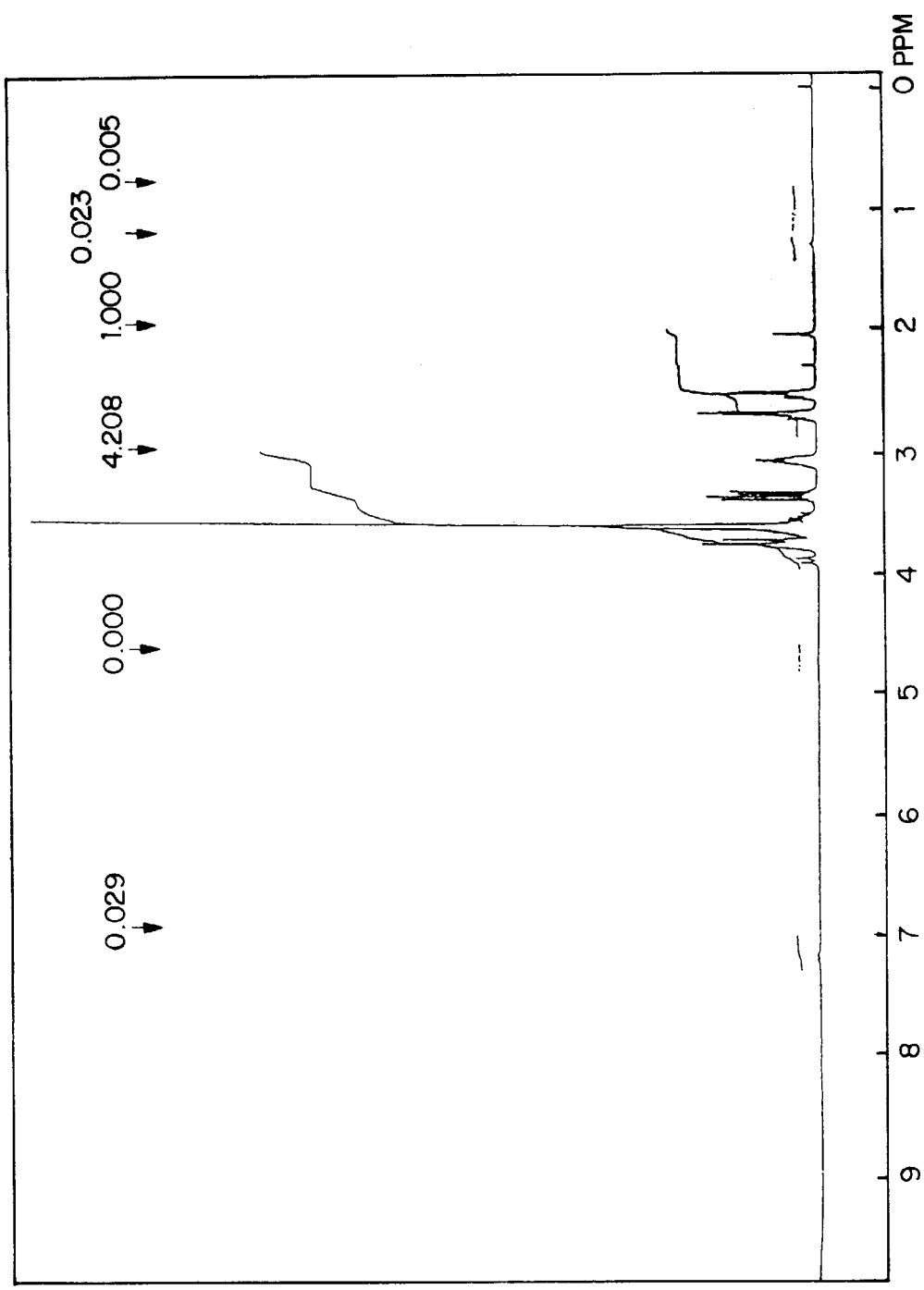
FIG. 53 is an NMR chart related to the starting epoxy compound in Example 11.

FIGS. 50, 51 and 52 are an NMR chart, a GPC chart and an IR spectra chart relating to the phosphatized compound obtained, respectively.

EXAMPLE 17

Figure 27:
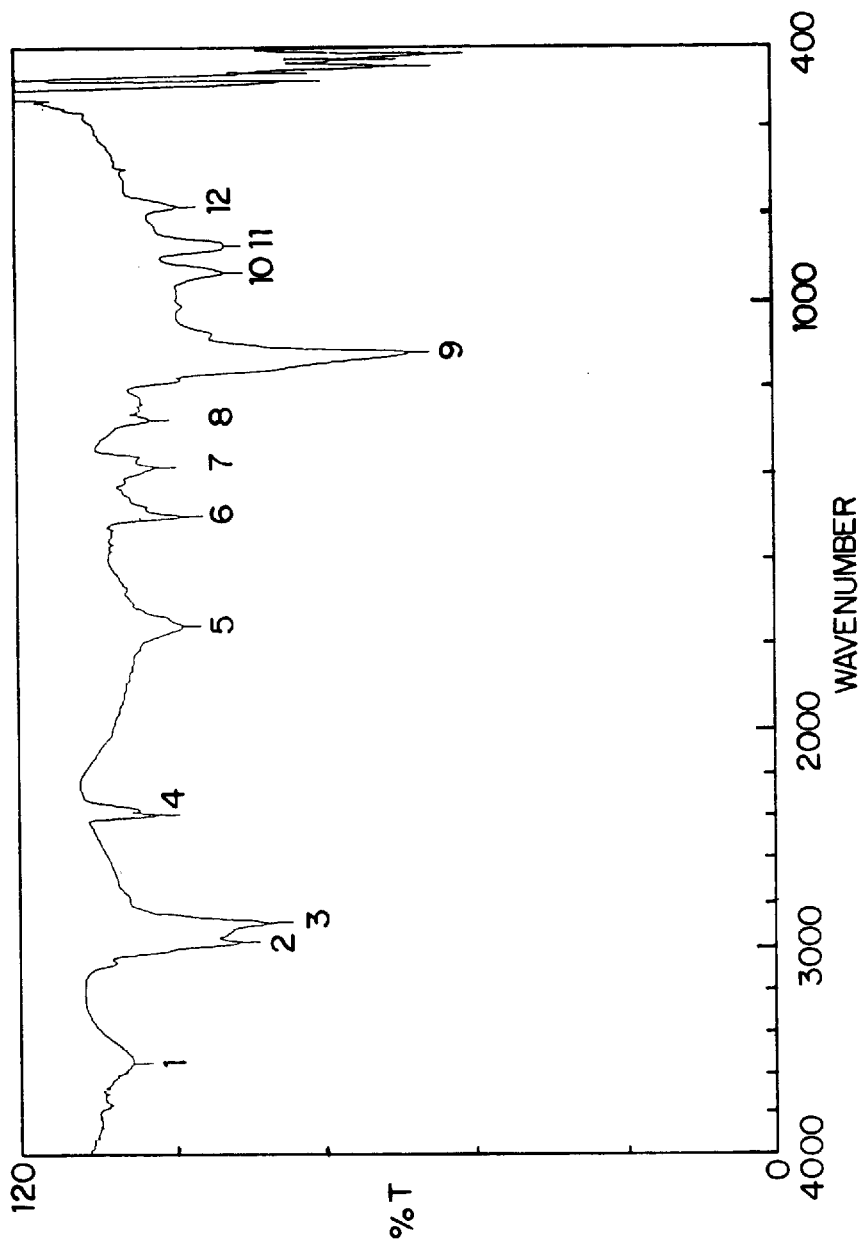
FIG. 27 is an IR spectra chart related to the starting epoxy compound in Example 13.

Low-boiling-point ingredients were removed from the reaction crude solution obtained in Example 13 at 80°–100° C. and 2–5 mmHg for 2 hours with a rotary evaporator. IR spectra changed from the FIG. 27 in relation to the starting epoxy compound to FIG. 28 in relation to the phosphatized compound obtained.

Figure 28:
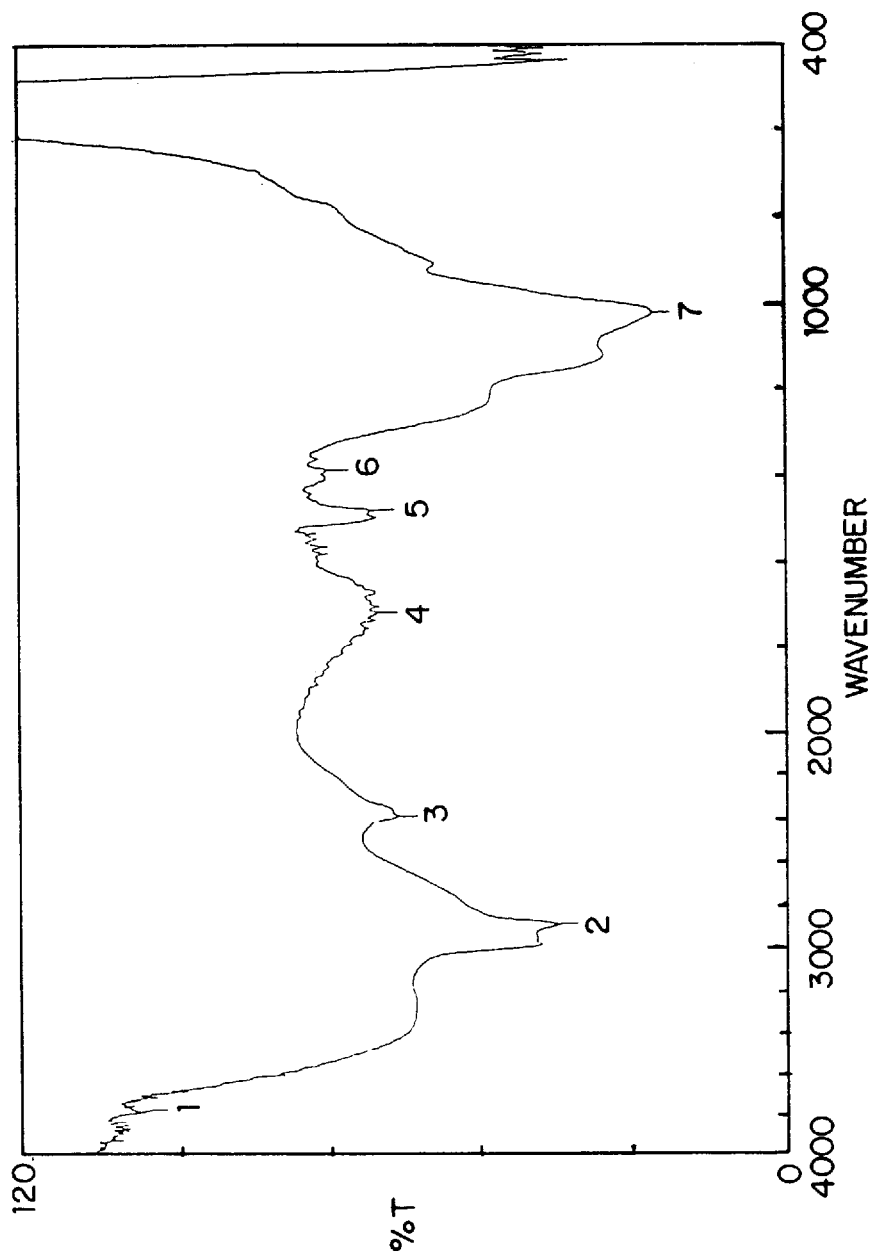
FIG. 28 is an IR spectra chart related to the phosphatized compound obtained in Example 13.
Figure 29:
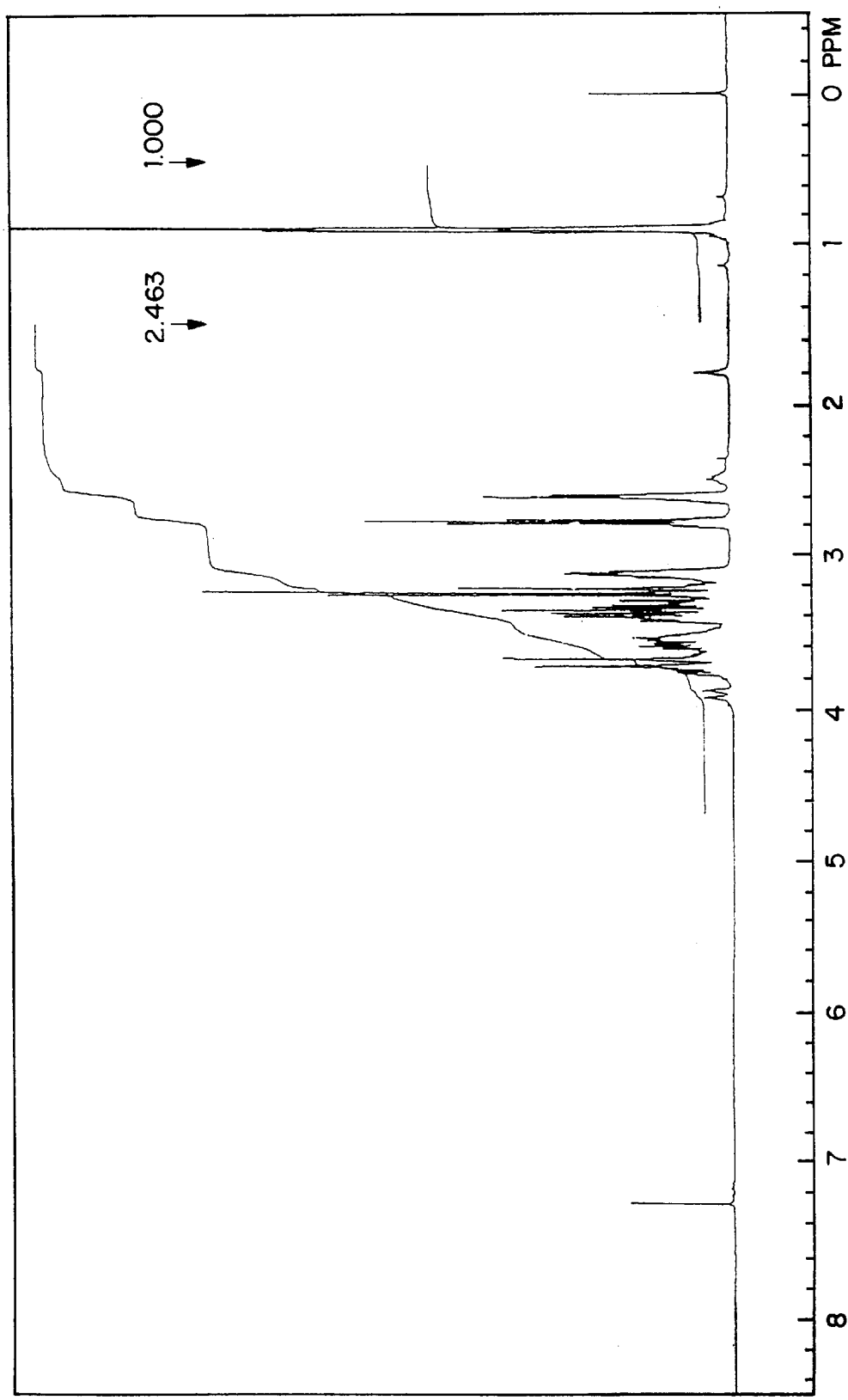
FIG. 29 is an $H^1$-NMR chart related to the starting epoxy compound in Example 13.
Figure 30:
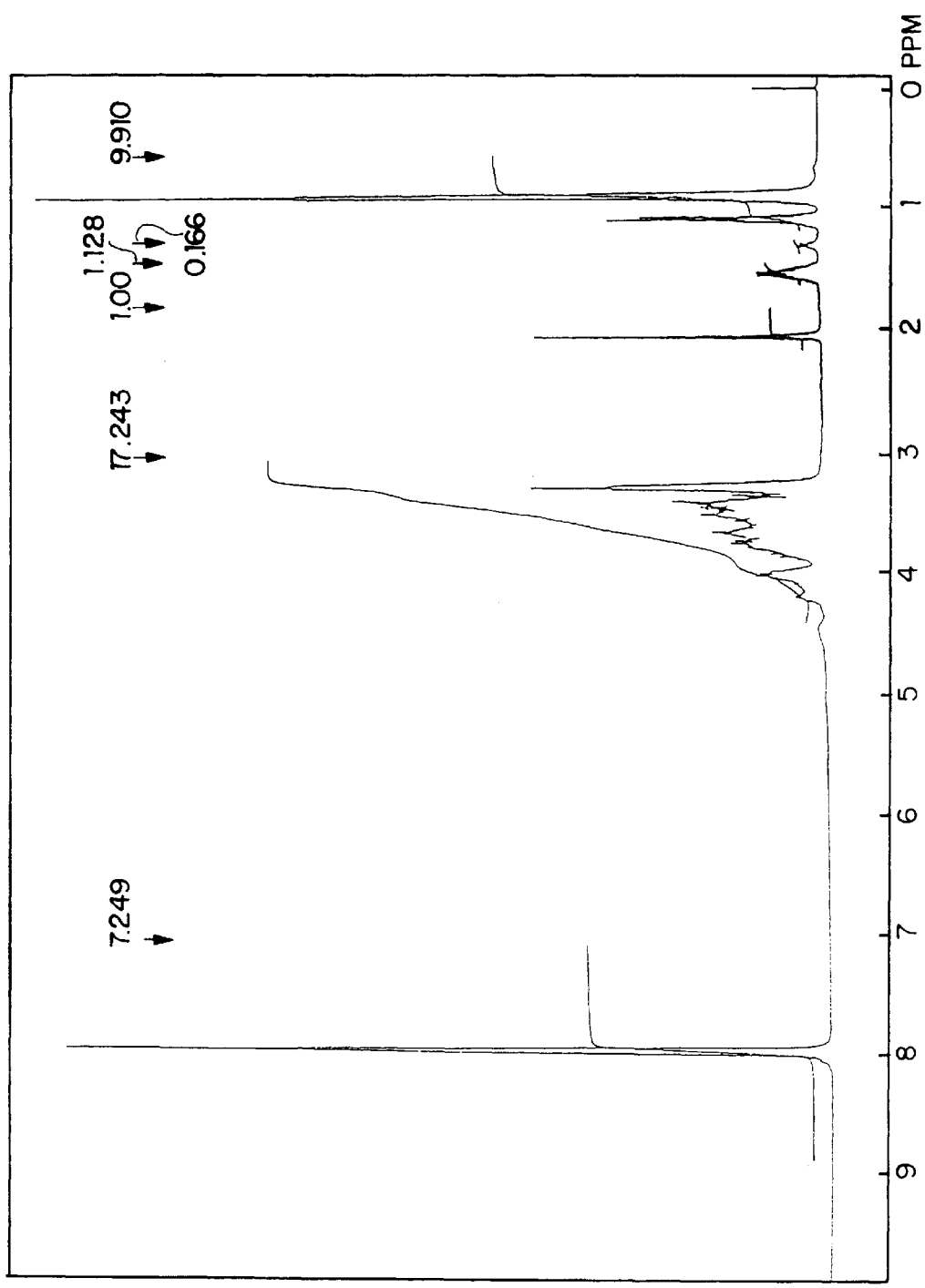
FIG. 30 is an $H^1$-NMR chart related to the phosphatized compound obtained in Example 13.

FIG. 28 exhibits that absorption peaks by P-O are observed at 950 cm$^{-1}$ and 1100 cm$^{-1}$. In the H$^1$-NMR charts, absorption peaks by epoxy groups in the FIG. 29 changed to peaks in FIG. 30.

It is characterized that delta peaks at 2.6–2.8 ppm by epoxy groups disappear and change to a peak at delta 2.05 ppm by methylene, and there appears a peak at delta 8.0 ppm by proton in phosphoric acid.

Figure 31:
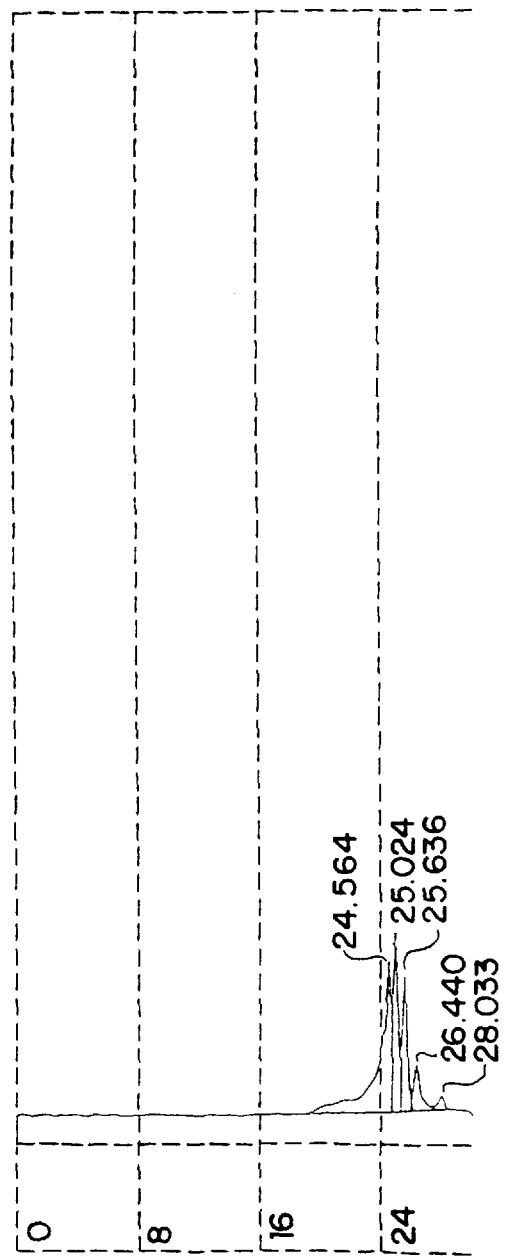
FIG. 31 is a GPC chart related to the phosphatized compound obtained in Example 13.

Molecular weight and distribution thereof are shown in the FIG. 31.

It was confirmed that a number average molecular weight (Mn) is 457, a weight average molecular weight (Mw) is 832 and the molecular weight distribution (Mw/Mn) is 1.82 based on Polystyrene.

EXAMPLES 18 to 22

Same procedures as described in Example 17 were repeated.

EXAMPLE 18

There were carried out respective spectrum analyses in relation to the sample obtained in Example 11.

Figure 54:
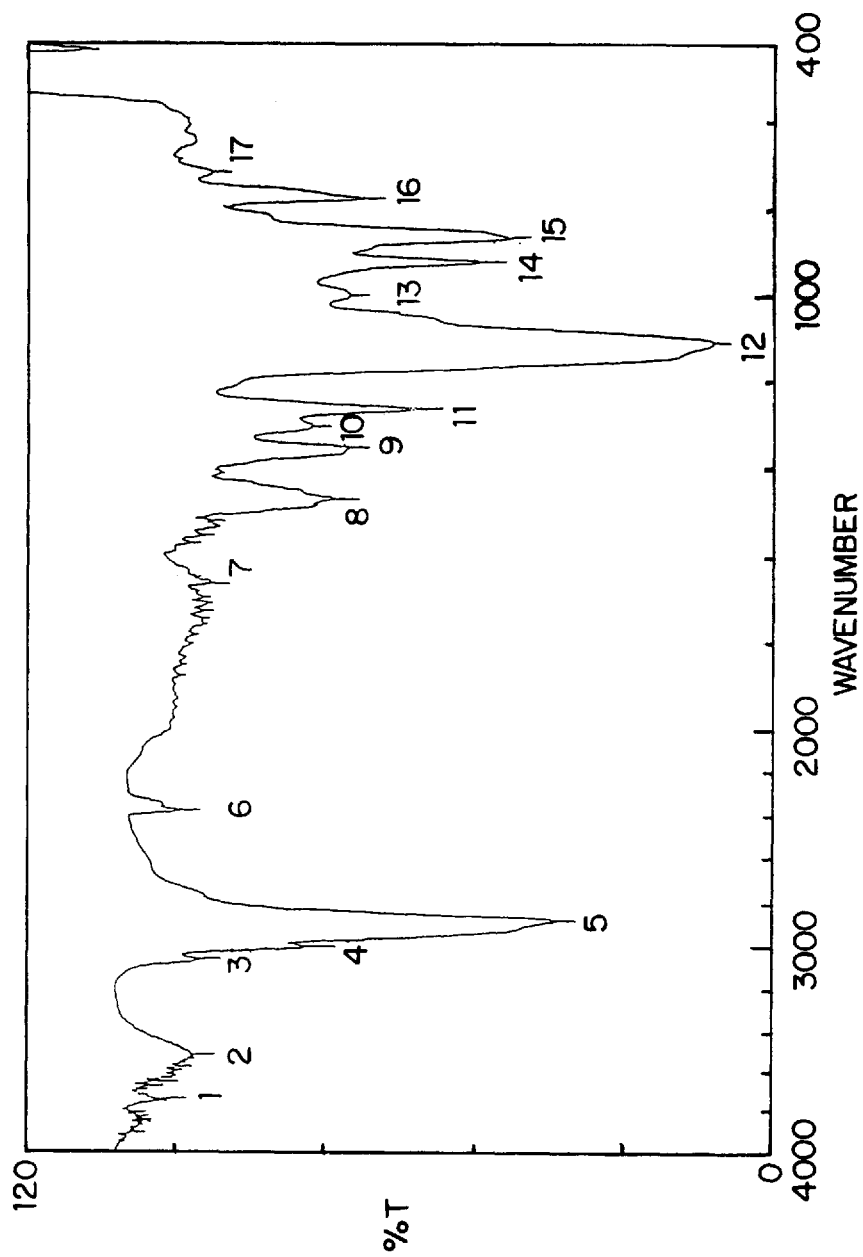
FIG. 54 is an IR spectra chart related to the starting epoxy compound in Example 11.
Figure 55:
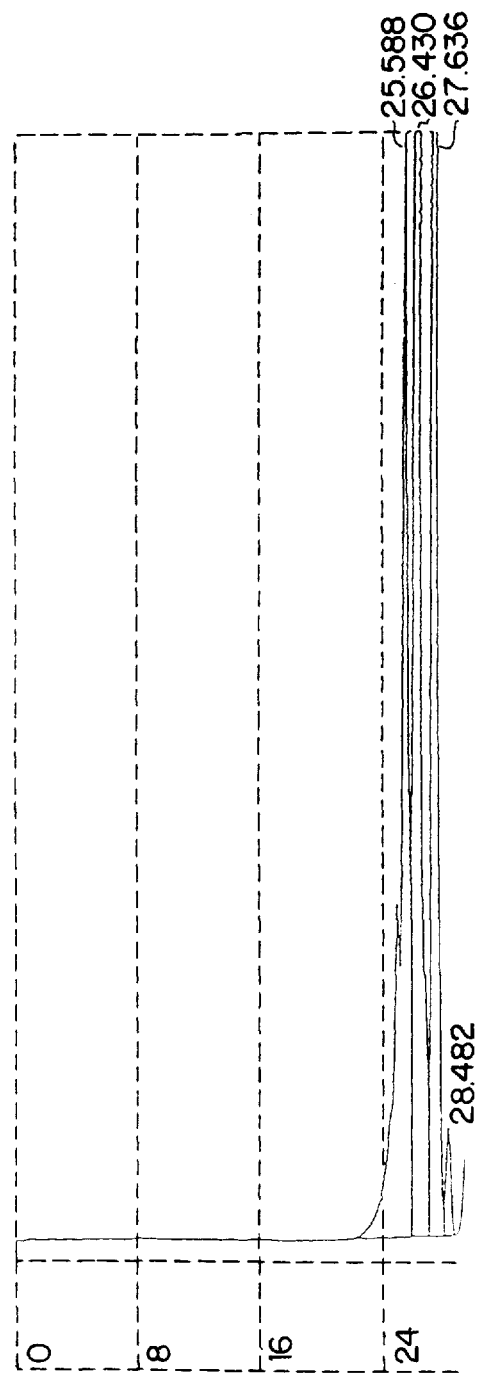
FIG. 55 is a GPC chart related to the starting epoxy compound in Example 11.
Figure 56:
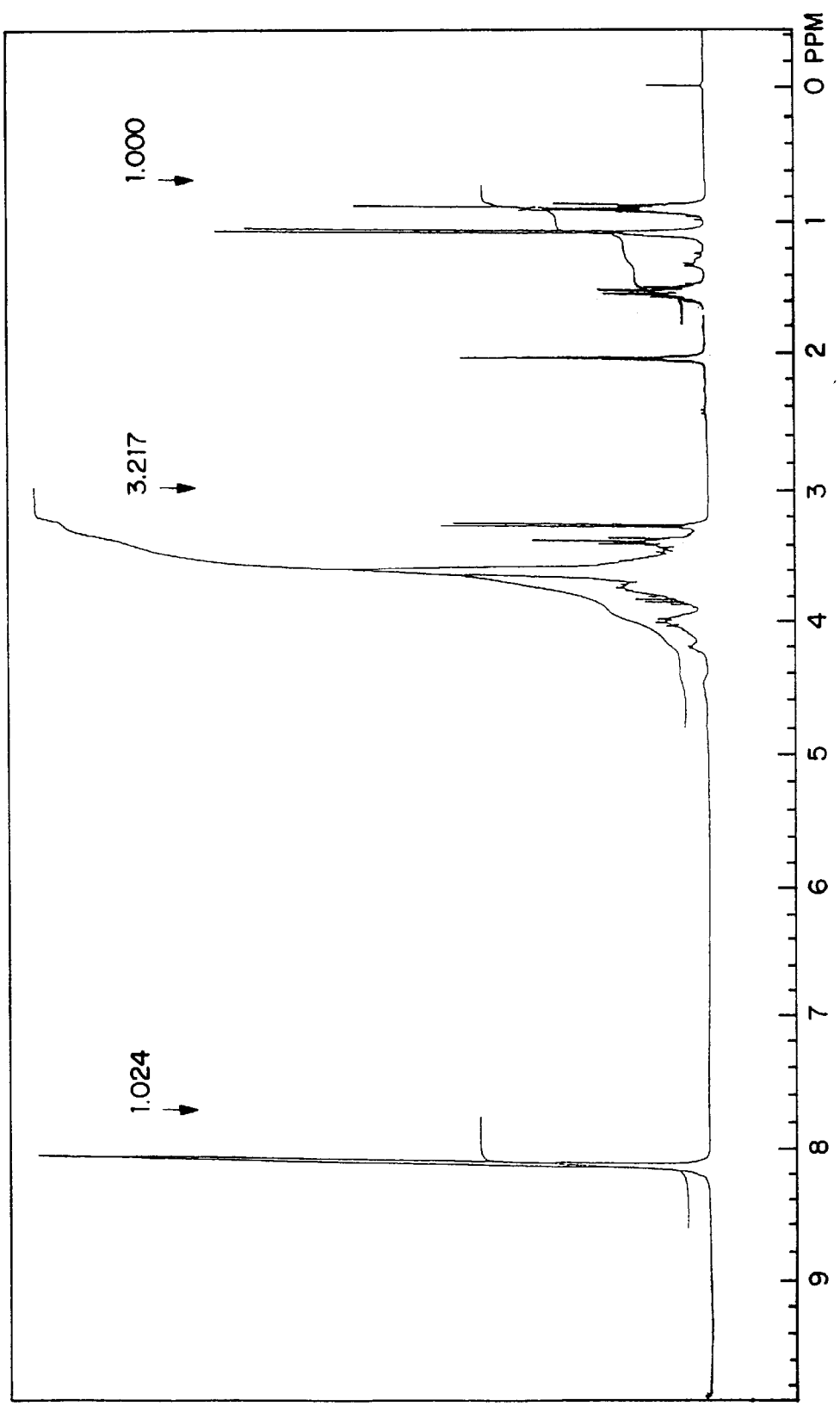
FIG. 56 is an NMR chart related to the phosphatized compound obtained in Example 11.

FIGS. 54, 55 and 56 are an NMR chart, an IR spectra chart and a GPC chart relating to the starting epoxy compound, respectively.

Figure 57:
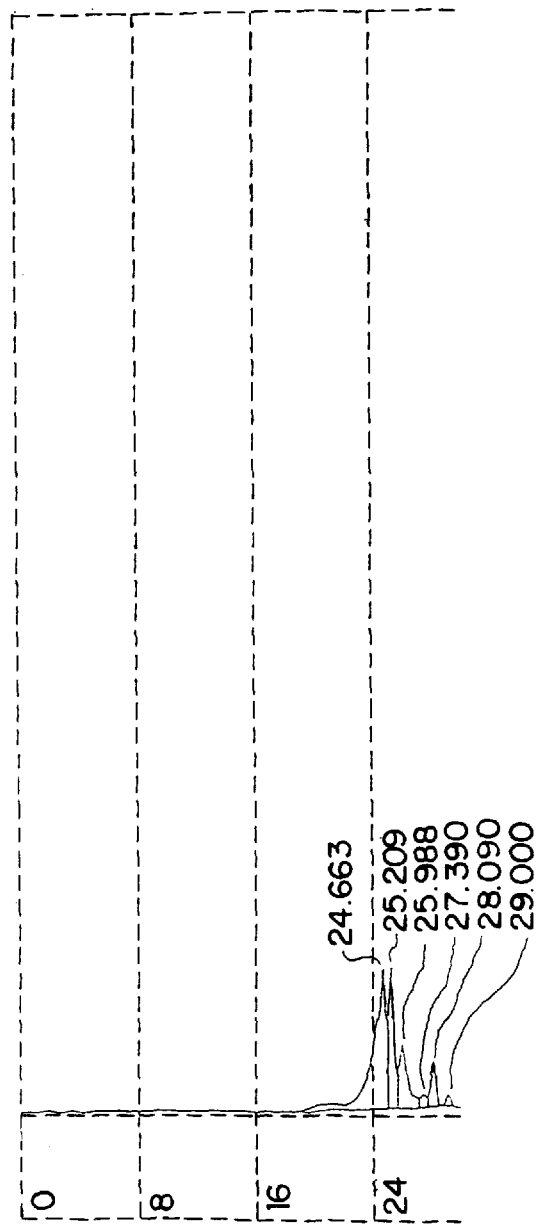
FIG. 57 is a GPC chart related to the phosphatized compound obtained in Example 11.
Figure 58:
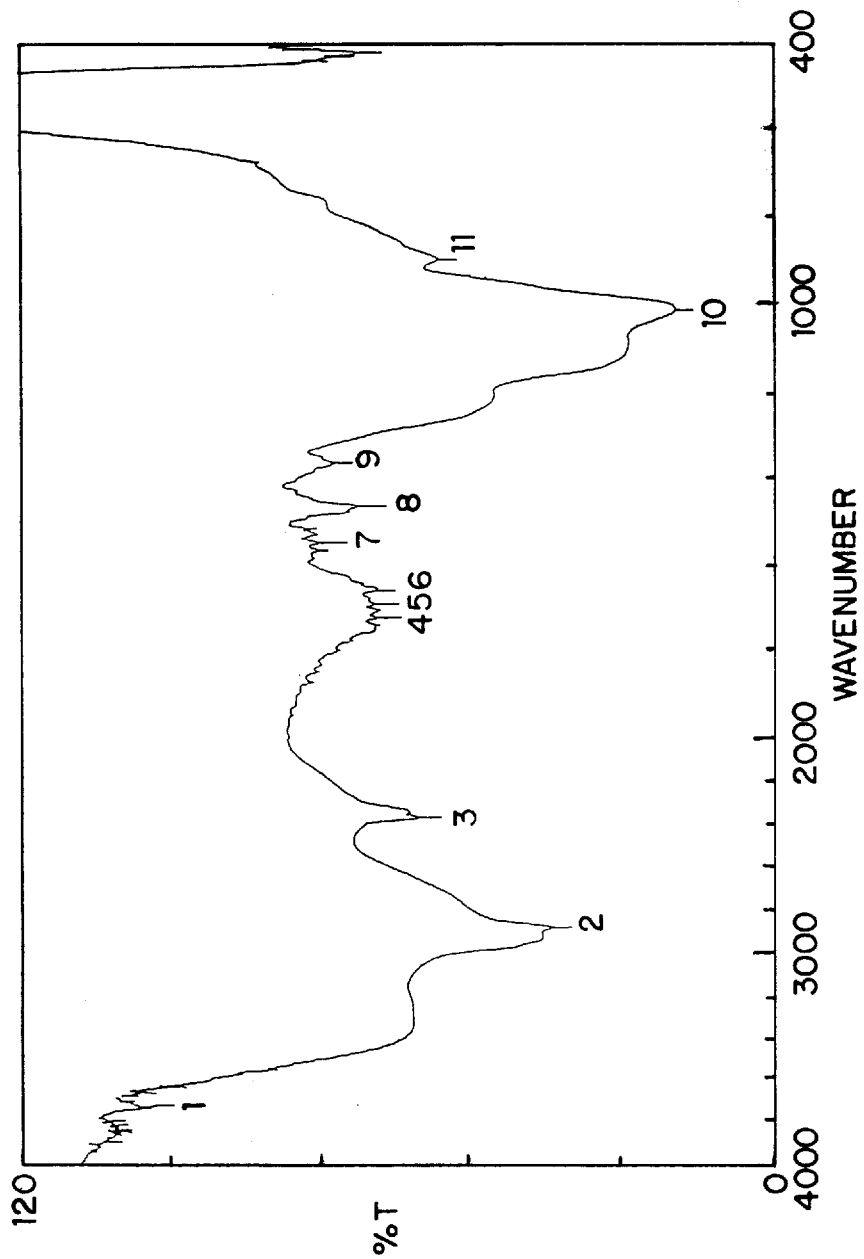
FIG. 58 is an IR spectra chart related to the phosphatized compound obtained in Example 11.

FIGS. 56, 57 and 58 are an NMR chart, a GPC chart and an IR spectra chart relating to the phosphatized compound obtained, respectively.

There was carried out characterization of the charts in relation to the phosphatized compound. Results are shown below.

NMR(delta ppm): 8.2(P-OH)4H, 3.9–4.2(C-H)2H, 3.2–3.7(CH$_2$)12H IR(cm$^{-1}$): 3736(OH), 2879(alkyl groups), 1000–1020(P-O) GPC: Mw=749, Mn=383, Mw/Mn=1.954

EXAMPLE 19

There were carried out respective spectrum analyses in relation to the sample obtained in Example 12.

Figure 59:
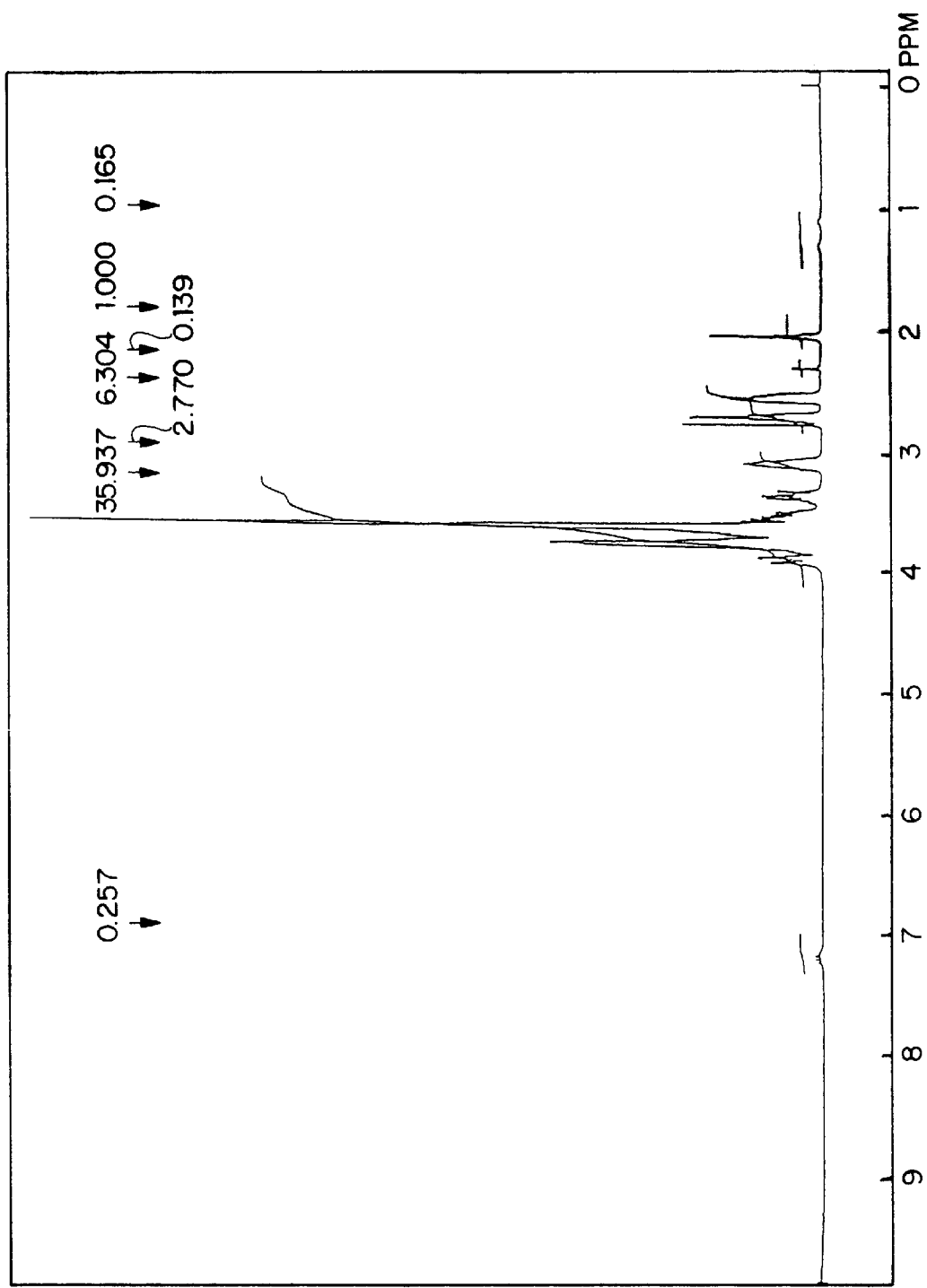
FIG. 59 is an NMR chart related to the starting epoxy compound in Example 12.
Figure 60:
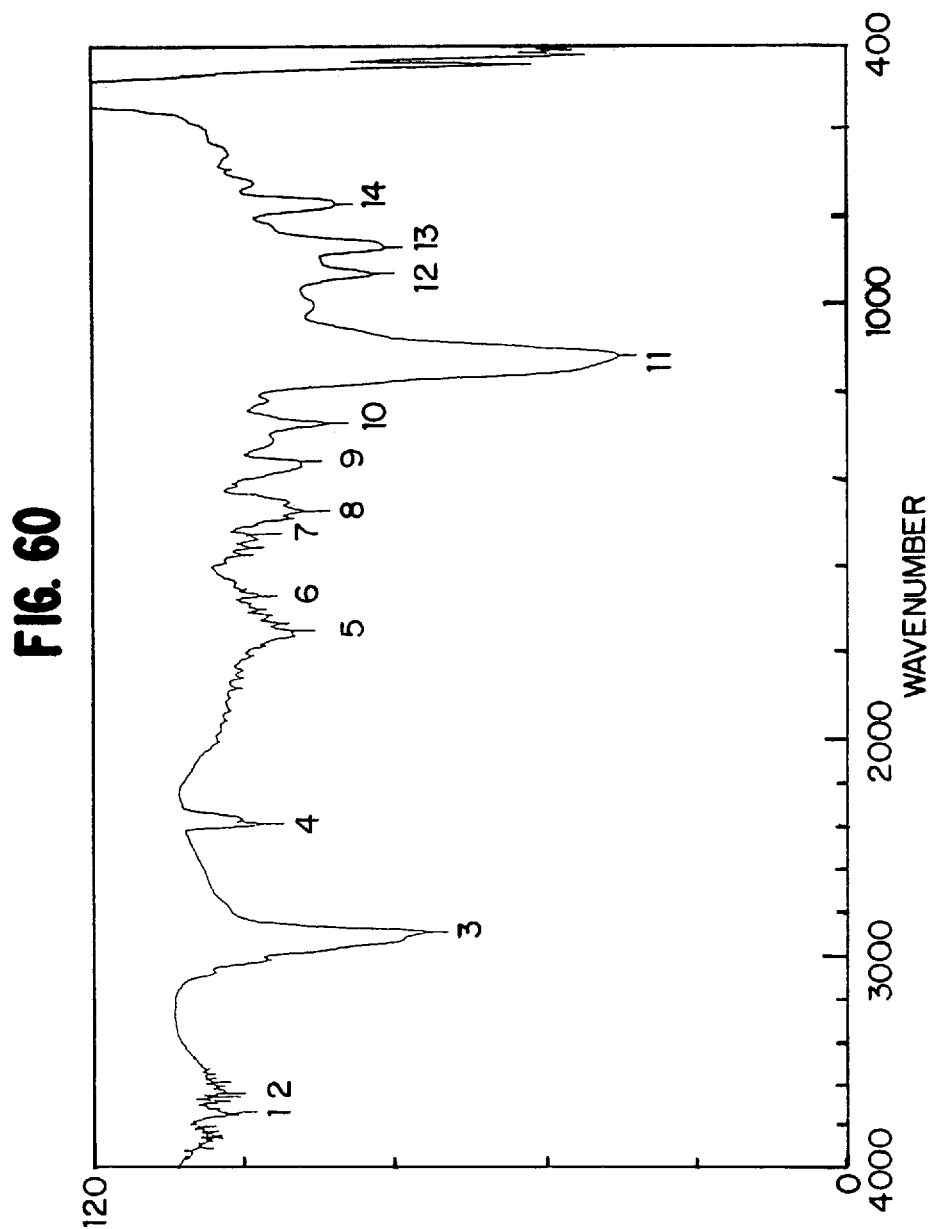
FIG. 60 is an IR spectra chart related to the starting epoxy compound in Example 12.
Figure 61:
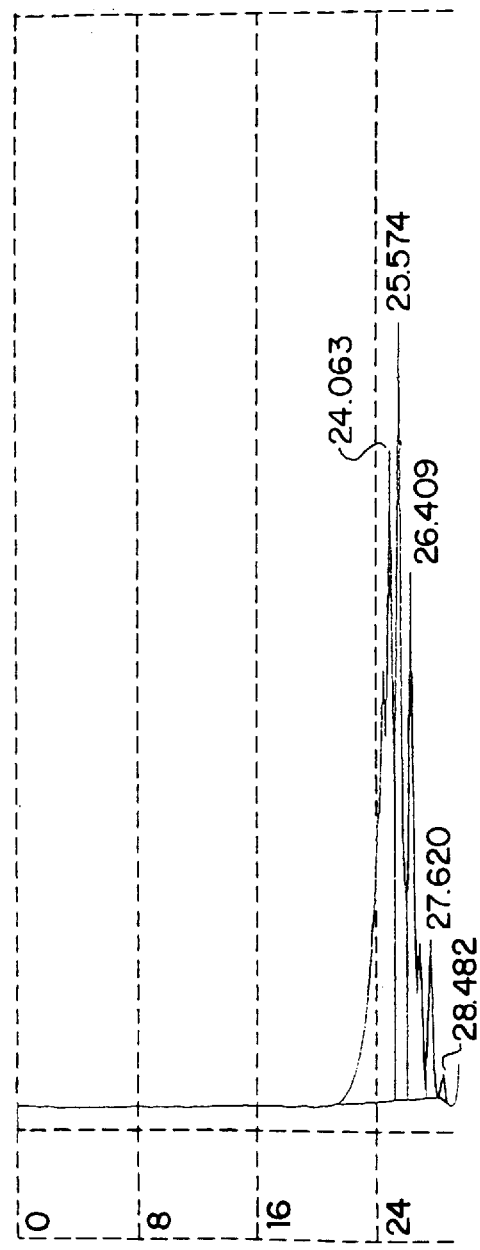
FIG. 61 is a GPC chart related to the starting epoxy compound in Example 12.

FIGS. 59, 60 and 61 are an NMR chart, an IR spectra chart and a GPC chart relating to the starting epoxy compound, respectively.

Figure 62:
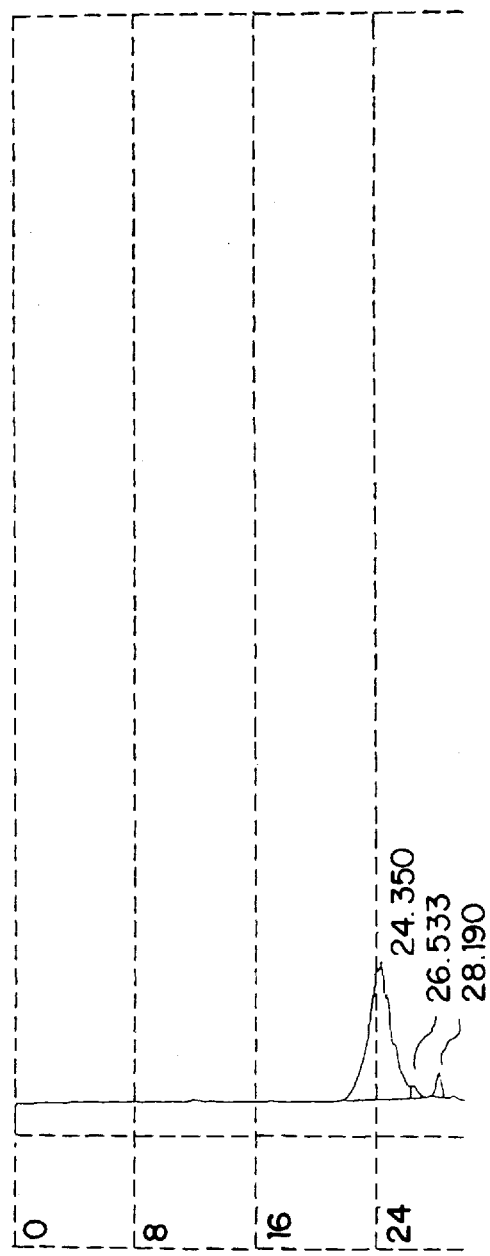
FIG. 62 is a GPC chart related to the phosphatized compound obtained in Example 12.
Figure 63:
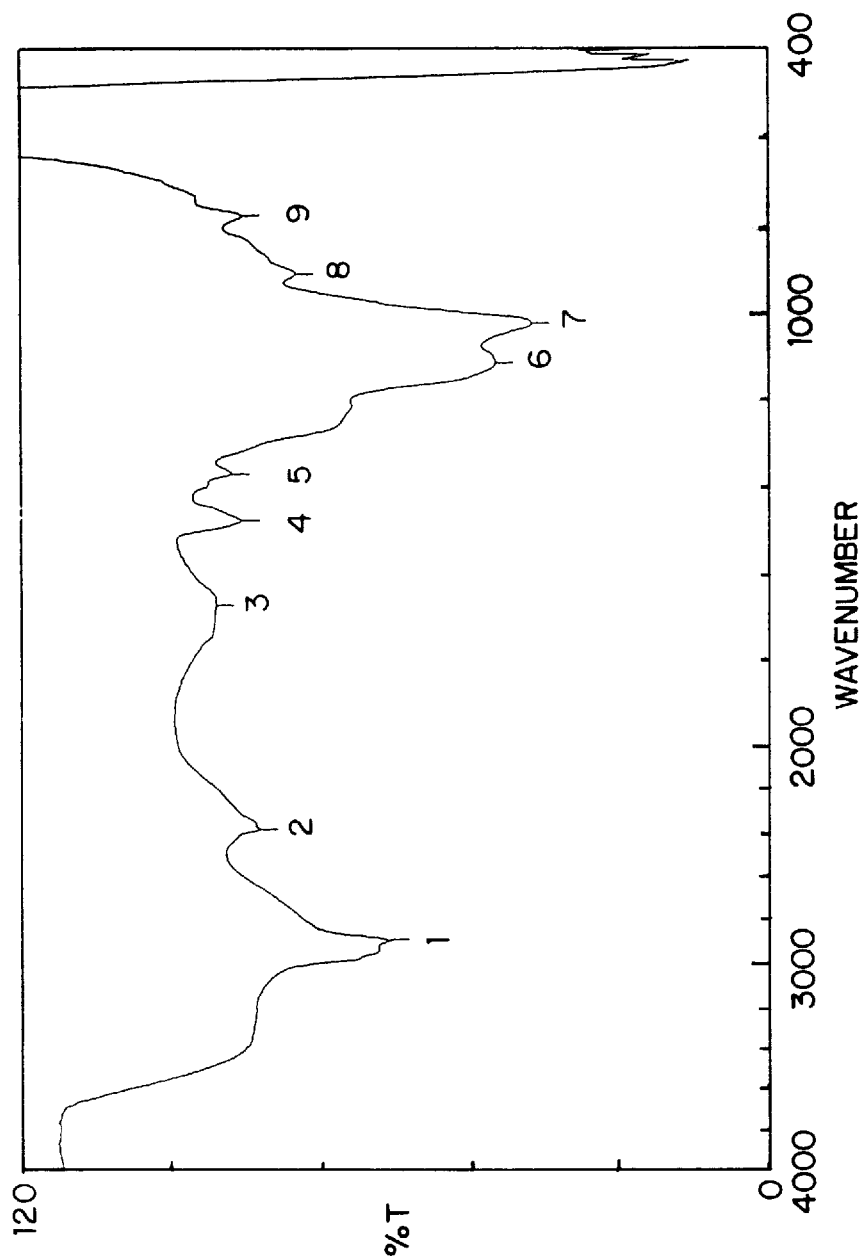
FIG. 63 is an IR spectra chart related to the phosphatized compound obtained in Example 12.

FIGS. 62 and 63 are a GPC chart and an IR spectra chart relating to the phosphatized compound obtained, respectively.

There was carried out characterization of the charts in relation to the phosphatized compound. Results are shown below.

NMR(delta ppm): 3.9–4.2(C-H), 3.2–3.7(CH$_2$), 8.2(P-OH) IR(cm$^{-1}$): 3700(OH), 2878(alkyl groups), 1010–1100 (P-O) GPC: Mw=740, Mn=370, Mw/Mn=2.0

EXAMPLE 20

There was carried out characterization of the charts in relation to the phosphatized compound obtained in Example 13. Results are shown below.

NMR (delta ppm): 8.0(P-OH)4H, 3.8–4.2(C-H)2H, 3.8–3.4(CH$_2$)8H, 2.0 (CH$_2$)4H, 0.8(CH$_3$)6H IR(cm$^{-1}$): 3700 (OH), 2800(alkyl groups), 950–1100(P-OH) GPC: Mw=832, Mn=457, Mw/Mn=1.82

EXAMPLE 21

There was carried out characterization of the charts in relation to the phosphatized compound obtained in Example 14. Results are shown below.

NMR (delta ppm): 8.1(P-OH)6H, 3.8–4.3(C-H)4H , 2.9–3.7(CH$_2$)20H IR(cm$^{-1}$): 3300(P-OH), 2870(alkyl groups), 980–1060(P-OH) GPC: Mw=832, Mn=457, Mw/Mn=1.82

EXAMPLE 22

There was carried out characterization of the charts in relation to the phosphatized compound obtained in Example 15. Results are shown below.

NMR (delta ppm): 8.1(P-OH)4H, 3.8–4.2(C-H)2H, 2.8–3.8(CH$_2$)24H IR(cm$^{-1}$): 3366(OH), 2878(alkyl groups), 980–1050(P-O absorption) GPC: Mw=602, Mn=472, Mw/Mn=1.277

EXAMPLE 23

There was carried out characterization of the charts in relation to the phosphatized compound obtained in Example 16. Results are shown below.

NMR(delta ppm): 8.2(P-OH)2H, 4.2–3.8(CH)4H, 3.8–3.2 (CH$_2$)14H 1.2(CH$_3$)9H IR(cm$^{-1}$): 2879(alkyl groups), 1000–1100(P-O absorption) GPC: Mw=575, Mn=461, Mw/Mn=1.248

While the invention has been described in detail and with reference to specific embodiments thereof, it will be apparent to one skilled in the art that various changes and modifications can be made therein without departing from the spirit and scope thereof.

What is claimed is:

1. A process for the preparation of a composition which comprises a phosphatized alicyclic compound represented by the formula (I):

$$R^1 \begin{cases} CO(X)_{n1}O-CH_2-Y^1 \\ CO(X)_{n2}O-CH_2-Y^1 \\ CO(X)_{n3}O-CH_2-Y^1 \\ \vdots \\ CO(X)_{nL}O-CH_2-Y^1 \end{cases} \quad (I)$$

said process comprising reacting an alicyclic epoxy compound represented by the formulae (IV):

$$R^1 \diagdown \begin{matrix} CO(X)_{n1}-O-CH_2-Y^2 \\ CO(X)_{n2}-O-CH_2-Y^2 \\ CO(X)_{n3}-O-CH_2-Y^2 \\ \vdots \\ CO(X)_{nL}-O-CH_2-Y^2 \end{matrix} \quad (IV)$$

in formulae (I) and (IV), $R^1$ is an alkyl group or alkenyl group having a carbon number of 1 to 30; X is —O—$(CR^aR^b)_nCO$— in which $R^a$ and $R^b$ are independently hydrogen or a methyl group; n is a number of 4 to 8; n1 to nL represent 0 or a number above 0—, respectively; n1+n2+n3+ . . . +nL is 1 or a number above 1; $Y^1$ is a structural group represented by the formula (1):

(1)

OH
O—P(=O)(OH)$_2$, $Y^2$ is a structural group represented by the formula

O, with a compound having the —OP(=O)(OH)$_2$ group in the molecule.

2. A process for the preparation of a composition which comprises a phosphatized alicyclic compound represented by the formula (II):

$$Y^1-CO-[-X-]_{n1}-O-CH_2-Y^1 \quad (II),$$

said process comprising reacting an alicyclic epoxy compound represented by the formula (V):

$$Y^2-CO-[-X-]_{n1}-O-CH_2-Y^2 \quad (V),$$

in formulae (II) and (V), X is —O—$(CR^aR^b)_nCO$— in which $R^a$ and $R^b$ are independently hydrogen or a methyl group; n is a number of 4 to 8, n1 is 0 or a number above 0 and $Y^1$ is a structural group represented by the formula (1):

OH
O—P(=O)(OH)$_2$, and $Y^z$ is a structural group represented by the formula

O with a compound having the —OP(=O)(OH)$_z$ group in the molecule.

3. A process as set forth according to claim 2, wherein said compound having the —OP(=O)(OH)$_2$ group in the molecule is orthophosphoric acid or a monoester thereof.

4. A process for the preparation of a composition which comprises a phosphatized alicyclic compound represented by the formula (III):

$$Y^1-CH_2OCO(CH_2)_4COO-CH_2-Y^1 \quad (III),$$

said process comprising reacting an alicyclic epoxy compound represented by the formula (VI):

$$Y^2-CH_2OCO(CH_2)_4COO-CH_2-Y^2 \quad (VI),$$

in formulae (III) and (VI), $Y^1$ is a structural group represented by the formula (1):

OH
O—P(=O)(OH)$_2$ and $Y^2$ is a structural group represented by the formula

O, with a compound having the —OP(=O)(OH)$_2$ group in the molecule.

5. A process as set forth according to claim 4, wherein said compound having the —OP(=O)(OH)$_2$ group in the molecule is orthoposhoric acid or a monoester thereof.

6. A process as set forth in claim 1, wherein said compound having the —OP(=O)(OH) group in the molecule is orthophosphoric acid or a monoester thereof.

7. A process for the preparation of a composition which comprises a phosphatized alicyclic compound represented by formula (VII):

$$R^2 \diagdown \begin{matrix} (A)_{n1}-H \\ (A)_{n2}-H \\ \vdots \\ (A)_{nL}-H \end{matrix} \quad (VII)$$

said process comprising reacting an alicyclic epoxy compound represented by the formula (VIII):

$$R^2 \diagdown \begin{matrix} (B)_{n1}-H \\ (B)_{n2}-H \\ \vdots \\ (B)_{nL}-H \end{matrix} \quad (VIII)$$

in formulae (VII) and (VIII), $R^2$ is a residual group of an organic compound having at least one active hydrogen atom; n1 to nL represent an integer of 0 to 30, respectively; n1+n2n3+ . . . +nL is an integer of 1 to 100; L is an integer of 1 to 10 which corresponds to the number of the active hydrogen atom in the organic compound and A represents an oxycyclohexane structure represented by the formula:

O—

$X^1$, $X^1$ represents the following structural units:

—CH=CH$_2$, —CH—CH$_2$—OH,
\O
O=P—(OH)$_2$

-continued

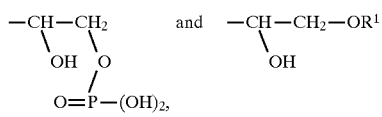

and B represents an oxycyclohexane structure represented by the formula:

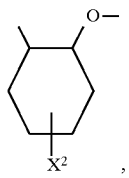

$X^2$ represents the following structural units:

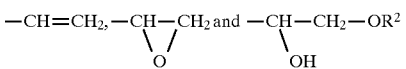

wherein at least one $X^2$ represents an epoxyethyl group, $R^x$ is any of hydrogen, an alkyl group, an alkylcarbonyl group and an arylcarbonyl group, with a compound having the $-OP(=O)(OH)_2$ group in the molecule.

8. A process for the preparation of a composition that comprises a phosphoric acid adduct of propylene glycol diglycidyl ether, diethylene glycol diglycidyl ether, trimethylolpropane triglycidyl ether, or pentaerythritol tetraglycidyl ether, said process comprising reacting said propylene glycol diglycidyl ether, said diethylene glycol diglycidyl ether, said trimethylolpropane triglycidyl ether, or said pentaerythritol tetraglycidyl ether, respectively, with a phosphoric acid.

* * * * *